(12) United States Patent
Juillerat et al.

(10) Patent No.: US 10,988,542 B2
(45) Date of Patent: Apr. 27, 2021

(54) CHIMERIC ANTIGEN RECEPTORS WITH INTEGRATED CONTROLLABLE FUNCTIONS

(71) Applicant: CELLECTIS, Paris (FR)

(72) Inventors: Alexandre Juillerat, New York, NY (US); Philippe Duchateau, Draveil (FR); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 449 days.

(21) Appl. No.: 15/752,195

(22) PCT Filed: Aug. 24, 2016

(86) PCT No.: PCT/EP2016/069918
§ 371 (c)(1),
(2) Date: Feb. 12, 2018

(87) PCT Pub. No.: WO2017/032777
PCT Pub. Date: Mar. 2, 2017

(65) Prior Publication Data
US 2018/0237533 A1    Aug. 23, 2018

(30) Foreign Application Priority Data

Aug. 24, 2015 (DK) .............................. PA201570545
Dec. 23, 2015 (EP) .................................... 15202592

(51) Int. Cl.
| | |
|---|---|
| *C07K 14/725* | (2006.01) |
| *C07K 14/72* | (2006.01) |
| *C07K 16/28* | (2006.01) |
| *A61K 35/17* | (2015.01) |
| *A61P 35/00* | (2006.01) |
| *A61K 31/436* | (2006.01) |
| *A61K 38/00* | (2006.01) |

(52) U.S. Cl.
CPC ........ *C07K 16/2869* (2013.01); *A61K 31/436* (2013.01); *A61K 35/17* (2013.01); *A61P 35/00* (2018.01); *C07K 14/7051* (2013.01); *C07K 14/721* (2013.01); *C07K 16/2803* (2013.01); *A61K 38/00* (2013.01); *C07K 2317/622* (2013.01); *C07K 2319/03* (2013.01); *C12N 2510/00* (2013.01)

(58) Field of Classification Search
CPC .. C07K 14/7051; C07K 14/721; A61K 35/17; A61K 35/00; A61K 31/536
See application file for complete search history.

(56) References Cited

U.S. PATENT DOCUMENTS

| | | | |
|---|---|---|---|
| 2014/0010791 A1* | 1/2014 | Wandless ............. | A61K 31/445 424/93.21 |
| 2016/0311907 A1* | 10/2016 | Brogdon .......... | C07K 14/70521 |

FOREIGN PATENT DOCUMENTS

| | | |
|---|---|---|
| WO | 2014/127261 A1 | 8/2014 |
| WO | 2015/142661 A1 | 9/2015 |

OTHER PUBLICATIONS

Gargett Tessa et al: "The inducible caspase-9 suicide gene system as a "safety switch" to limit on-target, off-tumor toxicities of chimeric antigen receptor T cells." Frontiers in Pharmacology, vol. 5, 235, Oct. 2014 (Oct. 2014), pp. 1-7.

(Continued)

*Primary Examiner* — Jessica H Roark
(74) *Attorney, Agent, or Firm* — Arrigo, Lee, Guttman & Mouta-Bellum LLP

(57) ABSTRACT

The present invention relates to the field of cell immunotherapy and more particularly to a new generation of chimeric antigen receptors (CAR), allowing the control of immune cells endowed with such CARs through the interaction with small molecules. More particularly, the present invention relates to chimeric antigen receptor which comprise in at least one ectodomain a molecular switch turning the antigen binding function of the receptor from an off to on state, and vice versa. The present invention thus provides more controlled and potentially safer engineered CAR endowed immune cells, such as T-lymphocytes.

17 Claims, 13 Drawing Sheets
Specification includes a Sequence Listing.

(56) References Cited

OTHER PUBLICATIONS

Lihua E. Budde et al: Combining a CD20 Chimeric Antigen Receptor and an Inducible Caspase 9 Suicide Switch to Improve the Efficacy and Safety of T Cell Adoptive Immunotherapy for Lymphoma,: PLOS ONE, vol. 8, No. 12, E82742 (Dec. 17, 2013), pp. 1-10.
Min Soo Kim et al: "Redirection of Genetically Engineered CAR-T Cells Using Bifunctional Small Molecules," Journal of the American Chemical Society, vol. 137, No. 8 (Mar. 4, 2015) pp. 2832-2835.
Clackson T et al: "Redesigning an FKBP-ligand interface to generate chemical dimerizers with novel specificity" Proceedings of the National Academy of Sciences, National Academy of Sciences, US, vol. 95, No. 18 (Sep. 1, 1998) pp. 10437-10442.
Keenan T et al: "Synthesis and activity of bivalent FKBP12 ligands for the regulated dimerization of proteins," Bioorganic & Medicinal Chemistry, Pergamon, GB, vol. 6, No. 8 (Aug. 1, 1998) pp. 1309-1335.
Anonymous: SNAP-vitro for protein interaction assays:FKBP/FRB binding assay using biotin capture on streptavidin coated plates, Covalys Biosciences Internet Citation, Aug. 2005 (Aug. 2005), XP002472871, Retrieved from the Internet: URL:http://www.covalys.com/fileadmin/docum ents/snap vitro fkbp interaction -assay.pdf [retrieved on Mar. 13, 2008].
International Search Report for PCT/EP2016/069918 dated Nov. 24, 2016.
International-Type Search Report for DK2015170545 completed Apr. 29, 2016.
Banaszynski et al., "Characterization of the FKBP-Rapamycin-FRB Ternary Complex." Journal of the American Chemical Society, 2005, 127(13): 4715-4721.

\* cited by examiner

B

A

B

CHIMERIC ANTIGEN RECEPTORS WITH INTEGRATED CONTROLLABLE FUNCTIONS

SEQUENCE LISTING

The instant application contains a Sequence Listing which has been submitted electronically in ASCII format and is hereby incorporated by reference in its entirety. Said ASCII copy, created on Feb. 12, 2018, is named P81502686US00_SL and is 158,720 bytes in size.

FIELD OF THE INVENTION

The present invention relates to the field of cell immunotherapy and more particularly to a new generation of chimeric antigen receptors (CAR), allowing the control of immune cells endowed with such CARs through the interaction with small molecules. More particularly, the present invention relates to chimeric antigen receptors which comprise in at least one ectodomain a molecular switch controlling the antigen binding function of the receptor. The present invention thus provides more controlled and potentially safer engineered CAR endowed immune cells, such as T-lymphocytes.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

However, although numerous clinical studies have demonstrated the potential of adoptive transfer of CAR T cells for cancer therapy, they have also raised the risks associated with the cytokine-release syndrome (CRS) and the "on-target off-tumor" effect. To date, few strategies have been developed to pharmacologically control CAR engineered T-cells and mainly rely on suicide mechanisms. Such suicide strategies leading to a complete eradication of the engineered T-cells will result in the premature end of the treatment.

Consequently, there is a great need of implementing non-lethal control of engineered CAR T-cells to improve the CAR T-cell technology and its safety.

SUMMARY OF THE INVENTION

Here, the inventors have developed a system where controlled variations in the conformation of the extracellular portion of a CAR containing the antigen-binding domain could be obtained upon addition of small molecules. This integrated system switches the interaction between the antigen and the antigen binding domain between on/off states. Particularly, by being able to control the confirmation of the extracellular portion of a CAR, downstream functions of an immune cell, such as cytotoxicity of T cell, endowed with such chimeric antigen receptor can be directly modulated. This system provides for novel more controlled and potentially safer engineered CAR endowed immune cells.

The present invention thus provides in a first aspect a chimeric antigen receptor (CAR) characterized in that it comprises:
a) at least one ectodomain which comprises:
  i) an extracellular antigen binding domain; and
  ii) a switch domain comprising at least a first multimerizing ligand-binding domain and a second multimerizing ligand-binding domain which are capable of binding to a predetermined multivalent ligand to form a multimer comprising said two binding domains and the multivalent ligand to which they are capable of binding;
b) at least one transmembrane domain; and
c) at least one endodomain comprising a signal transducing domain and optionally a co-stimulatory domain;
wherein the switch domain is located between the extracellular antigen binding domain and the transmembrane domain.

The present invention provides in further aspect polynucleotides and vectors comprising one or more nucleic acid sequences encoding a chimeric antigen receptor of the present invention.

The present invention provides in a further aspect an immune cell, and more particularly an isolated immune cell, which comprises (e.g., expresses on its surface) at least one chimeric antigen receptor of the present invention.

The present invention provides in a further aspect methods for engineering an immune cell of the present invention.

The present invention provides in a further aspect the use of immune cells of the present invention in therapy, such as for use in the treatment of cancer.

The architecture of the CAR of the inventions provides for a reliable functionality since the first multimerizing ligand-binding domain and second multimerizing ligand-binding domain constituting the molecular switch are present on the same polypeptide molecule. This architecture makes the CAR system of the invention independent from factors which may otherwise have an influence on the proper expression and positioning of the ligand-binding domains on

DETAILED DESCRIPTION OF THE INVENTION

Figure 1:
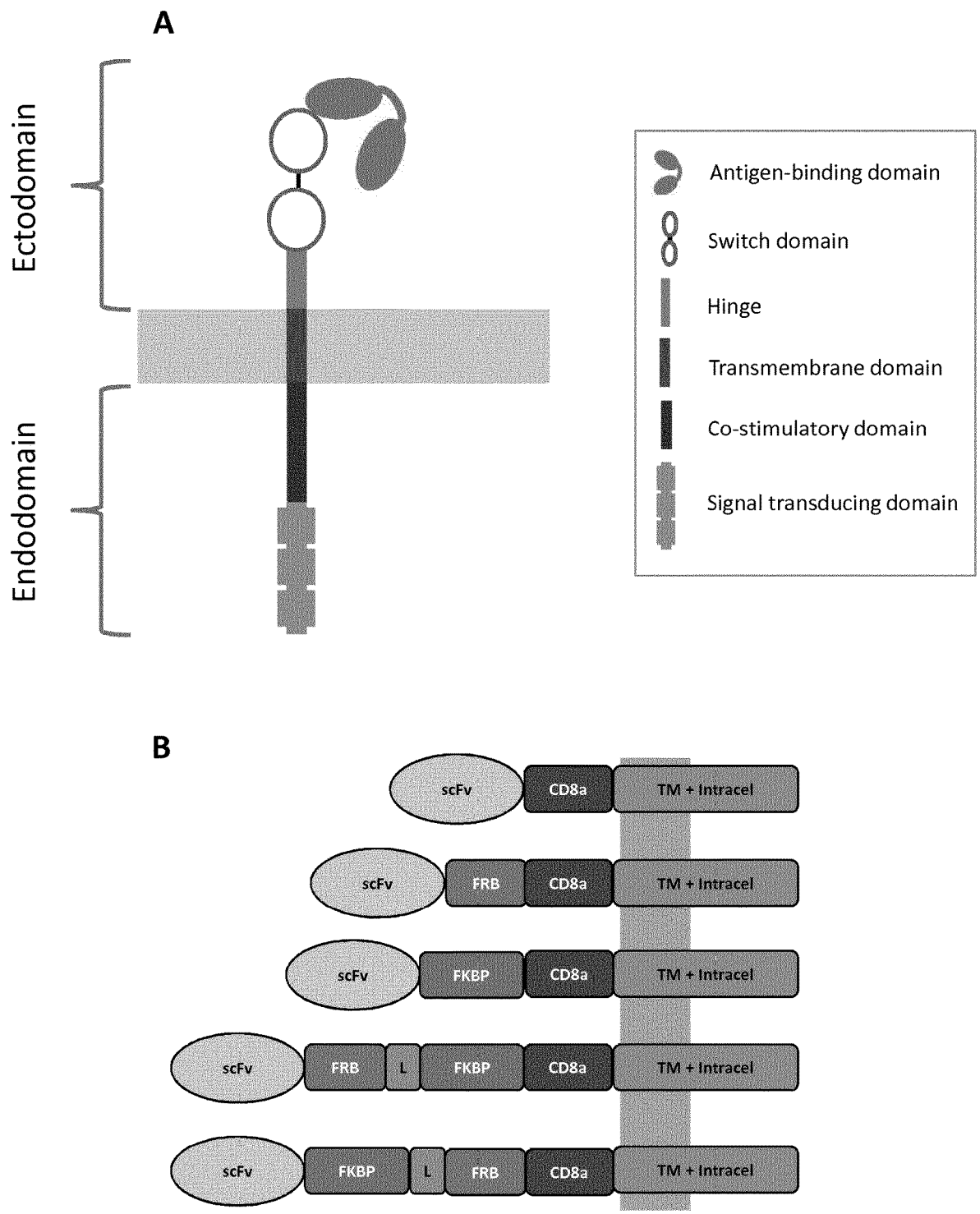
FIG. 1. (A) Schematic illustration of a single chain chimeric antigen receptor according to the present invention. (B) Schematic illustration of the CAR ectodomains used in the examples. Both lower structures incorporate FRB and FKBP domains according to the present invention.

Unless specifically defined herein, all technical and scientific terms used have the same meaning as commonly understood by a skilled artisan in the fields of gene therapy, biochemistry, genetics, and molecular biology.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Chimeric Antigen Receptors of the Invention

The present invention thus provides in a first aspect a chimeric antigen receptor (CAR) characterized in that it comprises:

a) at least one ectodomain which comprises:
  i) an extracellular antigen binding domain; and
  ii) a switch domain comprising at least a first multimerizing ligand-binding domain and a second multimerizing ligand-binding domain which are capable of binding to a predetermined multivalent ligand to form a multimer comprising said two binding domains and the multivalent ligand to which they are capable of binding;
b) at least one transmembrane domain; and
c) at least one endodomain comprising a signal transducing domain and optionally a co-stimulatory domain;
wherein the switch domain is located between the extracellular antigen binding domain and the transmembrane domain.

Upon simultaneous binding of the multivalent ligand to the first and second multimerizing ligand-binding domains, a multimeric, such as dimeric, complex is formed which leads to a conformational change within the ectodomain of the chimeric antigen receptor, which in turn improves the surface exposition of the antigen binding domain.

A "multimerizing ligand" or "multimerizer", is a multivalent ligand which is capable of simultaneously binding to at least two binding partners, such as the first and second multimerizing ligand-binding domains, causing upon binding a multimerization, such as dimerization, of the binding partners. More particularly, a "multivalent ligand" is a molecule, preferably a small molecule, which possesses at least two binding sites allowing the simultaneous binding of at least two binding partners, such as the first and second multimerizing ligand-binding domains. The terms "multimerizing ligand", "multimerizer" and "multivalent ligand" can be used herein interchangeably, and include the terms "dimerizing ligand", "dimerizer" and "bivalent ligand", respectively. A "dimerizing ligand", "dimerizer" or "bivalent ligand", is a molecule, preferably a small molecule, which possesses two binding sites allowing the binding of two ligand binding partners, such as the first and second multimerizing ligand-binding domains, thus causing the dimerization thereof.

A "small molecule", as used herein, is a low molecular weight (<2000 daltons) organic compound. Non-limiting examples of small molecules which find application in the present invention include the macrolide rapamycin and its analogs, also known as "rapalogs", such as AP21967, Deforolimus (AP23573), everolimus (RAD001), and temsirolimus (CCI-779). Other non-limiting examples of small molecules which find application in the present invention include tacrolimus (FK506), FK506 derivatives, such as FK1012, FK506 analogs, such as AP1903. Yet other non-limiting examples of small molecules which find application in the present invention include coumermycin, gibberellin, HaXs, AP1510, AP20187 and AP21967.

A "multimerizing ligand" may also be a peptide or nucleic acid (natural or synthetic).

According to certain embodiments, the first multimerizing ligand-binding domain and the second multimerizing ligand binding domain are derived from a chemical induced dimerization (CID) system.

CID systems are based on the mechanism by which two polypeptides bind only in the presence of a certain small molecule or other dimerizing agent. A variety of CID systems is known and may be employed in accordance with the present invention. Non-limiting examples of suitable CID systems are provided in Table 1 below.

| First multimerizing ligand-binding domain | Second multimerizing ligand-binding domain | Dimerizer(s) |
| --- | --- | --- |
| FKBP12 | FRB | Rapamycin, rapalogs (AP21967, AP23573, RAD001, CCI-779) |
| FKBP12 | FKBP12 | FK1012, AP1510 |
| FKBP12 (F36V) | FKBP12(F36V) | AP1903, AP20187 |
| FKBP12 | FRB(T2098L) | Rapamycin, AP21967 |
| FKBP12 | CalcineurinA (CnA) | FK506 |
| FKBP12 | Cyclophilin (CyP) | FKCsA |
| GyrB | GyrB | Coumermycin |
| GAI | GID1A | Gibberellin |
| GAI | GID1B | Gibberellin |
| GAI | GID1C | Gibberellin |
| Snap-tag | Halo-tag | HaXs |
| Snap-tag | CLIP-tag | sc |
| DHFR | DHFR | BisMTX |
| glucocorticoid receptor ligand-binding domain | DHFR | Dex-Mtx, Dex-TMP |
| PYL1 (PYLcs, amino acids 33 to 209) | ABI1 (ABIcs, amino acids 126 to 423) | S-(+)-abscisic acid (ABA) |

AP21967 is a rapamycin analog with heterodimerizing activity. Dimerizer AP21967 heterodimerizes FKBP12 with a variant of FRB which contains a single amino acid substitution (T2098L).

AP1903 is a tacrolimus analog with homodimerizing activity. Dimerizer AP1903 homodimerizes a variant of FKBP12 which contains a single amino acid substitution (F36V).

Figure 9:
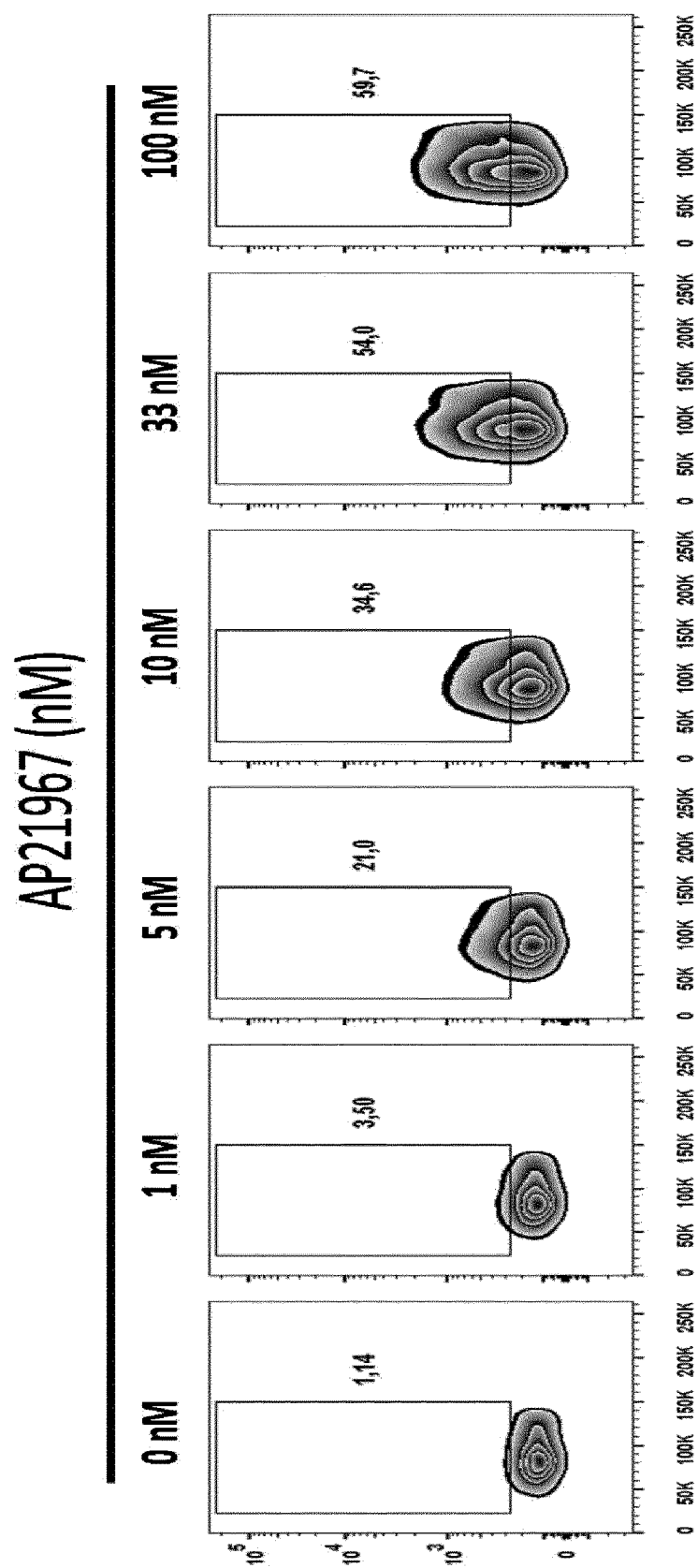
FIG. 9. Percentages of live cells positive for surface detection of FKBP/FRB*-mcCAR in function of presence of increasing dose of AP21967.

According to certain embodiments, Tacrolimus analogs, like AP1903 or other macrolide immunosuppressants, can be used to further modulate CAR mediated activation of the immune cells as per the present invention. They can act as small molecule competitors offering additional control of the engineered CAR T-cells. As an illustration of the possibility to tune the amount of CAR locked in an on-state at the cell surface, tacrolimus (FK506) was used by the inventors as a small molecule known to bind to the FKBP12 without enabling to form a complex with the FRB (see Example 4 and FIG. 6). AP21967 (or rapamycin) and tacrolimus have identical FKBP12 binding core and compete for the same binding site within the FKBP moiety (Wilson, K. P. et al. 1995. Comparative X-ray structures of the major binding protein for the immunosuppressant FK506 (tacrolimus) in unliganded form and in complex with FK506 and rapamycin. *Acta Crystallogr D Biol Crystallogr* 51, 511-521). As shown in FIG. 9, T-cells transfected with the engineered CAR incubated with a fixed amount of AP21967 and increasing amount of tacrolimus (0 to 10 mM, preferably 0 to 500 nM) show decreased surface detection of the CAR. Accordingly, the method according to the present invention aiming to switch-on CAR induced activation of an immune cell, can comprise an additional step where said induction is modulated by contacting said immune cells in-vivo or in-vitro with a tacrolimus analog or macrolide immunosuppressant. This may be done to tune, reduce or suppress the activation of the immune cells by the CAR object of the present invention.

The dimerizer HaXS is described in, e.g., Erhart, D. et al. (2013), "Chemical development of intracellular protein heterodimerizers", Chemistry & Biology 20: 549-557.

The dimerizer sc is described in, e.g., Gaultier, A. et al. (2009), "Selective cross-linking of interacting proteins using self-labeling tags", J Am Chem Soc. 131(49):17954-62.

The dimerizer BisMTX is described in, e.g., Kopytek, S. J. et al. (2000), "Chemically induced dimerization of dihydrofolate reductase by a homobifunctional dimer of methotrexate", Chemistry & Biology 7:313-321.

The dimerizer Dex-Mtx is described in, e.g., Lin, H. N., et al. (2000), "Dexamethasone-methotrexate: An efficient chemical inducer of protein dimerization in vivo", Journal of the American Chemical Society, 122(17):4247-4248.

The dimerizer Dex-TMP is described in, e.g., Gallagher, S. S. et al. (2007) "An orthogonal dexamethasone-trimethoprim yeast three-hybrid system", Anal Biochem. 363(1):160-2.

The first multimerizing ligand-binding domain and second multimerizing ligand-binding domain can be the same or different. Thus, according to certain embodiments, the first multimerizing ligand-binding domain and second multimerizing ligand-binding domain are the same. According to other certain embodiments, the first multimerizing ligand-binding domain and second multimerizing ligand-binding domain are different.

According to certain embodiments, the first multimerizing ligand-binding domain and second multimerizing ligand-binding domain are selected from the pairs of multimerizing ligand-binding domains consisting of: FK506 binding protein (FKBP12):FKBP-rapamycin binding domain of mTOR (FRB), FKBP12:FKBP12, FKBP (F36V): FKBP (F36V), FKBP12:FRB (T2098L), FKBP12:Calcineurin A (CnA), FKBP12:Cyclophilin (CyP), GyrB:GyrB, GAI:GID1A, GAI:GID1B, GAI:GID1C, Snap-tag:Halo-tag, Snap-tag: CLIP-tag, DHFR:DHFR, glucocorticoid receptor ligand-binding domain:DHFR and PYL1:ABI1.

According to certain embodiments, the first multimerizing ligand-binding domain is FKBP12 (SEQ ID NO: 1) or a variant thereof having at least 80, such as at least 85, at least 90, at least 95, at least 98 or at least 99%, sequence identity with FKBP12 (SEQ ID NO: 1).

According to particular embodiments, the first multimerizing ligand-binding domain is FKBP12 (SEQ ID NO: 1).

According to other particular embodiments, the first multimerizing ligand-binding domain is a variant of FKBP12 having at least 80, such as at least 85, at least 90, at least 95, at least 98 or at least 99%, sequence identity with FKBP12 (SEQ ID NO: 1).

According to certain embodiments, the second multimerizing ligand-binding domain is also FKBP12 (SEQ ID NO: 1) or a variant thereof having at least 80, such as at least 85, at least 90, at least 95, at least 98 or at least 99%, sequence identity with FKBP12 (SEQ ID NO: 1).

According to particular embodiments, the second multimerizing ligand-binding domain is FKBP12 (SEQ ID NO: 1).

According to other particular embodiments, the second multimerizing ligand-binding domain is a variant of FKBP12 having at least 80, such as at least 85, at least 90, at least 95, at least 98 or at least 99%, sequence identity with FKBP12 (SEQ ID NO: 1).

According to certain embodiments, the second multimerizing ligand-binding domain is FRB (SEQ ID NO: 2) or a variant thereof having at least 80, such as at least 85, at least 90, at least 95, at least 98 or at least 99%, sequence identity with FRB (SEQ ID NO: 2).

According to particular embodiments, the second multimerizing ligand-binding domain is FRB (SEQ ID NO: 2).

According to other particular embodiments, the second multimerizing ligand-binding domain is a variant of FRB having at least 80, such as at least 85, at least 90, at least 95, at least 98 or at least 99%, sequence identity with FRB (SEQ ID NO: 2).

According to other particular embodiments, the first multimerizing ligand-binding domain is FKBP12 (SEQ ID NO: 1) or a variant thereof having at least 80, such as at least 85, at least 90, at least 95, at least 98 or at least 99%, sequence identity with FKBP12 (SEQ ID NO: 1), and the second multimerizing ligand-binding domain is FRB (SEQ ID NO: 2) or a variant thereof having at least 80, such as at least 85, at least 90, at least 95, at least 98 or at least 99%, sequence identity with FRB (SEQ ID NO: 2).

According to more particular embodiments, the first multimerizing ligand-binding domain is FKBP12 (SEQ ID NO: 1), and the second multimerizing ligand-binding domain is FRB (SEQ ID NO: 2) or a variant thereof having at least 80, such as at least 85, at least 90, at least 95, at least 98 or at least 99%, sequence identity with FRB (SEQ ID NO: 2).

According to other more particular embodiments, the first multimerizing ligand-binding domain is FKBP12 (SEQ ID NO: 1), and the second multimerizing ligand-binding domain is FRB (SEQ ID NO: 2).

According to other more particular embodiments, the first multimerizing ligand-binding domain is FKBP12 (SEQ ID NO: 1), and the second multimerizing ligand-binding domain is a variant of FRB having at least 80, such as at least 85, at least 90, at least 95, at least 98 or at least 99%, sequence identity with FRB (SEQ ID NO: 2).

According to other particular embodiments, the first multimerizing ligand-binding domain is a variant of FKBP12 having at least 80, such as at least 85, at least 90, at least 95, at least 98 or at least 99%, sequence identity with FKBP12 (SEQ ID NO: 1), and the second multimerizing ligand-binding domain is FRB (SEQ ID NO: 2).

According to other more particular embodiments, the first multimerizing ligand-binding domain is a variant of FKBP12 having at least 80, such as at least 85, at least 90, at least 95, at least 98 or at least 99%, sequence identity with FKBP12 (SEQ ID NO: 1), and the second multimerizing ligand-binding domain is a variant of FRB having at least 80, such as at least 85, at least 90, at least 95, at least 98 or at least 99%, sequence identity with FRB (SEQ ID NO: 2).

A variant of FKBP12 may differ from FKBP12 (SEQ ID NO: 1) in the substitution of one or more (such as 1 to 10, 1 to 5, or 1 to 3) amino acid residue(s). Alternatively, or in addition, such variant may differ from FKBP12 (SEQ ID NO: 1) in the addition or deletion of one or more (such as 1 to 10, 1 to 5, or 1 to 3) amino acid residue(s).

Suitably, a variant of FKBP12 is capable of binding to rapamycin or a rapalog, such as AP21967, AP23573, RAD001 or CCI-779. More specifically, such variant comprises a rapamycin or rapalog binding sequence.

A non-limiting example of a FKBP12 variant is one which contains a single amino acid substitution (F36V) as shown in SEQ ID NO: 3. Such variant of FKBP12 may for example be used as first and second multimerizing ligand-binding domains, forming a homodimer upon binding of the dimerizer AP1903.

Hence, according to certain embodiments, the first multimerizing ligand-binding domain is FKBP12(F36V) having the amino acid sequence as set forth in SEQ ID NO: 3 and the second multimerizing ligand-binding domain is FKBP12 (F36V) having the amino acid sequence as set forth in SEQ ID NO: 3.

A variant of FRB may differ from FRB (SEQ ID NO: 2) in the substitution of one or more (such as 1 to 10, 1 to 5, or 1 to 3) amino acid residue(s). Alternatively, or in addition, such variant may differ from FRB (SEQ ID NO: 2) in the addition or deletion of one or more (such as 1 to 10, 1 to 5, or 1 to 3) amino acid residue(s).

Suitably, a variant of FRB is capable of binding to rapamycin or a rapalog, such as AP21967, AP23573, RAD001 or CCI-779. More specifically, such variant comprises a rapamycin or rapalog binding sequence.

Non-limiting examples of FRB variants include ones which contain one or more amino acid substitution at the amino acid positions selected from L2031, E2032, S2035, R2036, F2039, G2040, T2098, W2101, D2102, Y2105, and F2108. According to certain embodiments, a variant of FRB comprises an amino acid substitution at T2098, where T2098 is replaced by leucine (T2098L), e.g., SEQ ID NO: 4, or phenylalanine (T2098F). According to certain other embodiments, a variant of FRB comprises an amino acid substitution at E2032, where E2032 is replaced by phenylalanine (E2032F), methionine (E2032M), arginine (E2032R), valine (E2032V), tyrosine (E2032Y), isoleucine (E2032I) or leucine (E2032L). According to certain other embodiments, a variant of FRB comprises an amino acid substitution at E2032 and at T2098, where E2032 is replaced by any amino acid, and where T2098 is replaced by any amino acid. According to certain other embodiments, a variant of FRB comprises an E2032I and a T2098L substitution. According to certain other embodiments, a variant of FRB comprises an E2032L and a T2098L substitution.

A variant of FRB having the T2098L substitution may for example be used as second multimerizing ligand-binding domain, forming a heterodimer with FKBP12 or variant thereof upon binding of the dimerizer AP21967. Hence, according to certain embodiments, the first multimerizing ligand-binding domain is FKBP12 (SEQ ID NO: 1), and the second multimerizing ligand-binding domain is a variant of FRB comprising an amino acid substitution at T2098, where T2098 is replaced by leucine (SEQ ID NO: 4).

According to certain embodiments, the first multimerizing ligand-binding domain is FKBP12 (SEQ ID NO: 1) or a variant thereof having at least 80, such as at least 85, at least 90, at least 95, at least 98 or at least 99%, sequence identity with FKBP12 (SEQ ID NO: 1), and the second multimerizing ligand-binding domain is Calcineurin A (CnA) (SEQ ID NO: 5) or a variant thereof having at least 80, such as at least 85, at least 90, at least 95, at least 98 or at least 99%, sequence identity with CnA (SEQ ID NO: 5).

According to certain embodiments, the first multimerizing ligand-binding domain is FKBP12 (SEQ ID NO: 1), and the second multimerizing ligand-binding domain is Calcineurin A (CnA) (SEQ ID NO: 5) or a variant thereof having at least 80, such as at least 85, at least 90, at least 95, at least 98 or at least 99%, sequence identity with CnA (SEQ ID NO: 5).

According to certain embodiments, the first multimerizing ligand-binding domain is a variant of FKBP12 having at least 80, such as at least 85, at least 90, at least 95, at least 98 or at least 99%, sequence identity with FKBP12 (SEQ ID NO: 1), and the second multimerizing ligand-binding domain is Calcineurin A (CnA) (SEQ ID NO: 5) or a variant thereof having at least 80, such as at least 85, at least 90, at least 95, at least 98 or at least 99%, sequence identity with CnA (SEQ ID NO: 5).

According to certain embodiments, the first multimerizing ligand-binding domain is FKBP12 (SEQ ID NO: 1), and the second multimerizing ligand-binding domain is Calcineurin A (CnA) (SEQ ID NO: 5).

According to certain embodiments, the first multimerizing ligand-binding domain is FKBP12 (SEQ ID NO: 1), and the second multimerizing ligand-binding domain is a variant of Calcineurin A (CnA) having at least 80, such as at least 85, at least 90, at least 95, at least 98 or at least 99%, sequence identity with CnA (SEQ ID NO: 5).

A variant of Calcineurin A (CnA) may differ from CnA (SEQ ID NO: 5) in the substitution of one or more (such as 1 to 10, 1 to 5, or 1 to 3) amino acid residue(s). Alternatively, or in addition, such variant may differ from CnA (SEQ ID NO: 5) in the addition or deletion of one or more (such as 1 to 10, 1 to 5, or 1 to 3) amino acid residue(s). Suitably, a variant of CnA is capable of binding to FK506. More specifically, such variant comprises a FK506 binding sequence.

According to certain embodiments, the first multimerizing ligand-binding domain is FKBP12 (SEQ ID NO: 1) or a variant thereof having at least 80, such as at least 85, at least 90, at least 95, at least 98 or at least 99%, sequence identity with FKBP12 (SEQ ID NO: 1), and the second multimerizing ligand-binding domain is Cyclophilin (CyP) (SEQ ID NO: 6) or a variant thereof having at least 80, such as at least 85, at least 90, at least 95, at least 98 or at least 99%, sequence identity with CyP (SEQ ID NO: 6).

According to certain embodiments, the first multimerizing ligand-binding domain is FKBP12 (SEQ ID NO: 1), and the second multimerizing ligand-binding domain is Cyclophilin (CyP) (SEQ ID NO: 6) or a variant thereof having at least 80, such as at least 85, at least 90, at least 95, at least 98 or at least 99%, sequence identity with CyP (SEQ ID NO: 6).

According to certain embodiments, the first multimerizing ligand-binding domain is a variant of FKBP12 having at least 80, such as at least 85, at least 90, at least 95, at least 98 or at least 99%, sequence identity with FKBP12 (SEQ ID NO: 1), and the second multimerizing ligand-binding domain is Cyclophilin (CyP) (SEQ ID NO: 6) or a variant thereof having at least 80, such as at least 85, at least 90, at least 95, at least 98 or at least 99%, sequence identity with CyP (SEQ ID NO: 6).

According to certain embodiments, the first multimerizing ligand-binding domain is FKBP12 (SEQ ID NO: 1), and the second multimerizing ligand-binding domain is Cyclophilin (CyP) (SEQ ID NO: 6).

According to certain embodiments, the first multimerizing ligand-binding domain is FKBP12 (SEQ ID NO: 1), and the second multimerizing ligand-binding domain is a variant of Cyclophilin (CyP) having at least 80, such as at least 85, at least 90, at least 95, at least 98 or at least 99%, sequence identity with CyP (SEQ ID NO: 6).

A variant of Cyclophilin (CyP) may differ from CyP (SEQ ID NO: 6) in the substitution of one or more (such as 1 to 10, 1 to 5, or 1 to 3) amino acid residue(s). Alternatively, or in addition, such variant may differ from CyP (SEQ ID NO: 6) in the addition or deletion of one or more (such as 1 to 10, 1 to 5, or 1 to 3) amino acid residue(s). Suitably, a variant of CyP is capable of binding to FKCsA. More specifically, such variant comprises a FKCsA binding sequence.

According to certain embodiments, the first multimerizing ligand-binding domain and second multimerizing ligand-binding domain are selected from GyrB (SEQ ID NO: 7), a coumermycin binding fragment thereof, or variants thereof having at least 80, such as at least 85, at least 90, at least 95, at least 98 or at least 99%, sequence identity with GyrB (SEQ ID NO: 7) or the coumermycin binding fragment thereof.

According to certain embodiments, the first multimerizing ligand-binding domain is GyrB (HQ ID NO: 7), and the second multimerizing ligand-binding domain is selected from GyrB (SEQ ID NO: 7), a coumermycin binding fragment thereof, or variants thereof having at least 80, such as at least 85, at least 90, at least 95, at least 98 or at least 99%, sequence identity with GyrB (SEQ ID NO: 7) or the coumermycin binding fragment thereof.

According to certain embodiments, the first multimerizing ligand-binding domain is a coumermycin binding fragment of GyrB, and the second multimerizing ligand-binding domain is selected from GyrB (SEQ ID NO: 7), a coumermycin binding fragment thereof, or variants thereof having at least 80, such as at least 85, at least 90, at least 95, at least 98 or at least 99%, sequence identity with GyrB (SEQ ID NO: 7) or the coumermycin binding fragment thereof.

According to certain embodiments, the first multimerizing ligand-binding domain is GyrB (SEQ ID NO: 7) or a variant thereof having at least 80, such as at least 85, at least 90, at least 95, at least 98 or at least 99%, sequence identity with GyrB (SEQ ID NO: 7), and the second multimerizing ligand-binding domain is GyrB (SEQ ID NO: 7) or a variant thereof having at least 80, such as at least 85, at least 90, at least 95, at least 98 or at least 99%, sequence identity with GyrB (SEQ ID NO: 7).

According to particular embodiments, the first multimerizing ligand-binding domain is GyrB (SEQ ID NO: 7), and the second multimerizing ligand-binding domain is GyrB (SEQ ID NO: 7) or a variant thereof having at least 80, such as at least 85, at least 90, at least 95, at least 98 or at least 99%, sequence identity with GyrB (SEQ ID NO: 7).

According to other particular embodiments, the first multimerizing ligand-binding domain is a variant of GyrB having at least 80, such as at least 85, at least 90, at least 95, at least 98 or at least 99%, sequence identity with GyrB (SEQ ID NO: 7), and the second multimerizing ligand-binding domain is GyrB (SEQ ID NO: 7) or a variant thereof having at least 80, such as at least 85, at least 90, at least 95, at least 98 or at least 99%, sequence identity with GyrB (SEQ ID NO: 7).

According to more particular embodiments, the first multimerizing ligand-binding domain is GyrB, and the second multimerizing ligand-binding domain is GyrB (SEQ ID NO: 7).

According to other particular embodiments, the first multimerizing ligand-binding domain is GyrB (SEQ ID NO: 7), and the second multimerizing ligand-binding domain is a variant of GyrB having at least 80, such as at least 85, at least 90, at least 95, at least 98 or at least 99%, sequence identity with GyrB (SEQ ID NO: 7).

According to other more particular embodiments, the first multimerizing ligand-binding domain is a variant of GyrB having at least 80, such as at least 85, at least 90, at least 95, at least 98 or at least 99%, sequence identity with GyrB (SEQ ID NO: 7), and the second multimerizing ligand-binding domain is a variant of GyrB having at least 80, such as at least 85, at least 90, at least 95, at least 98 or at least 99%, sequence identity with GyrB (SEQ ID NO: 7).

According to certain embodiments, the first multimerizing ligand-binding domain is a coumermycin binding fragment of GyrB or a variant thereof having at least 80, such as at least 85, at least 90, at least 95, at least 98 or at least 99%, sequence identity with the coumermycin binding fragment of GyrB, and the second multimerizing ligand-binding domain is a coumermycin binding fragment of GyrB or a variant thereof having at least 80, such as at least 85, at least 90, at least 95, at least 98 or at least 99%, sequence identity with GyrB (SEQ ID NO: 7) or the coumermycin binding fragment thereof.

According to particular embodiments, the first multimerizing ligand-binding domain is a coumermycin binding fragment of GyrB, and the second multimerizing ligand-binding domain is a coumermycin binding fragment of GyrB or a variant thereof having at least 80, such as at least 85, at least 90, at least 95, at least 98 or at least 99%, sequence identity with the coumermycin binding fragment of GyrB.

According to other particular embodiments, the first multimerizing ligand-binding domain is a variant of a coumermycin binding fragment of GyrB having at least 80, such as at least 85, at least 90, at least 95, at least 98 or at least 99%, sequence identity with the coumermycin binding fragment of GyrB.

According to other particular embodiments, the first multimerizing ligand-binding domain is a coumermycin binding fragment of GyrB, and the second multimerizing ligand-binding domain is a coumermycin binding fragment of GyrB.

A variant of GyrB may differ from GyrB (SEQ ID NO: 7) in the substitution of one or more (such as 1 to 10, 1 to 5, or 1 to 3) amino acid residue(s). Alternatively, or in addition, such variant may differ from GyrB (SEQ ID NO: 7) in the addition or deletion of one or more (such as 1 to 10, 1 to 5, or 1 to 3) amino acid residue(s). Suitably, a variant of GyrB is capable of binding to coumermycin. More specifically, such variant comprises a coumermycin binding sequence.

A variant of a coumermycin binding fragment of GyrB may differ from a coumermycin binding fragment of GyrB in the substitution of one or more (such as 1 to 10, 1 to 5, or 1 to 3) amino acid residue(s). Alternatively, or in addition, such variant may differ from a coumermycin binding fragment of GyrB in the addition or deletion of one or more (such as 1 to 10, 1 to 5, or 1 to 3) amino acid residue(s). Suitably, such variant is capable of binding to coumermycin. More specifically, such variant comprises a coumermycin binding sequence.

A coumermycin binding fragment the may be used according to the present invention may be the 24 KDa amino terminal subdomain of GyrB.

According to certain embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is GID1A (SEQ ID NO: 9) or a variant thereof having at least 80, such as at least 85, at least 90, at least 95, at least 98 or at least 99%, sequence identity with GID1A (SEQ ID NO: 9).

According to particular embodiments, the first multimerizing ligand-binding domain is GAI (SEQ ID NO: 8), and the second multimerizing ligand-binding domain is GID1A (SEQ ID NO: 9) or a variant thereof having at least 80, such as at least 85, at least 90, at least 95, at least 98 or at least 99%, sequence identity with GID1A (SEQ ID NO: 9).

According to other particular embodiments, the first multimerizing ligand-binding domain is a variant of GAI having at least 80, such as at least 85, at least 90, at least 95, at least 98 or at least 99%, sequence identity with GAI (SEQ ID NO: 8), and the second multimerizing ligand-binding domain is GID1A (SEQ ID NO: 9) or a variant thereof having at least 80, such as at least 85, at least 90, at least 95, at least 98 or at least 99%, sequence identity with GID1A (SEQ ID NO: 9).

According to other particular embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 6), and the second multimerizing ligand-binding domain is GID1A (SEQ ID NO: 9).

According to other particular embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is a variant of GID1A having at least 80, such as at least 85, at least 90, at least 95, at least 98 or at least 99%, sequence identity with GID1A (SEQ ID NO: 9).

According to more particular embodiments, the first multimerizing ligand-binding domain is GAI (SEQ ID NO: 8), and the second multimerizing ligand-binding domain is GID1A (SEQ ID NO: 9).

According to other more particular embodiments, the first multimerizing ligand-binding domain is a variant of GAI having at least 80, such as at least 85, at least 90, at least 95, at least 98 or at least 99%, sequence identity with GAI (SEQ ID NO: 8), and the second multimerizing ligand-binding domain is a variant of GID1A having at least 80, such as at least 85, at least 90, at least 95, at least 98 or at least 99%, sequence identity with GID1A (SEQ ID NO: 9).

A variant of GAI may differ from GAI (SEQ ID NO: 8) in the substitution of one or more (such as 1 to 10, 1 to 5, or 1 to 3) amino acid residue(s). Alternatively, or in addition, such variant may differ from GAI (SEQ ID NO: 8) in the addition or deletion of one or more (such as 1 to 10, 1 to 5, or 1 to 3) amino acid residue(s). Suitably, a variant of GAI is capable of binding to gibberellin. More specifically, such variant comprises a gibberellin binding sequence.

A variant of GID1A may differ from GID1A (SEQ ID NO: 9) in the substitution of one or more (such as 1 to 10, 1 to 5, or 1 to 3) amino acid residue(s). Alternatively, or in addition, such variant may differ from GID1A (SEQ ID NO: 9) in the addition or deletion of one or more (such as 1 to 10, 1 to 5, or 1 to 3) amino acid residue(s). Suitably, a variant of GID1A is capable of binding to gibberellin. More specifically, such variant comprises a gibberellin binding sequence.

According to certain embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is GID1B (SEQ ID NO: 10) or a variant thereof having at least 80, such as at least 85, at least 90, at least 95, at least 98 or at least 99%, sequence identity with GID1B (SEQ ID NO: 10).

According to particular embodiments, the first multimerizing ligand-binding domain is GAI (SEQ ID NO: 8), and the second multimerizing ligand-binding domain is GID1B (SEQ ID NO: 10) or a variant thereof having at least 80, such as at least 85, at least 90, at least 95, at least 98 or at least 99%, sequence identity with GID1B (SEQ ID NO: 10).

According to other particular embodiments, the first multimerizing ligand-binding domain is a variant of GAI having at least 80, such as at least 85, at least 90, at least 95, at least 98 or at least 99%, sequence identity with GAI (SEQ ID NO: 8), and the second multimerizing ligand-binding domain is GID1B (SEQ ID NO: 10) or a variant thereof having at least 80, such as at least 85, at least 90, at least 95, at least 98 or at least 99%, sequence identity with GID1B (SEQ ID NO: 10).

According to other particular embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is GID1B (SEQ ID NO: 10).

According to other particular embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is a variant of GID1B having at least 80, such as at least 85, at least 90, at least 95, at least 98 or at least 99%, sequence identity with GID1B (SEQ ID NO: 10).

According to more particular embodiments, the first multimerizing ligand-binding domain is GAI (SEQ ID NO: 8), and the second multimerizing ligand-binding domain is GID1B (SEQ ID NO: 10).

According to other more particular embodiments, the first multimerizing ligand-binding domain is a variant of GAI having at least 80, such as at least 85, at least 90, at least 95, at least 98 or at least 99%, sequence identity with GAI (SEQ ID NO: 8), and the second multimerizing ligand-binding domain is a variant of GID1B having at least 80, such as at least 85, at least 90, at least 95, at least 98 or at least 99%, sequence identity with GID1B (SEQ ID NO: 10).

A variant of GID1B may differ from GID1B (SEQ ID NO: 10) in the substitution of one or more (such as 1 to 10, 1 to 5, or 1 to 3) amino acid residue(s). Alternatively, or in addition, such variant may differ from GID1B (SEQ ID NO: 10) in the addition or deletion of one or more (such as 1 to 10, 1 to 5, or 1 to 3) amino acid residue(s). Suitably, a variant of GID1B is capable of binding to gibberellin. More specifically, such variant comprises a gibberellin binding sequence.

According to certain embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is GID1C (SEQ ID NO: 11) or a variant thereof having at least 80, such as at least 85, at least 90, at least 95, at least 98 or at least 99%, sequence identity with GID1C (SEQ ID NO: 11).

According to particular embodiments, the first multimerizing ligand-binding domain is GAI (SEQ ID NO: 8), and the second multimerizing ligand-binding domain is GID1C (SEQ ID NO: 11) or a variant thereof having at least 80, such as at least 85, at least 90, at least 95, at least 98 or at least 99%, sequence identity with GID1C (SEQ ID NO: 11).

According to other particular embodiments, the first multimerizing ligand-binding domain is a variant of GAI having at least 80, such as at least 85, at least 90, at least 95, at least 98 or at least 99%, sequence identity with GAI (SEQ ID NO: 8), and the second multimerizing ligand-binding domain is GID1C (SEQ ID NO: 11) or a variant thereof having at least 80, such as at least 85, at least 90, at least 95, at least 98 or at least 99%, sequence identity with GID1C (SEQ ID NO: 11).

According to other particular embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is GID1C (SEQ ID NO: 11).

According to other particular embodiments, the first multimerizing ligand-binding domain is GAI (SEQ ID NO: 8) or a variant thereof having at least 80, such as at least 85, at least 90, at least 95, at least 98 or at least 99%, sequence identity with GAI (SEQ ID NO: 8), and the second multimerizing ligand-binding domain is a variant of GID1C having at least 80, such as at least 85, at least 90, at least 95, at least 98 or at least 99%, sequence identity with GID1C (SEQ ID NO: 11).

According to more particular embodiments, the first multimerizing ligand-binding domain is GAI (SEQ ID NO: 8), and the second multimerizing ligand-binding domain is GID1C (SEQ ID NO: 11).

According to other more particular embodiments, the first multimerizing ligand-binding domain is a variant of GAI having at least 80, such as at least 85, at least 90, at least 95, at least 98 or at least 99%, sequence identity with GAI (SEQ ID NO: 8), and the second multimerizing ligand-binding domain is a variant of GID1C having at least 80, such as at least 85, at least 90, at least 95, at least 98 or at least 99%, sequence identity with GID1C (SEQ ID NO: 11).

A variant of GID1C may differ from GID1C (SEQ ID NO: 11) in the substitution of one or more (such as 1 to 10, 1 to 5, or 1 to 3) amino acid residue(s). Alternatively, or in addition, such variant may differ from GID1C (SEQ ID NO: 11) in the addition or deletion of one or more (such as 1 to 10, 1 to 5, or 1 to 3) amino acid residue(s). Suitably, a variant of GID1C is capable of binding to gibberellin. More specifically, such variant comprises a gibberellin binding sequence.

According to certain embodiments, the first multimerizing ligand-binding domain is Snap-tag (SEQ ID NO: 12) or a variant thereof having at least 80, such as at least 85, at least 90, at least 95, at least 98 or at least 99%, sequence identity with Snap-tag (SEQ ID NO: 12), and the second multimerizing ligand-binding domain is Halo-tag (SEQ ID NO: 13) or a variant thereof having at least 80, such as at least 85, at least 90, at least 95, at least 98 or at least 99%, sequence identity with Halo-tag (SEQ ID NO: 13).

According to particular embodiments, the first multimerizing ligand-binding domain is Snap-tag (SEQ ID NO: 12), and the second multimerizing ligand-binding domain is Halo-tag (SEQ ID NO: 13) or a variant thereof having at least 80, such as at least 85, at least 90, at least 95, at least 98 or at least 99%, sequence identity with Halo-tag (SEQ ID NO: 13).

According to other particular embodiments, the first multimerizing ligand-binding domain is a variant of Snap-tag having at least 80, such as at least 85, at least 90, at least 95, at least 98 or at least 99%, sequence identity with Snap-tag (SEQ ID NO: 12), and the second multimerizing ligand-binding domain is Halo-tag (SEQ ID NO: 13) or a variant thereof having at least 80, such as at least 85, at least 90, at least 95, at least 98 or at least 99%, sequence identity with Halo-tag (SEQ ID NO: 13).

According to other particular embodiments, the first multimerizing ligand-binding domain is Snap-tag (SEQ ID NO: 12) or a variant thereof having at least 80, such as at least 85, at least 90, at least 95, at least 98 or at least 99%, sequence identity with Snap-tag (SEQ ID NO: 12), and the second multimerizing ligand-binding domain is Halo-tag (SEQ ID NO: 13).

According to other particular embodiments, the first multimerizing ligand-binding domain is Snap-tag (SEQ ID NO: 12) or a variant thereof having at least 80, such as at least 85, at least 90, at least 95, at least 98 or at least 99%, sequence identity with Snap-tag (SEQ ID NO: 12), and the second multimerizing ligand-binding domain is a variant of Halo-tag having at least 80, such as at least 85, at least 90, at least 95, at least 98 or at least 99%, sequence identity with Halo-tag (SEQ ID NO: 13).

According to more particular embodiments, the first multimerizing ligand-binding domain is Snap-tag (SEQ ID NO: 12), and the second multimerizing ligand-binding domain is Halo-tag (SEQ ID NO: 13).

According to other more particular embodiments, the first multimerizing ligand-binding domain is a variant of Snap-tag having at least 80, such as at least 85, at least 90, at least 95, at least 98 or at least 99%, sequence identity with Snap-tag (SEQ ID NO: 12), and the second multimerizing ligand-binding domain is a variant of Halo-tag having at least 80, such as at least 85, at least 90, at least 95, at least 98 or at least 99%, sequence identity with Halo-tag (SEQ ID NO: 13).

A variant of Snap-tag may differ from Snap-tag (SEQ ID NO: 12) in the substitution of one or more (such as 1 to 10, 1 to 5, or 1 to 3) amino acid residue(s). Alternatively, or in addition, such variant may differ from Snap-tag (SEQ ID NO: 12) in the addition or deletion of one or more (such as 1 to 10, 1 to 5, or 1 to 3) amino acid residue(s). Suitably, a variant of Snap-tag is capable of binding to HaXs. More specifically, such variant comprises a HaXs binding sequence.

A variant of Halo-tag may differ from Halo-tag (SEQ ID NO: 13) in the substitution of one or more (such as 1 to 10, 1 to 5, or 1 to 3) amino acid residue(s). Alternatively, or in addition, such variant may differ from Halo-tag (SEQ ID NO: 13) in the addition or deletion of one or more (such as 1 to 10, 1 to 5, or 1 to 3) amino acid residue(s). Suitably, a variant of Halo-tag is capable of binding to HaXs. More specifically, such variant comprises a HaXs binding sequence.

According to certain embodiments, the first multimerizing ligand-binding domain is Snap-tag (SEQ ID NO: 12) or a variant thereof having at least 80, such as at least 85, at least 90, at least 95, at least 98 or at least 99%, sequence identity with Snap-tag (SEQ ID NO: 12), and the second multimerizing ligand-binding domain is CLIP-tag (SEQ ID NO: 14) or a variant thereof having at least 80, such as at least 85, at least 90, at least 95, at least 98 or at least 99%, sequence identity with CLIP-tag (SEQ ID NO: 14).

According to particular embodiments, the first multimerizing ligand-binding domain is Snap-tag (SEQ ID NO: 12), and the second multimerizing ligand-binding domain is CLIP-tag (SEQ ID NO: 14) or a variant thereof having at least 80, such as at least 85, at least 90, at least 95, at least 98 or at least 99%, sequence identity with CLIP-tag (SEQ ID NO: 14).

According to other particular embodiments, the first multimerizing ligand-binding domain is a variant of Snap-tag having at least 80, such as at least 85, at least 90, at least 95, at least 98 or at least 99%, sequence identity with Snap-tag (SEQ ID NO: 12), and the second multimerizing ligand-binding domain is CLIP-tag (SEQ ID NO: 14) or a variant thereof having at least 80, such as at least 85, at least 90, at least 95, at least 98 or at least 99%, sequence identity with CLIP-tag (SEQ ID NO: 14).

According to other particular embodiments, the first multimerizing ligand-binding domain is Snap-tag (SEQ ID NO: 12) or a variant thereof having at least 80, such as at least 85, at least 90, at least 95, at least 98 or at least 99%, sequence identity with Snap-tag (SEQ ID NO: 12), and the second multimerizing ligand-binding domain is CLIP-tag (SEQ ID NO: 14).

According to other particular embodiments, the first multimerizing ligand-binding domain is Snap-tag (SEQ ID NO: 12) or a variant thereof having at least 80, such as at least 85, at least 90, at least 95, at least 98 or at least 99%, sequence identity with Snap-tag (SEQ ID NO: 12), and the second multimerizing ligand-binding domain is a variant of CLIP-tag having at least 80, such as at least 85, at least 90, at least 95, at least 98 or at least 99%, sequence identity with CLIP-tag (SEQ ID NO: 14).

According to more particular embodiments, the first multimerizing ligand-binding domain is Snap-tag (SEQ ID NO: 12), and the second multimerizing ligand-binding domain is CLIP-tag (SEQ ID NO: 14).

According to other more particular embodiments, the first multimerizing ligand-binding domain is a variant of Snap-tag having at least 80, such as at least 85, at least 90, at least 95, at least 98 or at least 99%, sequence identity with Snap-tag (SEQ ID NO: 12), and the second multimerizing ligand-binding domain is a variant of CLIP-tag having at least 80, such as at least 85, at least 90, at least 95, at least 98 or at least 99%, sequence identity with CLIP-tag (SEQ ID NO: 14).

A variant of CLIP-tag may differ from CLIP-tag (SEQ ID NO: 14) in the substitution of one or more (such as 1 to 10, 1 to 5, or 1 to 3) amino acid residue(s). Alternatively, or in addition, such variant may differ from CLIP-tag (SEQ ID NO: 14) in the addition or deletion of one or more (such as 1 to 10, 1 to 5, or 1 to 3) amino acid residue(s). Suitably, a variant of CLIP-tag is capable of binding to SC. More specifically, such variant comprises a SC binding sequence.

According to certain embodiments, the first multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15), and the second multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15).

According to particular embodiments, the first multimerizing ligand-binding domain is DHFR (SEQ ID NO: 15), and the second multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15).

According to other particular embodiments, the first multimerizing ligand-binding domain is a variant of DHFR having at least 80, such as at least 85, at least 90, at least 95, at least 98 or at least 99%, sequence identity with DHFR (SEQ ID NO: 15), and the second multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15).

According to other particular embodiments, the first multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15), and the second multimerizing ligand-binding domain is DHFR (SEQ ID NO: 15).

According to other particular embodiments, the first multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15), and the second multimerizing ligand-binding domain is a variant of DHFR having at least 80, such as at least 85, at least 90, at least 95, at least 98 or at least 99%, sequence identity with DHFR (SEQ ID NO: 15).

According to more particular embodiments, the first multimerizing ligand-binding domain is DHFR (SEQ ID NO: 15), and the second multimerizing ligand-binding domain is DHFR (SEQ ID NO: 15).

According to other more particular embodiments, the first multimerizing ligand-binding domain is a variant of DHFR having at least 80, such as at least 85, at least 90, at least 95, at least 98 or at least 99%, sequence identity with DHFR (SEQ ID NO: 15), and the second multimerizing ligand-binding domain is a variant of DHFR having at least 80, such as at least 85, at least 90, at least 95, at least 98 or at least 99%, sequence identity with DHFR (SEQ ID NO: 15).

A variant of DHFR may differ from DHFR (SEQ ID NO: 15) in the substitution of one or more (such as 1 to 10, 1 to 5, or 1 to 3) amino acid residue(s). Alternatively, or in addition, such variant may differ from DHFR (SEQ ID NO: 15) in the addition or deletion of one or more (such as 1 to 10, 1 to 5, or 1 to 3) amino acid residue(s). Suitably, a variant of DHFR is capable of binding to BisMTX. More specifically, such variant comprises a BisMTX binding sequence.

According to certain embodiments, the first multimerizing ligand-binding domain is a glucocorticoid receptor ligand-binding domain (SEQ ID NO: 16) or a variant thereof having at least 80, such as at least 85, at least 90, at least 95, at least 98 or at least 99%, sequence identity with said glucocorticoid receptor ligand-binding domain (SEQ ID NO: 16), and the second multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15).

According to particular embodiments, the first multimerizing ligand-binding domain is a glucocorticoid receptor ligand-binding domain (SEQ ID NO: 16), and the second multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15).

According to other particular embodiments, the first multimerizing ligand-binding domain is a variant of a glucocorticoid receptor ligand-binding domain having at least 80, such as at least 85, at least 90, at least 95, at least 98 or at least 99%, sequence identity with a glucocorticoid receptor ligand-binding domain (SEQ ID NO: 16), and the second multimerizing ligand-binding domain is DHFR (SEQ ID NO: 15) or a variant thereof having at least 80, such as at least 85, at least 90, at least 95, at least 98 or at least 99%, sequence identity with DHFR (SEQ ID NO: 15).

According to other particular embodiments, the first multimerizing ligand-binding domain is a glucocorticoid receptor ligand-binding domain (SEQ ID NO: 16) or a variant thereof having at least 80, such as at least 85, at least 90, at least 95, at least 98 or at least 99%, sequence identity with said glucocorticoid receptor ligand-binding domain (SEQ ID NO: 16), and the second multimerizing ligand-binding domain is DHFR (SEQ ID NO: 15).

According to other particular embodiments, the first multimerizing ligand-binding domain is a glucocorticoid receptor ligand-binding domain (SEQ ID NO: 16) or a variant thereof having at least 80, such as at least 85, at least 90, at least 95, at least 98 or at least 99%, sequence identity with said glucocorticoid receptor ligand-binding domain (SEQ ID NO: 16), and the second multimerizing ligand-binding domain is a variant of DHFR having at least 80, such as at least 85, at least 90, at least 95, at least 98 or at least 99%, sequence identity with DHFR (SEQ ID NO: 15).

According to more particular embodiments, the first multimerizing ligand-binding domain is a glucocorticoid receptor ligand-binding domain (SEQ ID NO: 16), and the second multimerizing ligand-binding domain is DHFR (SEQ ID NO: 15).

According to other more particular embodiments, the first multimerizing ligand-binding domain is a variant of a glucocorticoid receptor ligand-binding domain having at least 80, such as at least 85, at least 90, at least 95, at least 98 or at least 99%, sequence identity with a glucocorticoid receptor ligand-binding domain (SEQ ID NO: 16), and the second multimerizing ligand-binding domain is a variant of DHFR having at least 80, such as at least 85, at least 90, at least 95, at least 98 or at least 99%, sequence identity with DHFR (SEQ ID NO: 15).

A variant of a glucocorticoid receptor ligand-binding domain (SEQ ID NO: 16) may differ from said glucocorticoid receptor ligand-binding domain (SEQ ID NO: 16) in the substitution of one or more (such as 1 to 10, 1 to 5, or 1 to 3) amino acid residue(s). Alternatively, or in addition, such variant may differ from DHFR (SEQ ID NO: 15) in the addition or deletion of one or more (such as 1 to 10, 1 to 5, or 1 to 3) amino acid residue(s). Suitably, a variant of said glucocorticoid receptor ligand-binding domain (SEQ ID NO: 16) is capable of binding to Dex-Mtx or Dex-TMP. More specifically, such variant comprises a Dex-Mtx or Dex-TMP binding sequence.

According to certain embodiments, the first multimerizing ligand-binding domain is PYL1 (SEQ ID NO: 17) or a variant thereof having at least 80, such as at least 85, at least 90, at least 95, at least 98 or at least 99%, sequence identity with PYL1 (SEQ ID NO: 17), and the second multimerizing ligand-binding domain is ABI1 (SEQ ID NO: 18) or a variant thereof having at least 80, such as at least 85, at least 90, at least 95, at least 98 or at least 99%, sequence identity with ABI1 (SEQ ID NO: 18).

According to particular embodiments, the first multimerizing ligand-binding domain is PYL1 (SEQ ID NO: 17), and the second multimerizing ligand-binding domain is ABI1 (SEQ ID NO: 18) or a variant thereof having at least 80, such as at least 85, at least 90, at least 95, at least 98 or at least 99%, sequence identity with ABI1 (SEQ ID NO: 18).

According to other particular embodiments, the first multimerizing ligand-binding domain is a variant of PYL1 having at least 80, such as at least 85, at least 90, at least 95, at least 98 or at least 99%, sequence identity with PYL1 (SEQ ID NO: 17), and the second multimerizing ligand-binding domain is ABI1 (SEQ ID NO: 18) or a variant thereof having at least 80, such as at least 85, at least 90, at least 95, at least 98 or at least 99%, sequence identity with ABI1 (SEQ ID NO: 18).

According to other particular embodiments, the first multimerizing ligand-binding domain is PYL1 (SEQ ID NO: 17) or a variant thereof having at least 80, such as at least 85, at least 90, at least 95, at least 98 or at least 99%, sequence identity with PYL1 (SEQ ID NO: 17), and the second multimerizing ligand-binding domain is ABI1 (SEQ ID NO: 18).

According to other particular embodiments, the first multimerizing ligand-binding domain is PYL1 (SEQ ID NO: 17) or a variant thereof having at least 80, such as at least 85, at least 90, at least 95, at least 98 or at least 99%, sequence identity with PYL1 (SEQ ID NO: 17), and the second multimerizing ligand-binding domain is a variant of ABI1 having at least 80, such as at least 85, at least 90, at least 95, at least 98 or at least 99%, sequence identity with ABI1 (SEQ ID NO: 18).

According to more particular embodiments, the first multimerizing ligand-binding domain is PYL1 (SEQ ID NO: 17), and the second multimerizing ligand-binding domain is ABI1 (SEQ ID NO: 18).

According to other more particular embodiments, the first multimerizing ligand-binding domain is a variant of PYL1 having at least 80, such as at least 85, at least 90, at least 95, at least 98 or at least 99%, sequence identity with PYL1 (SEQ ID NO: 17), and the second multimerizing ligand-binding domain is a variant of ABI1 having at least 80, such as at least 85, at least 90, at least 95, at least 98 or at least 99%, sequence identity with ABI1 (SEQ ID NO: 18).

A variant of PYL1 may differ from PYL1 (SEQ ID NO: 17) in the substitution of one or more (such as 1 to 10, 1 to 5, or 1 to 3) amino acid residue(s). Alternatively, or in addition, such variant may differ from PYL1 (SEQ ID NO: 17) in the addition or deletion of one or more (such as 1 to 10, 1 to 5, or 1 to 3) amino acid residue(s). Suitably, a variant of PYL1 is capable of binding to S-(+)-abscisic acid (ABA). More specifically, such variant comprises a S-(+)-abscisic acid (ABA) binding sequence.

A variant of ABI1 may differ from ABI1 (SEQ ID NO: 18) in the substitution of one or more (such as 1 to 10, 1 to 5, or 1 to 3) amino acid residue(s). Alternatively, or in addition, such variant may differ from ABI1 (SEQ ID NO: 18) in the addition or deletion of one or more (such as 1 to 10, 1 to 5, or 1 to 3) amino acid residue(s). Suitably, a variant of ABI1 is capable of binding to S-(+)-abscisic acid (ABA). More specifically, such variant comprises a S-(+)-abscisic acid (ABA) binding sequence.

The first and second multimerizing ligand-binding domains may either be directly fused to each other or may be separated by a peptide linker.

Thus, according to certain embodiments, are separated by a peptide linker. The peptide linker may be composed of up to 50 amino acids, such as up to 25 amino acids. According to certain embodiments, the peptide linker is composed of 5 to 25 amino acids. Non-limiting examples of peptide linkers that may be employed according to the invention include a four-EAAAR-linker (SEQ ID NO: 19), a –GS-4x-EAAAR-linker (SEQ ID NO: 20) and variants thereof. Thus, according to particular embodiments, the peptide linker is a four-EAAAR-linker (SEQ ID NO: 19) or a variant thereof having at least 80, such as at least 85, at least 90, at least 95, at least 98 or at least 99%, sequence identity with the four-EAAAR-linker (SEQ ID NO: 19). According to other particular embodiments, the peptide linker is a –GS-4x-EAAAR-linker (SEQ ID NO: 20) or a variant thereof having at least 80, such as at least 85, at least 90, at least 95, at least 98 or at least 99%, sequence identity with the –GS-4x-EAAAR-linker (SEQ ID NO: 20).

According to certain other embodiments, the first and second multimerizing ligand-binding domains are in direct fusion (e.g., the C-terminus of the first multimerizing ligand-binding domain is in direct fusion with the N-terminus of the second multimerizing ligand-binding domain). With "direct fusion" it is meant that there is no peptide linker between the first and second multimerizing ligand-binding domains, that is the two domains are linked by a carbon-nitrogen bond.

The first and second multimerizing ligand-binding domains may be arranged in any possible order, that is the first multimerizing ligand-binding domain may be located N-terminal to the second multimerizing ligand-binding domain, or the first multimerizing ligand-binding domain may be located C-terminal to the second multimerizing ligand-binding domain. Thus, according to certain embodiments, the first multimerizing ligand-binding domain is located N-terminal to the second multimerizing ligand-binding domain. According to other certain embodiments, the first multimerizing ligand-binding domain is located C-terminal to the second multimerizing ligand-binding domain.

A chimeric antigen receptor according to the present invention may further comprise a hinge within the at least one ectodomain. The hinge is suitably located between the switch domain and the transmembrane domain.

The term "hinge" or "hinge region" used herein generally means any oligo- or polypeptide that functions to link the transmembrane domain to the switch domain. In particular, a hinge is used to provide more flexibility and accessibility for the extracellular ligand-binding domain. A hinge region may comprise up to 300 amino acids, preferably 10 to 100 amino acids and most preferably 25 to 50 amino acids. A hinge may be derived from all or part of naturally occurring molecules, such as from all or part of the extracellular region of CD8, CD4 or CD28, or from all or part of an antibody constant region. Alternatively the hinge may be a synthetic sequence that corresponds to a naturally occurring hinge sequence, or may be an entirely synthetic hinge sequence. Non-limiting examples of hinges which may be used in accordance to the invention include a part of human CD8 alpha chain, FcγRIIIα receptor or IgG1.

According to certain embodiments, the hinge is selected from the group consisting of CD8a hinge, IgG1 hinge and FcγRIIIα hinge.

According to particular embodiments, the hinge is a CD8a hinge (SEQ ID NO: 21) or a variant thereof having at least 80, such as at least 85, at least 90, at least 95, at least 98 or at least 99%, sequence identity with the CD8a hinge (SEQ ID NO: 21). According to more particular embodiments, the hinge is a CD8a hinge (SEQ ID NO: 21). According to other more particular embodiment, the hinge is a variant of a CD8a hinge having at least 80, such as at least 85, at least 90, at least 95, at least 98 or at least 99%, sequence identity with the CD8a hinge (SEQ ID NO: 21). A variant of a CD8a hinge may differ from said CD8a hinge in the substitution of one or more (such 1 to 10, 1 to 5, or 1 to 3) amino acid residue(s). Alternatively, or in addition, such variant may differ from said CD8a hinge in the addition or deletion of one or more (such 1 to 10, 1 to 5, or 1 to 3) amino acid residue(s).

According to other particular embodiments, the hinge is a IgG1 hinge (SEQ ID NO: 22) or a variant thereof having at least 80, such as at least 85, at least 90, at least 95, at least 98 or at least 99%, sequence identity with the IgG1 hinge (SEQ ID NO: 22). According to more particular embodiments, the hinge is a IgG1 hinge (SEQ ID NO: 22). According to other more particular embodiment, the hinge is a variant of a IgG1 hinge having at least 80, such as at least 85, at least 90, at least 95, at least 98 or at least 99%, sequence identity with the IgG1 hinge (SEQ ID NO: 22). A variant of a IgG1 hinge may differ from said IgG1 hinge in the substitution of one or more (such 1 to 10, 1 to 5, or 1 to 3) amino acid residue(s). Alternatively, or in addition, such variant may differ from said IgG1 hinge in the addition or deletion of one or more (such 1 to 10, 1 to 5, or 1 to 3) amino acid residue(s).

According to other particular embodiments, the hinge is a FcγRIIIα hinge (SEQ ID NO: 23) or a variant thereof having at least 80, such as at least 85, at least 90, at least 95, at least 98 or at least 99%, sequence identity with the FcγRIIIα hinge (SEQ ID NO: 23). According to more particular embodiments, the hinge is a FcγRIIIα hinge (SEQ ID NO: 23). According to other more particular embodiment, the hinge is a variant of a FcγRIIIα hinge having at least 80, such as at least 85, at least 90, at least 95, at least 98 or at least 99%, sequence identity with the FcγRIIIα hinge (SEQ ID NO: 23). A variant of a FcγRIIIα hinge may differ from said FcγRIIIα hinge in the substitution of one or more (such 1 to 10, 1 to 5, or 1 to 3) amino acid residue(s). Alternatively, or in addition, such variant may differ from said FcγRIIIα hinge in the addition or deletion of one or more (such 1 to 10, 1 to 5, or 1 to 3) amino acid residue(s).

The "extracellular antigen binding domain" comprised by the ectodomain of the chimeric antigen receptor may be any oligo- or polypeptide that is capable of binding a ligand, more specifically an antigen. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells. In particular, the extracellular ligand-binding domain can comprise an antigen binding fragment derived from an antibody against an antigen of the target.

Thus, according to certain embodiments, the extracellular antigen binding domain comprises an antibody or antigen binding fragment thereof. The antigen binding fragment may be, for example, a scFv or a Fab.

According to particular embodiments, the extracellular antigen binding domain is a scFv, preferably one derived from a monoclonal antibody against an antigen of a target. More specifically, the extracellular ligand-binding domain may comprise a single chain antibody fragment (scFv) comprising the light (VL) and the heavy (VH) variable fragment of a target antigen specific monoclonal antibody, optionally joined by a peptide linker composed of, e.g., 5 to 25 amino acids (such as a GGGGSGGGGSGGGGS-linker as shown in SEQ ID NO: 24).

According to other particular embodiments, the extracellular antigen binding domain is a Fab, preferably one derived from a monoclonal antibody against an antigen of a target.

As non-limiting examples, the antigen of the target can be any cluster of differentiation molecules (e.g. CD16, CD64, CD78, CD96, CLL1, CD116, CD117, CD71, CD45, CD71, CD123 and CD138), a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), or a virus-specific surface antigen such as an HIV-specific antigen (such as HIV gp120); an HBV-specific antigen, an EBV-specific antigen, a CMV-specific antigen, a HPV-specific antigen, a Lasse Virus-specific antigen, an Influenza Virus-specific antigen, a fungi-specific antigen or a bacterium-specific antigen as well as any derivate or variant of these surface markers. Antigens are not necessarily surface marker antigens but can be also endogenous small antigens presented by HLA class I at the surface of the cells.

According to certain embodiments, the extracellular antigen binding domain may be directed against CD19. Such extracellular antigen binding domain may be a scFV derived from a CD19 monoclonal antibody, such as 4G7 (Peipp, Saul et al., 2004). According to particular embodiments, said scFV comprises the variable fragments of the CD19 monoclonal antibody 4G7 immunoglobulin gamma 1 heavy chain (SEQ ID NO: 25) and the variable fragments of the CD19 monoclonal antibody 4G7 immunoglobulin kappa light chain (SEQ ID NO: 26 or SEQ ID NO: 27), optionally linked by a peptide linker.

According to certain embodiments, the extracellular antigen binding domain is directed against CD123. Such extracellular antigen binding domain may be a scFV derived from a CD123 monoclonal antibody.

According to other certain embodiments, the extracellular antigen binding domain is directed against ROR1. Such extracellular antigen binding domain may be a scFV derived from a ROR1 monoclonal antibody.

According to other certain embodiments, the extracellular antigen binding domain is directed against BCMA. Such extracellular antigen binding domain may be a scFV derived from a BCMA monoclonal antibody.

According to other certain embodiments, the extracellular antigen binding domain may be directed against CD20. Such extracellular antigen binding domain may be a scFV derived from a CD20 monoclonal antibody.

According to other certain embodiments, the extracellular antigen binding domain may be directed against CD33. Such extracellular antigen binding domain may be a scFV derived from a CD33 monoclonal antibody.

A chimeric antigen receptor according to the invention comprises at least one ectodomain comprising a signal transducing domain and optionally a co-stimulatory domain The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Non-limiting examples of ITAM which can be employed in accordance with the invention can include those derived from TCRzeta, FcRgamma, FcRbeta, FcRepsilon, CD3gamma, CD3delta, CD3epsilon, CD3 zeta, CD5, CD22, CD79a, CD79b and CD66d.

According to certain embodiments, the signaling domain comprises the CD3zeta signaling domain, or the intracytoplasmic domain of the FcεRI beta or gamma chains.

According to particular embodiments, the signaling domain comprises a CD3 zeta signaling domain. According to more particular embodiments, the signaling domain comprises the CD3 zeta signaling domain as set forth in SEQ ID NO: 28. According to other more particular embodiments, the signaling domain comprises a variant of the CD3 zeta signaling domain as set forth in SEQ ID NO: 28 having at least 80, such as at least 85, at least 90, at least 95, at least 98 or at least 99%, sequence identity with CD3 zeta signaling domain as set forth in SEQ ID NO: 28. A variant of a CD3 zeta signaling domain may differ from said CD3 zeta signaling domain in the substitution of one or more (such as 1 to 10, 1 to 5, or 1 to 3) amino acid residue(s). Alternatively, or in addition, such variant may differ from said CD3 zeta signaling domain in the addition or deletion of one or more (such as 1 to 10, 1 to 5, or 1 to 3) amino acid residue(s). Suitable, a variant is one which has the same or similar function and activity as seen for the CD3 zeta signaling domain (SEQ ID NO: 28).

According to other particular embodiments, the signaling domain comprises the intracytoplasmic domain of the FcεRI beta or gamma chains or a variant thereof.

According to more particular embodiments, the signaling domain comprises the intracytoplasmic domain of the FcεRI beta chain (SEQ ID NO: 29). According to other more particular embodiments, the signaling domain comprises a variant of the intracytoplasmic domain of the FcεRI beta chain (SEQ ID NO: 29) having at least 80, such as at least 85, at least 90, at least 95, at least 98 or at least 99%, sequence identity with intracytoplasmic domain of the FcεRI beta chain (SEQ ID NO: 29). A variant of the intracytoplasmic domain of the FcεRI beta chain may differ from said intracytoplasmic domain in the substitution of one or more (such as 1 to 10, 1 to 5, or 1 to 3) amino acid residue(s). Alternatively, or in addition, such variant may differ from said intracytoplasmic domain in the addition or deletion of one or more (such as 1 to 10, 1 to 5, or 1 to 3) amino acid residue(s). Suitable, a variant is one which has the same or similar function and activity as seen for the intracytoplasmic domain of the FcεRI beta chain (SEQ ID NO: 29).

According to other more particular embodiments, the signaling domain comprises the intracytoplasmic domain of the FcεRI gamma chain (SEQ ID NO: 30). According to other more particular embodiments, the signaling domain comprises a variant of the intracytoplasmic domain of the FcεRI gamma chain (SEQ ID NO: 30) having at least 80, such as at least 85, at least 90, at least 95, at least 98 or at least 99%, sequence identity with intracytoplasmic domain of the FcεRI gamma chain (SEQ ID NO: 30). A variant of the intracytoplasmic domain of the FcεRI gamma chain may differ from said intracytoplasmic domain in the substitution of one or more (such as 1 to 10, 1 to 5, or 1 to 3) amino acid residue(s). Alternatively, or in addition, such variant may differ from said intracytoplasmic domain in the addition or deletion of one or more (such as 1 to 10, 1 to 5, or 1 to 3) amino acid residue(s). Suitable, a variant is one which has the same or similar function and activity as seen for the intracytoplasmic domain of the FcεRI gamma chain (SEQ ID NO: 30).

According to certain embodiments, the CAR of the present invention comprises in at least one endodomain a co-stimulatory domain.

The co-stimulatory domain may be any cytoplasmic domain of a costimulatory molecule. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory signal" as used herein refers to a signal, which in combination with primary signal, such as TCR/CD3 ligation, leads to T cell proliferation and/or upregulation or downregulation of key molecules.

The co-stimulatory domain may, for example, be the cytoplasmic domain from a costimulatory molecule selected from CD27, CD28, 4-1BB, OX40, CD30, CD40, PD-1, ICOS, lymphocyte function-associated antigen-1 (LFA-1), CD2, CD7, CD8, LIGHT, NKG2C, B7-H3, a ligand that specifically binds with CD83, and any combination thereof.

Thus, according to certain embodiments, the co-stimulatory domain is a co-stimulatory domain from 4-1BB. According to particular embodiments, the co-stimulatory domain is a co-stimulatory domain from 4-1BB as set forth in SEQ ID NO: 31. According to other particular embodiments, the co-stimulatory domain is variant of the co-stimulatory domain from 4-1BB as set forth in SEQ ID NO: 31 having at least 80, such as at least 85, at least 90, at least 95, at least 98 or at least 99%, sequence identity with co-stimulatory domain from 4-1BB as set forth in SEQ ID NO: 31. A variant of the co-stimulatory domain from 4-1BB may differ from said co-stimulatory domain in the substitution of one or more (such as 1 to 10, 1 to 5, or 1 to 3) amino acid residue(s). Alternatively, or in addition, such variant may differ from said co-stimulatory domain in the addition or deletion of one or more (such as 1 to 10, 1 to 5, or 1 to 3) amino acid residue(s). Suitable, a variant is one which has the same or similar function and activity as seen for the co-stimulatory domain from 4-1BB (SEQ ID NO: 31).

A chimeric antigen receptor according to the invention comprises at least one transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The at least one transmembrane domain can be derived either from a natural or from a synthetic source. The at least one transmembrane domain can be derived from any membrane-bound or transmembrane protein. As non-limiting examples, the at least one transmembrane domain can be a subunit of the T cell receptor such as α, β, γ or δ, polypeptide constituting CD3 complex, IL2 receptor p55 (α chain), p75 (β chain) or γ chain, subunit chain of Fc receptors, in particular Fcγ receptor III or CD proteins. Alternatively, the at least one transmembrane domain can be synthetic and can comprise predominantly hydrophobic residues such as leucine and valine.

The at least one transmembrane domain may, for example, be derived from the CD8 alpha chain. Thus, according to certain embodiments, the at least one transmembrane domain is a CD8 alpha transmembrane domain. According to particular embodiments, the at least one transmembrane domain is a CD8 alpha transmembrane domain (SEQ ID NO: 32). According to other particular embodiments, the at least one transmembrane domain is a variant of a CD8 alpha transmembrane domain (SEQ ID NO: 32) having at least 80, such as at least 85, at least 90, at least 95, at least 98 or at least 99%, sequence identity with the human CD8 alpha transmembrane domain (SEQ ID NO: 32). A variant of the CD8 alpha transmembrane domain may differ from said transmembrane domain in the substitution of one or more (such as 1 to 10, 1 to 5, or 1 to 3) amino acid residue(s). Alternatively, or in addition, such variant may differ from said transmembrane domain in the addition or deletion of one or more (such as 1 to 10, 1 to 5, or 1 to 3) amino acid residue(s). Suitable, a variant is one which has the same or similar function as seen for the CD8 alpha transmembrane domain (SEQ ID NO: 32).

Alternatively, the at least one transmembrane domain may be derived from 4-1BB. Thus, according to certain embodiments, the at least one transmembrane domain is a 4-1BB transmembrane domain (SEQ ID NO: 33). According to particular embodiments, the at least one transmembrane domain is a 4-1BB transmembrane domain (SEQ ID NO: 33). According to other particular embodiments, the at least one transmembrane domain is a variant of a 4-1BB transmembrane domain (SEQ ID NO: 33) having at least 80, such as at least 85, at least 90, at least 95, at least 98 or at least 99%, sequence identity with the 4-1BB transmembrane domain (SEQ ID NO: 33). A variant of the 4-1BB transmembrane domain may differ from said transmembrane domain in the substitution of one or more (such as 1 to 10, 1 to 5, or 1 to 3) amino acid residue(s). Alternatively, or in addition, such variant may differ from said transmembrane domain in the addition or deletion of one or more (such as 1 to 10, 1 to 5, or 1 to 3) amino acid residue(s). Suitable, a variant is one which has the same or similar function as seen for the 4-1BB transmembrane domain (SEQ ID NO: 33).

Alternatively, the at least one transmembrane domain may be derived from the Fcε receptor chains or variant thereof. Particularly, the transmembrane domain may be selected from the transmembrane domains of the FcεRI α, β and γ chains, fragments or variants thereof. Thus, according to certain embodiments, the at least one transmembrane domain is the transmembrane domain from the alpha chain of high-affinity IgE receptor (FcεRI) (SEQ ID NO: 34). According to certain other embodiments, the at least one transmembrane domain is a variant of the transmembrane domains of the FcεRI α chain having at least 80, such as at least 85, at least 90, at least 95, at least 98 or at least 99%, sequence identity with FcεRI α (SEQ ID NO: 34). A variant of the transmembrane domain of the FcεRI α chain may differ from said transmembrane domain in the substitution of one or more (such as 1 to 10, 1 to 5, or 1 to 3) amino acid residue(s). Alternatively, or in addition, such variant may differ from said transmembrane domain in the addition or deletion of one or more (such as 1 to 10, 1 to 5, or 1 to 3) amino acid residue(s). Suitable, a variant is one which has the same or similar function as seen for the transmembrane domains of the FcεRI α chain (SEQ ID NO: 34).

In case that the chimeric antigen receptor is a multi-chain CAR, which is composed of at least two different polypeptide chains, each of which contains at least one transmembrane domain, the transmembrane domains may, for example, be selected from the transmembrane domains of the FcεRI α, β and γ chains, fragments or variants thereof.

Thus, the at least one transmembrane domain comprised by a first polypeptide chain comprising at least one ectodomain in accordance with the invention may be the transmembrane domain from the alpha chain of high-affinity IgE receptor (FcεRI) (SEQ ID NO: 34) or a variant thereof having at least 80, such as at least 85, at least 90, at least 95, at least 98 or at least 99%, sequence identity with FcεRI α (SEQ ID NO: 34). The at least one transmembrane domain comprised by a second polypeptide chain comprising at least one endodomain in accordance with the invention may be the transmembrane domain from the gamma or beta chain of FcεRI (SEQ ID NO: 35 and 36, respectively) or a variant thereof having at least 80, such as at least 85, at least 90, at least 95, at least 98 or at least 99%, sequence identity with FcεRI γ or β (SEQ ID NO: 35 and 36, respectively). The at least one transmembrane domain comprised by a third polypeptide chain comprising at least one endodomain in accordance with the invention may be the transmembrane domain from the gamma or beta chain of FcεRI (SEQ ID NO: 35 and 36, respectively) or a variant thereof having at least 80, such as at least 85, at least 90, at least 95, at least 98 or at least 99%, sequence identity with FcεRI γ or β (SEQ ID NO: 35 and 36, respectively).

A variant of the transmembrane domain of the FcεRI γ or β chain may differ from said transmembrane domain in the substitution of one or more (such as 1 to 10, 1 to 5, or 1 to 3) amino acid residue(s). Alternatively, or in addition, such variant may differ from said transmembrane domain in the addition or deletion of one or more (such as 1 to 10, 1 to 5, or 1 to 3) amino acid residue(s). Suitable, a variant is one which has the same or similar function as seen for the transmembrane domains of the FcεRI γ or β chain (SEQ ID NO: 35 or 36, respectively).

A chimeric antigen receptor according to the present invention may be a single chain CAR. A single chain CAR is a chimeric antigen receptor wherein all domains of which said CAR is composed are located on one polypeptide chain. A non-limiting illustration of a single chain CAR according to the present invention is shown in FIG. 1A.

Figure 2:
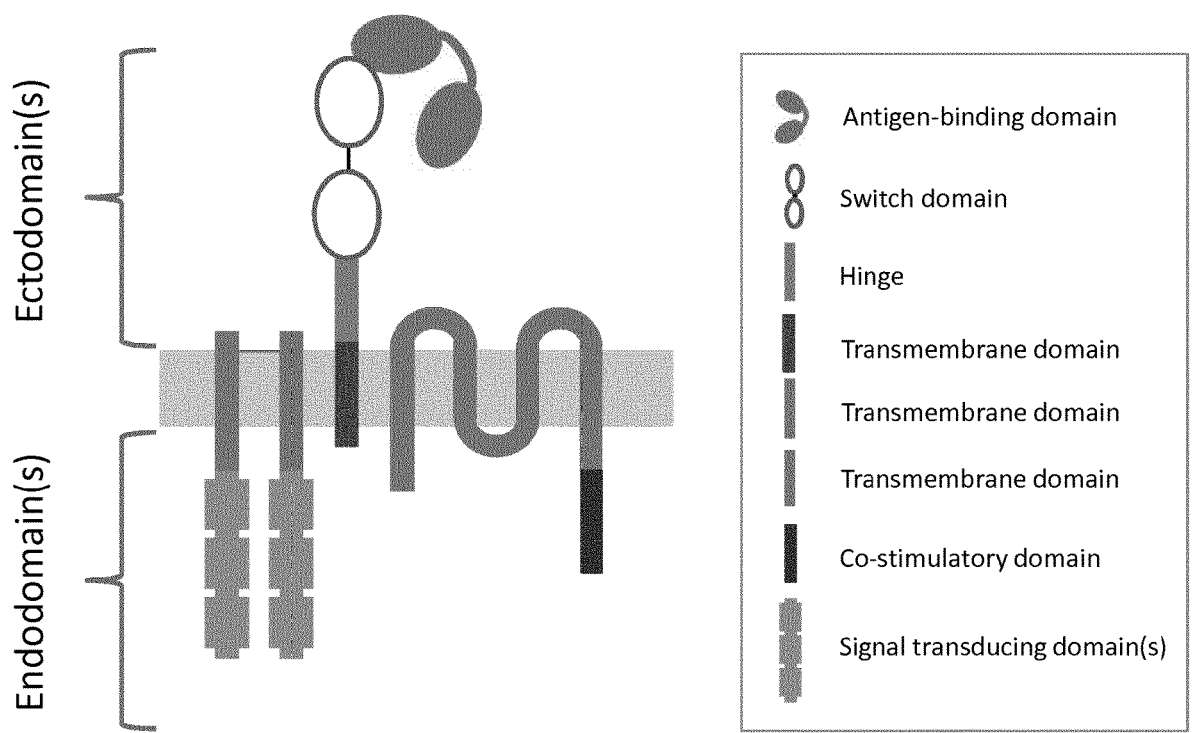
FIG. 2. Schematic illustration of a multi-chain chimeric antigen receptor according to the present invention FIG. 3. (A) Percentages of live cells positive for surface detection of mcCAR in function of presence of vehicle (DMSO) or rapamycin. The detection of the Fab'2 region of the scFv is shown. (B) The fold increase in the median fluorescence intensity (MFI) upon addition of the small molecule rapamycin as depicted in the whole live cell population.

Alternatively, a chimeric antigen receptor according to the present invention may be a multi-chain CAR. A non-limiting illustration of a multi-chain CAR according to the present invention is shown in FIG. 2. According to this architecture, at least on ectodomain and the at least one endodomain are born on different polypeptide chains. The different polypeptide chains are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently described by the applicant in PCT/US2013/058005.

Accordingly, a multi-chain CAR according to the invention may be one which comprises:

A) a first polypeptide chain comprising
  a) at least one ectodomain which comprises:
    i) an extracellular antigen binding domain; and
    ii) a switch domain comprising at least a first multimerizing ligand-binding domain and a second multimerizing ligand-binding domain which are capable of binding to a predetermined multivalent ligand to form a multimer comprising said two binding domains and the multivalent ligand to which they are capable of binding; and
  aa) at least one transmembrane domain; and
B) a second polypeptide chain comprising
  b) at least one endodomain comprising a signal transducing domain and optionally a co-stimulatory domain; and
  bb) at least one transmembrane domain.

According to certain embodiments, a multi-chain CAR of the invention may further comprise:

C) a third polypeptide chain comprising
  c) at least one endodomain comprising a co-stimulatory domain; and
  cc) at least one transmembrane domain.

The assembly of the different chains as part of a single multi-chain CAR is made possible, for instance, by using the different alpha, beta and gamma chains of the high affinity receptor for IgE (FcεRI) (Metzger, Alcaraz et al. 1986). Such multi-chain CARs can be derived from FcεRI, by replacing the high affinity IgE binding domain of FcεRI alpha chain by an ectodomain as detailed herein, whereas the N and/or C-termini tails of FcεRI beta and/or gamma chains are fused to an ectodomain as detailed herein comprising a signal transducing domain and co-stimulatory domain, respectively. The extracellular ligand binding domain has the role of redirecting T-cell specificity towards cell targets, while the signal transducing domains activate the immune cell response. The fact that the different polypeptide chains derived from the alpha, beta and gamma polypeptides from FcεRI are transmembrane polypeptides sitting in juxtamembrane position, provides a more flexible architecture to CARs, improving specificity towards the antigen target and reducing background activation of immune cells.

Thus, according to particular embodiments, the first polypeptide chain (A) comprising the ectodomain comprises the transmembrane domain from the alpha chain of high-affinity IgE receptor (FcεRI), whereas the second polypeptide chain (B) comprising the endodomain which comprises the signal transducing domain comprises the transmembrane domain from the gamma or beta chain of FcεRI, such as the transmembrane domain from the gamma chain of FcεRI. If present, the third polypeptide chain (C) comprising the endodomain which comprises the co-stimulatory domain comprises the transmembrane domain from the gamma or beta chain of FcεRI, such as the transmembrane domain from the beta chain of FcεRI.

The conformation of the at least one ectodomain of the chimeric antigen receptor is preferably such that in absence of the corresponding multimerizing ligand the extracellular binding domain is not capable of binding to the targeted antigen. The binding of the multimerizing ligand to the switch domain then results in a conformational change which exposes the extracellular binding domain in a manner that allows its binding to the targeted antigen (this mechanism may be referred to as switch on). The appropriate conformation can be determined on the basis of the cytolytic activity (cytotoxicity) of an immune cell expressing said CAR. With "cytolytic activity" it is meant the percentage of cell lysis of target cells conferred by an immune cell expressing said CAR.

A method for determining the cytotoxicity is described below:

With Adherent Target Cells:

$2\times10^4$ specific target antigen (STA)-positive or STA-negative cells are seeded in 0.1 ml per well in a 96 well plate. The day after the plating, the STA-positive and the STA-negative cells are labeled with CellTrace CFSE and co-cultured with $4\times10^5$ T cells for 4 hours. The cells are then harvested, stained with a fixable viability dye (eBioscience) and analyzed using the MACSQuant flow cytometer (Miltenyi).

The percentage of specific lysis is calculated using the following formula:

$$\% \text{ cell lysis} = 100\% - \frac{\dfrac{\% \text{ viable target cells upon coculture with } CAR \text{ modified } T \text{ cells}}{\% \text{ viable control cells upon coculture with } CAR \text{ modified } T \text{ cells}}}{\dfrac{\% \text{ viable target cells upon coculture with } CAR \text{ non modified } T \text{ cells}}{\% \text{ viable control cells upon coculture with } CAR \text{ non modified } T \text{ cells}}}$$

With Suspension Target Cells:

STA-positive and STA-negative cells are respectively labeled with CellTrace CFSE and CellTrace Violet. About $2\times10^4$ ROR1-positive cells are co-cultured with $2\times10^4$ STA-negative cells with $4\times10^5$ T cells in 0.1 ml per well in a 96-well plate. After a 4 hour incubation, the cells are harvested and stained with a fixable viability dye (eBioscience) and analyzed using the MACSQuant flow cytometer (Miltenyi).

The percentage of specific lysis is calculated using the previous formula.

"Specific target antigen (STA)-positive cells" means cells which express the target antigen for which the chimeric antigen receptor shows specificity, whereas "STA-negative cells" means cells which do not express the specific target antigen. By way of a non-limiting example, if the CAR is directed against CD19, the specific target antigen is thus CD19. Accordingly, CD19-positive and CD19-negative cells are to be used to determine the cytolytic activity.

Hence, the above-described cytotoxicity assay will have to be adapted to the respective target cells depending on the antigen-specificity of the chimeric antigen receptor expressed by the immune cell.

Similar methods for assaying the cytolytic activity are also described in, e.g., Valton et al. (2015) or Poirot et al. (2015).

According to certain embodiments, a chimeric antigen receptor according to the present invention confers a modulated cytolytic activity to an immune cell expressing same in the presence of a corresponding multimerizing ligand compared to the cytolytic activity of said immune cell in the absence of the multimerizing ligand.

According to particular embodiments, a chimeric antigen receptor of the present invention is one which confers an increased cytolytic activity to an immune cell expressing same in the presence of a corresponding multimerizing ligand compared to the cytolytic activity of said immune cell in the absence of the multimerizing ligand. By "increased cytolytic activity" it is meant that the % cell lysis of target cells conferred by the immune cell expressing said CAR increases by at least 10%, such as at least 20%, at least 30%, at least 40%, at least 50%, at least 60%, at least 70%, at least 80%, at least 90% or at least 100%, in the presence of the multimerizing ligand compared to the % cell lysis of target cells conferred by the immune cell in the absence of the multimerizing ligand.

According to other particular embodiments, a chimeric antigen receptor of the present invention is one which confers a decreased cytolytic activity to an immune cell expressing same in the presence of a corresponding multimerizing ligand compared to the cytolytic activity of said immune cell in the absence of the multimerizing ligand. By "decreased cytolytic activity" it is meant that the % cell lysis of target cells conferred by the immune cell expressing said CAR decreases by at least 10%, such as at least 20%, at least 30%, at least 40%, at least 50%, at least 60%, at least 70%, at least 80%, at least 90% or at least 100%, in the presence of the multimerizing ligand compared to the % cell lysis of target cells conferred by the immune cell in the absence of the multimerizing ligand.

By "corresponding multimerizing ligand" is meant a multimerizing ligand which is bound by both the first multimerizing ligand-binding domain and the second multimerizing ligand-binding domain, and thus promotes multimerization (e.g., dimerization) between the first and second multimerizing ligand-binding domains. By way of a non-limiting example, if the first multimerizing ligand-binding domain is KBP12 and the second multimerizing ligand-binding domain is FRB, then the "corresponding ligand-binding domain" may be rapamycin.

Polynucleotides, vectors:

The present invention also relates to polynucleotides and vectors that comprise one or more nucleotide sequences encoding a chimeric antigen receptor according to the invention. The present invention provides polynucleotides, including DNA and RNA molecules, which comprise one or more nucleotide sequences encoding a chimeric antigen receptor. In case the chimeric antigen receptor is a multi-chain CAR, at least one polynucleotide is provided which comprises two or more nucleotide sequence encoding the polypeptide chains composing the multi-chain CAR according to the invention. According to certain embodiments, a composition is provided comprising a first polynucleotide comprising a nucleotide sequence encoding a first polypeptide chain and a second polynucleotide comprising a nucleotide sequence encoding a second polypeptide chain. Optionally, the composition comprises a third polynucleotide comprising a nucleotide sequence encoding a third polypeptide chain.

The polynucleotide(s) may be comprised by an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

According to certain embodiments, the different nucleotide sequences can be included in one polynucleotide or vector which comprises a nucleotide sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the different polypeptides of the multi-chain CAR.

To direct, transmembrane polypeptide such as FcεR into the secretory pathway of a host cell, a secretory signal sequence (also known as a leader sequence, prepro sequence or pre sequence) is provided in polynucleotide sequence or vector sequence. The secretory signal sequence may be that of FcεR, or may be derived from another secreted protein (e.g., t-PA) or synthesized de novo. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the residues 1 to 25 of the FcεRI alpha chain.

Those skilled in the art will recognize that, in view of the degeneracy of the genetic code, considerable sequence variation is possible among these polynucleotide molecules. Preferably, the nucleotide sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods for Engineering an Immune Cell

The present invention further relates to methods of preparing immune cells for immunotherapy comprising introducing into said immune cells a CAR according to the present invention and expanding said cells. In particular, a method for engineering an immune cell is provided, said method comprises:
(i) Providing an immune cell, such as such as T cell; and
(ii) Expressing on the surface of said immune cell at least one chimeric antigen receptor according to the present invention.

According to certain embodiments, the method comprises:
(a) Providing an immune cell;
(b) Introducing into said cell at least one polynucleotide or vector according to the present invention; and
(c) Expressing a chimeric antigen receptor of the invention in said cell.

In a preferred embodiment, said polynucleotides are included in lentiviral vectors in view of being stably expressed in the cells.

In order to enhance, for example, an antitumor effect, it is contemplated to further express on the surface of the immune cell at least one co-stimulatory receptor. Thus, the method for engineering an immune cell may comprises (iii) expressing on the surface of the immune cell at least one co-stimulatory receptor.

According to certain embodiments, the method further comprises:
(d) Introducing into said cell at least one polynucleotide comprising a nucleotide sequence encoding a co-stimulatory receptor; and
(e) Expressing said at least one co-stimulatory receptor.

A "co-stimulatory receptor", as used herein, is meant to be a member of a family of receptors that modulate the activation of T-lymphocytes by the T cell receptor (TCR). The receptors are responsive to one or more B7 antigens found on antigen presenting cells, and, depending upon the specific ligand-receptor combination, modulate a variety of T-cell functions such as the rate of clonal expansion, cell survival and cytokine production. Non-limiting examples of suitable co-stimulatory receptors to be expressed by an immune cell according to the invention include NKG2D (UniProtKB: P26718) and DAP10 (UniProtKB: Q9UBK5).

According to certain embodiments, the immune cell expresses on its surface at least NKG2D.

According to certain other embodiments, the immune cell expresses on its surface at least DAP10.

The expression of the at least one co-stimulatory receptor may be transient or constitutively. Thus, according to certain embodiments, the at least one co-stimulatory receptor is transiently expressed by the immune cell. According to other certain embodiments, the at least one co-stimulatory receptor is constitutively expressed by the immune cell.

Delivery Methods

The different methods described above involve introducing CAR into a cell. As non-limiting example, said CAR can be introduced as transgenes encoded by one plasmidic vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Engineered Immune Cells

The present invention also relates to immune cells, e.g., isolated immune cells, or cell lines susceptible to be obtainable by said method to engineer cells.

In particular, an immune cell, e.g. isolated immune cell, according to the present invention comprises at least one CAR of the present invention. According to certain embodiments, said immune cell, e.g. isolated immune cell, comprises a population of CARs each one comprising different extracellular ligand binding domains. In particular, said immune cell, e.g. isolated immune cell, comprises one or more exogenous polynucleotide sequences encoding polypeptide(s) composing at least one CAR. Genetically modified immune cells of the present invention are activated and proliferate independently of antigen binding mechanisms.

An "immune cell", as referred to herein, means a cell of hematopoietic origin functionally involved in the initiation and/or execution of innate and/or adaptative immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said immune cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. According to particular embodiments, said immune cell can be derived from the group consisting of CD4+T-lymphocytes and CD8+T-lymphocytes. According to more particular embodiments, said immune cell can be derived from CD4+T-lymphocytes.

According to certain embodiments, the immune cell is a human immune cell, such as a human T-lymphocyte.

Since rapamycin directly inhibits immune cells, such as T cells, through interaction with the cytosolic protein FK-binding protein 12 (FKBP12) followed by inhibition of mTOR (mammalian target of rapamycin) by the FKBP12/rapamycin complex, it may thus be desirable to inhibit the formation of the endogenous FKBP12/rapamycin/mTOR complex.

The inhibition of the formation of the endogenous FKBP12/rapamycin/mTOR complex may be achieved, e.g., by introducing one or more amino acid substitution, including an amino acid substitution at position 2035, within the mTOR protein sequence (NCBI Reference Sequence: NP_004949.1; SEQ ID NO: 37). Techniques for introducing an amino acid substation within the amino acid sequence of a protein are well known to a skilled person, and include as a non-limiting example site directed mutagenesis.

An immune cell of the present invention may thus be further modified to comprise within the endogenous mTOR protein at least an amino acid substitution at position 2035, wherein serine is replaced by another amino acid. Thus, according to certain embodiments, the immune cell comprises within the amino acid sequence of the endogenous mTOR protein one or more amino acid substitutions, including an amino acid substitution at position 2035 wherein serine is replaced by another amino acid, such as Ile.

The inhibition of the formation of the endogenous FKBP12/rapamycin/mTOR complex may also be achieved, e.g., by inactivating the endogenous FKBP12 gene. By "inactivating" or "inactivation of" a gene it is intended that the gene of interest (e.g., the FKBP12 gene) is not expressed in a functional protein form. Techniques for inactivating a gene are well-known to those of skill in the art, and include as non-limiting example the use of specific rare-cutting endonucleases targeting this gene, such as TAL-nuclease, meganuclease, zing-finger nuclease (ZFN), or RNA guided endonuclease. Further non-limiting examples include Cas9/Crispr or argonaute (Ago) based systems, such as disclosed in WO2014/191128 and Swarts et al (2014), respectively.

An immune cell of the present invention may thus be further modified to inactivate the endogenous FKBP12 gene. Thus, according to certain embodiments, the immune cell comprises an inactivated FKBP12 gene. Such immune cell thus does not express the FKPB12 protein.

To keep immune cells in a proliferation state, avoiding a precocious re-administration of new engineered immune cells, it may be appropriate to use virus-specific T cells (VSTs). Without being cytotoxic in their native form, VSTs are stimulated by endogenous viral antigen by engagement of their native receptors, and then are allowed to proliferate.

Expansion and persistence would occur irrespectively of the presence of the CAR target antigen. When engineered according to the present invention, i.e. bearing the ectodomain switch system, the VSTs may benefit from their properties of proliferation without the presence of the CAR target antigen, while non-VSTs T cells would not proliferate and finally die. Donor-derived virus-specific T cells engineered to express a CD19 specific chimeric antigen receptor and the generation thereof has been described in Cruz et al. (2013).

Thus, according to certain embodiments, the immune cell is a virus-specific T cell (VST), preferably isolated from a donor.

Prior to expansion and genetic modification of the immune cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

An immune cell according to the present invention may further be modified to be allogenic. Thus, according to certain embodiments, the immune cell further comprise at least one inactivated gene selected from the group consisting of CD52, GR, TCR alpha, TCR beta, HLA gene, immune check point genes such as PD1 and CTLA-4, or can express a pTalpha transgene. More particularly, the immune cell may comprise at least one inactivated gene selected TCR alpha or TCR beta genes. Such inactivation renders the TCR not functional in the cells. This strategy is particularly useful to avoid Graft versus Host Disease (GvHD). Methods for inactivating genes are known in the art, and include the use of rare-cutting endonucleases which able to selectively inactivate by DNA cleavage, preferably by double-strand break, the gene(s) of interest. Said genes may thus be inactivated by transforming the immune cell with a polynucleotide comprising a nucleotide sequence encoding a rare-cutting endonuclease able to selectively inactivate by DNA cleavage, preferably by double-strand break a gene selected from the group consisting of CD52, GR, TCR alpha, TCR beta, HLA gene, immune check point genes such as PD1 and CTLA-4. Said rare-cutting endonuclease can be a meganuclease, a Zinc finger nuclease or a TALE-nuclease. According to particular embodiments, said rare-cutting endonuclease is a TALE-nuclease. Preferred methods and relevant TALE-nucleases have been described in WO2013176915. According to other particular embodiments, said rare-cutting endonuclease is RNA-guided endonuclease such as Cas9 or DNA-guided endonuclease, such as Argonaute based techniques as described in WO2014189628.

An immune cell according to the present invention may further be modified to be resistant to chemotherapy drugs. Thus, according to certain embodiments, the immune cell further comprises at least one inactivated gene responsible for the cell's sensitivity to the drug (drug sensitizing gene (s)), such as the dcK and/or HPRT genes. Methods for inactivating genes are known in the art, and include the use of rare-cutting endonucleases which able to selectively inactivate by DNA cleavage, preferably by double-strand break, the gene(s) of interest. Said gene(s) may thus be inactivated by transforming the immune cell with a polynucleotide comprising a nucleotide sequence encoding a rare-cutting endonuclease able to selectively inactivate by DNA cleavage, preferably by double-strand break at least one gene responsible for the cell's sensitivity to the drug (drug sensitizing gene(s). Said rare-cutting endonuclease can be a meganuclease, a Zinc finger nuclease or a TALE-nuclease. According to particular embodiments, said rare-cutting endonuclease is a TALE-nuclease. Preferred methods and relevant TALE-nucleases have been described in WO2013176915. According to other particular embodiments, said rare-cutting endonuclease is RNA-guided endonuclease such as Cas9 or DNA-guided endonuclease, such as Argonaute based techniques as described in WO2014189628.

Alternatively, the resistance to drugs can be conferred to an immune cell, such as a T cell, by expressing a drug resistance gene. Variant alleles of several genes such as dihydrofolate reductase (DHFR), inosine monophosphate dehydrogenase 2 (IMPDH2), calcineurin or methylguanine transferase (MGMT) have been identified to confer drug resistance to an immune cell according to the invention.

Activation and Expansion of T Cells

Whether prior to or after genetic modification of the immune cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534, 055; 6,905,680; 6,692,964; 5,858,358; 6,887,466; 6,905, 681; 7,144,575; 7,067,318; 7,172,869; 7,232,566; 7,175, 843; 5,883,223; 6,905,874; 6,797,514; 6,867,041; and U.S. Patent Application Publication No. 20060121005. T cells can be expanded in vitro or in vivo.

Generally, the immune cells of the invention are expanded by contact with an agent that stimulates a CD3 TCR complex and a co-stimulatory molecule on the surface of the T cells to create an activation signal for the T-cell.

For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics According to certain embodiments, said cells can be expanded by co-culturing with tissue or cells. Said cells can also be expanded in vivo, for example in the subject's blood after administrating said cell into the subject.

Therapeutic Applications

Immune cells obtainable in accordance with the present invention are intended to be used as a medicament, and in particular for treating cancer in a patient (e.g. a human patient) in need thereof. Accordingly, the present invention provides immune cells for use as a medicament. Particularly, the present invention provides immune cells for use in the treatment of a cancer. Also provided are compositions, particularly pharmaceutical compositions, which comprise at least one immune cell of the present invention. In certain embodiments, a composition may comprise a population of immune cells of the present invention.

The treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of immune cells, such as T-cells, typically obtained from donors, into non-alloreactive cells. This may be done under standard protocols and reproduced as many times as needed. The resultant modified immune cells may be pooled and administrated to one or several patients, being made available as an "off the shelf" therapeutic product.

The treatments are primarily to treat patients diagnosed with cancer. Particular cancers to be treated according to the invention are those which have solid tumors, but may also concern liquid tumors. Adult tumors/cancers and pediatric tumors/cancers are also included.

According to certain embodiments, the immune cell(s) or composition is for use in the treatment of a cancer, and more particularly for use in the treatment of a solid or liquid tumor. According to particular embodiments, the immune cell(s) or composition is for use in the treatment of a solid tumor. According to other particular embodiments, the immune cell(s) or composition is for use in the treatment of a liquid tumor.

According to particular embodiments, the immune cell(s) or composition is for use in the treatment of a cancer selected from the group consisting of lung cancer, small lung cancer, breast cancer, uterine cancer, prostate cancer, kidney cancer, colon cancer, liver cancer, pancreatic cancer, and skin cancer. According to more particular embodiments, the immune cell(s) or composition is for use in the treatment of lung cancer. According to other more particular embodiments, the immune cell(s) or composition is for use in the treatment of small lung cancer. According to other more particular embodiments, the immune cell(s) or composition is for use in the treatment of breast cancer. According to other more particular embodiments, the immune cell(s) or composition is for use in the treatment of uterine cancer. According to other more particular embodiments, the immune cell(s) or composition is for use in the treatment of prostate cancer. According to other more particular embodiments, the immune cell(s) or composition is for use in the treatment of kidney cancer. According to other more particular embodiments, the immune cell(s) or composition is for use in the treatment of colon cancer. According to other more particular embodiments, the immune cell(s) or composition is for use in the treatment of liver cancer.

According to other more particular embodiments, the immune cell(s) or composition is for use in the treatment of pancreatic cancer. According to other more particular embodiments, the immune cell(s) or composition is for use in the treatment of skin cancer.

According to other particular embodiments, the immune cell(s) or composition is for use in the treatment of a sarcoma.

According to other particular embodiments, the immune cell(s) or composition is for use in the treatment of a carcinoma. According to more particular embodiments, the immune cell or composition is for use in the treatment of renal, lung or colon carcinoma.

According to other particular embodiments, the immune cell(s) or composition is for use in the treatment of leukemia, such as acute lymphoblastic leukemia (ALL), acute myeloid leukemia (AML), chronic lymphocytic leukemia (CLL), chronic myelogenous leukemia (CML), and chronic myelomonocystic leukemia (CMML). According to more particular embodiments, the immune cell(s) or composition is for use in the treatment of acute lymphoblastic leukemia (ALL). According to other more particular embodiments, the immune cell(s) or composition is for use in the treatment of acute myeloid leukemia (AML). According to other more particular embodiments, the immune cell(s) or composition is for use in the treatment of chronic lymphocytic leukemia (CLL). According to other more particular embodiments, the immune cell(s) or composition is for use in the treatment of chronic myelogenous leukemia (CML). According to other more particular embodiments, the immune cell(s) or composition is for use in the treatment of chronic myelomonocystic leukemia (CMML).

According to other particular embodiments, the immune cell(s) or composition is for use in the treatment of lymphoma, such as B-cell lymphoma. According to more particular embodiments, the immune cell(s) or composition is for use in the treatment of primary CNS lymphoma. According to other more particular embodiments, the immune cell(s) or composition is for use in the treatment of Hodgkin's lymphoma. According to other more particular embodiments, the immune cell(s) or composition is for use in the treatment of Non-Hodgkin's lymphoma. According to more particular embodiments, the immune cell(s) or composition is for use in the treatment of diffuse large B cell lymphoma (DLBCL).

According to other more particular embodiments, the immune cell(s) or composition is for use in the treatment of Follicular lymphoma. According to other more particular embodiments, the immune cell(s) or composition is for use in the treatment of marginal zone lymphoma (MZL). According to other more particular embodiments, the immune cell(s) or composition is for use in the treatment of Mucosa-Associated Lymphatic Tissue lymphoma (MALT). According to other more particular embodiments, the immune cell(s) or composition is for use in the treatment of small cell lymphocytic lymphoma. According to other more particular embodiments, the immune cell(s) or composition is for use in the treatment of mantle cell lymphoma (MCL). According to other more particular embodiments, the immune cell(s) or composition is for use in the treatment of Burkitt lymphoma. According to other more particular embodiments, the immune cell(s) or composition is for use in the treatment of primary mediastinal (thymic) large B-cell lymphoma. According to other more particular embodiments, the immune cell(s) or composition is for use in the treatment of Waldenström macroglobulinemia. According to other more particular embodiments, the immune cell(s) or composition is for use in the treatment of nodal marginal zone B cell lymphoma (NMZL). According to other more particular embodiments, the immune cell(s) or composition is for use in the treatment of splenic marginal zone lymphoma (SMZL). According to other more particular embodiments, the immune cell(s) or composition is for use in the treatment of intravascular large B-cell lymphoma. According to other more particular embodiments, the immune cell(s) or composition is for use in the treatment of Primary effusion lymphoma. According to other more particular embodiments, the immune cell(s) or composition is for use in the treatment of lymphomatoid granulomatosis. According to other more particular embodiments, the immune cell(s) or composition is for use in the treatment of T cell/histiocyte-rich large B-cell lymphoma. According to other more particular embodiments, the immune cell(s) or composition is for use in the treatment of primary diffuse large B-cell lymphoma of the CNS (Central Nervous System). According to other more particular embodiments, the immune cell(s) or composition is for use in the treatment of primary cutaneous diffuse large B-cell lymphoma. According to other more particular embodiments, the immune cell(s) or composition is for use in the treatment of EBV positive diffuse large B-cell lymphoma of the elderly. According to other more particular embodiments, the immune cell(s) or composition is for use in the treatment of diffuse large B-cell lymphoma associated with inflammation. According to other more particular embodiments, the immune cell(s) or composition is for use in the treatment of ALK-positive large B-cell lymphoma. According to other more particular embodiments, the immune cell(s) or composition is for use in the treatment of plasmablastic lymphoma. According to other more particular embodiments, the immune cell(s) or composition is for use in the treatment of Large B-cell lymphoma arising in HHV8-associated multicentric Castleman disease.

According to certain embodiments, the immune cell(s) or composition is for use in the treatment of a viral infection, such as an HIV infection or HBV infection.

According to certain embodiment, the immune cell of originates from a patient, e.g. a human patient, to be treated. According to certain other embodiment, the immune cell originates from at least one donor.

The treatment can take place in combination with one or more therapies selected from the group of antibodies therapy, chemotherapy, cytokines therapy, dendritic cell therapy, gene therapy, hormone therapy, laser light therapy and radiation therapy.

According to certain embodiments, immune cells of the invention can undergo robust in vivo immune cell expansion upon administration to a patient, and can persist in the body fluids for an extended amount of time, preferably for a week, more preferably for 2 weeks, even more preferably for at least one month. Although the immune cells according to the invention are expected to persist during these periods, their life span into the patient's body are intended not to exceed a year, preferably 6 months, more preferably 2 months, and even more preferably one month.

The administration of the immune cells or composition according to the present invention may be carried out in any convenient manner, including by aerosol inhalation, injection, ingestion, transfusion, implantation or transplantation. The immune cells or composition described herein may be administered to a patient subcutaneously, intradermally, intratumorally, intranodally, intramedullary, intramuscularly, by intravenous or intralymphatic injection, or intraperitoneally.

According to certain embodiments, the immune cells or composition are/is administered by intravenous injection.

According to other certain embodiments, the immune cell(s) or composition is administrated parenterally.

According to certain other embodiments, the immune cell(s) or composition is administered intratumorally. Said administration can be done by injection directly into a tumor or adjacent thereto.

The administration of the cells or population of cells can consist of the administration of 104-109 cells per kg body weight, preferably $10^5$ to $10^6$ cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

According to certain embodiments, immune cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p7056 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded genetically engineered immune cells of the present invention. In an additional embodiment, expanded cells are administered before or following surgery.

Also encompassed within this aspect of the invention are methods for treating a patient in need thereof, comprising a) providing at least one immune cell of the present invention, preferably a population of said immune cell; and b) administering said immune cell or population to said patient.

Also encompassed within this aspect of the invention are methods for preparing a medicament using at least one immune cell of the present invention, and preferably a population of said immune cell. Accordingly, the present invention provides the use of at least one immune cell of the present invention, and preferably a population of said immune cell, in the manufacture of a medicament. Preferably, such medicament is for use in the treatment of a disease as specified above.

It is particularly envisaged that the immune cell of the present invention is used (or is for use) in combination the multivalent ligand capable of binding to the first and second multimerizing ligand-binding domains. In this respect, the present invention contemplates administering an effective amount of the multivalent ligand of the first and second multimerizing ligand-binding domains to said patient.

The multivalent ligand, such as rapamycin, may be administered to said patient, for example, at a dose of about 0.01 to 10 mg/kg body weight. According to certain embodiments, the multivalent ligand is administered at a dose of about 0.01 to 5 mg/kg body weight. According to certain other embodiments, the multivalent ligand is administered at a dose of about 0.01 to 4 mg/kg body weight. According to certain other embodiments, the multivalent ligand is administered at a dose of about 0.01 to 3 mg/kg body weight. According to certain other embodiments, the multivalent ligand is administered at a dose of about 0.01 to 2 mg/kg body weight. According to certain other embodiments, the multivalent ligand is administered at a dose of about 0.01 to 1 mg/kg body weight. According to certain other embodiments, the multivalent ligand is administered at a dose of about 0.05 to 5 mg/kg body weight. According to certain other embodiments, the multivalent ligand is administered at a dose of about 0.05 to 4 mg/kg body weight. According to certain other embodiments, the multivalent ligand is administered at a dose of about 0.05 to 3 mg/kg body weight. According to certain other embodiments, the multivalent ligand is administered at a dose of about 0.05 to 2 mg/kg body weight. According to certain other embodiments, the multivalent ligand is administered at a dose of about 0.05 to 1 mg/kg body weight. According to certain other embodiments, the multivalent ligand is administered at a dose of about 0.1 to 5 mg/kg body weight. According to certain other embodiments, the multivalent ligand is administered at a dose of about 0.1 to 4 mg/kg body weight. According to certain other embodiments, the multivalent ligand is administered at a dose of about 0.1 to 3 mg/kg body weight. According to certain other embodiments, the multivalent ligand is administered at a dose of about 0.1 to 2 mg/kg body weight. According to certain other embodiments, the multivalent ligand is administered at a dose of about 0.1 to 1 mg/kg body weight. According to certain other embodiments, the multivalent ligand is administered at a dose of about 0.5 to 5 mg/kg body weight. According to certain other embodiments, the multivalent ligand is administered at a dose of about 0.5 to 4 mg/kg body weight. According to certain other embodiments, the multivalent ligand is administered at a dose of about 0.5 to 3 mg/kg body weight. According to certain other embodiments, the multivalent ligand is administered at a dose of about 0.5 to 2 mg/kg body weight. According to certain other embodiments, the multivalent ligand is administered at a dose of about 0.5 to 1 mg/kg body weight. According to certain other embodiments, the multivalent ligand is administered at a dose of about 1 to 5 mg/kg body weight. According to certain other embodiments, the multivalent ligand is administered at a dose of about 2 to 5 mg/kg body weight. According to certain other embodiments, the multivalent ligand is administered at a dose or of about 2.5 to 5 mg/kg body weight.

The administration of the multivalent invention may be carried out in any convenient manner, including by aerosol inhalation, injection, ingestion, transfusion, implantation or transplantation. The multivalent ligand may be administered to a patient subcutaneously, intradermally, intratumorally, intranodally, intramedullary, intramuscularly, by intravenous or intralymphatic injection, or intraperitoneally.

According to certain embodiments, the multivalent ligand is administered by intravenous injection.

According to certain other embodiments, the multivalent ligand is administered intratumorally, optionally together an immune cell or a population of an immune cell according to the present invention. Such approach prevents or limits the activation (on-switching) of the CAR containing immune cell outside the tumor (e.g., a solid tumor) to be treated.

Other Definitions

"ectodomain" refers to a part of a chimeric antigen receptor of the present invention which extends into the extracellular space (the space outside a cell).

"endodomain" refers to a part of a chimeric antigen receptor of the present invention which extends into the cytoplasm of a cell.

Amino acid residues in a polypeptide sequence are designated herein according to the one-letter code, in which, for example, Q means Gln or Glutamine residue, R means Arg or Arginine residue and D means Asp or Aspartic acid residue.

"Substitution" or "substituted" refers to modification of a polypeptide by replacing one amino acid residue with another, for instance the replacement of an Arginine residue with a Glutamine residue in a polypeptide sequence is an amino acid substitution.

"Conservative substitution" refers to a substitution of an amino acid residue with a different residue having a similar side chain, and thus typically involves substitution of the amino acid in the polypeptide with amino acids within the same or similar class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having an aromatic side chain is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in a polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" or "deleted" refers to modification of a polypeptide by removal of one or more amino acids in the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining polypeptide function. Deletions can be directed to the internal portions and/or terminal portions of the polypeptide, in various embodiments, the deletion can comprise a continuous segment or can be discontinuous.

"Insertion" or "inserted" refers to modification of the polypeptide by addition of one or more amino acids to the reference polypeptide. Insertions can comprise addition of 1 or more amino acids, 2 or more amino acids, 5 or more amino acids, 10 or more amino acids, 15 or more amino acids, or 20 or more amino acids. Insertions can be in the internal portions of the polypeptide, or to the carboxy or amino terminus. The insertion can be a contiguous segment of amino acids or separated by one or more of the amino acids in the reference polypeptide.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, or penetrating peptides. In these later cases, delivery vectors are molecule carriers.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By "cell" or "cells" is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

By "stem cell" is meant a cell that has the capacity to self-renew and the ability to generate differentiated cells. More explicitly, a stem cell is a cell which can generate daughter cells identical to their mother cell (self-renewal) and can produce progeny with more restricted potential (differentiated cells).

By "NK cells" is meant natural killer cells. NK cells are defined as large granular lymphocytes and constitute the third kind of cells differentiated from the common lymphoid progenitor generating B and T lymphocytes.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a polypeptide variant obtained by mutation or replacement of at least one residue in the amino acid sequence of the parent molecule.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity", "percentage of sequence identity," "% sequence identity" and "percent identity" are used herein to refer to comparisons between an amino acid sequence and a reference amino acid sequence. The "% sequence identify", as used herein, is calculated from the two amino acid sequences as follows: The sequences are aligned using Version 9 of the Genetic Computing Group's GAP (global alignment program), using the default BLOSUM62 matrix with a gap open penalty of −12 (for the first null of a gap) and a gap extension penalty of −4 (for each additional null in the gap). After alignment, percentage identity is calculated by expressing the number of matches as a percentage of the number of amino acids in the reference amino acid sequence. For example, polypeptides having at least 80%, 85%, 90%, 95%, 98% or 99% identity to specific polypeptides described herein and preferably exhibiting substantially the same functions, as well as polynucleotide encoding such polypeptides, are contemplated.

"Reference sequence" or "reference amino acid sequence" refers to a defined sequence to which another sequence is compared.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Example 1: Development of a Small Molecule (Rapamycin) Switch-on mcCAR19 and mcCAR123—mRNA Delivery—Surface Detection Constructs and mRNA Preparation All constructs originated from the pCLS24707 (SEQ ID NO: 38) which encode the α-chain (SEQ ID NO: 39), β-chain (SEQ ID NO: 40) and γ-chain (SEQ ID NO: 41) of the multichain CAR (mcCAR). The sequences coding for the FRB domain (SEQ ID NO: 2) and FKBP domain (SEQ ID NO: 1) were synthetized de novo (GeneCust). The scFV, hinge-transmembrane-intracytoplasmic alpha chain domain, the FRB and the FKBP were further amplified by PCR to generate golden gate assembly compatible fragments (SEQ ID NO: 42 to 45). In addition an FRB-FKBP and an FKBP-FRB fragment were generated (SEQ ID NO: 46 to 47) using a four-EAAAR-linker (SEQ ID NO: 19) or a –GS-4x-EAAAR-linker (SEQ ID NO: 20) and standard molecular biology procedures. Fragments were then assembled using round of restriction and ligation leading to pCLS26563, pCLS26564, pCLS26881, and pCLS27123 (SEQ ID NO: 48 to 51). The respective amino acid sequences encoded by these constructs are shown in SEQ ID NOs: 52 to 55.

All individual chains were amplified by PCR using oligo pairs α-chain-F/α-chain-R, β-chain-F/β-chain-R and γ-chain-F/γ-chain-R (SEQ ID NO: 56 to 61) prior to mRNA synthesis. mRNA encoding the different α-chains, β-chain, γ-chain were in vitro transcribed from the PCR product and polyadenylated using the mMessage mMachine T7 Ultra kit (Life technologies) following the manufacturer's instructions. RNAs were purified with RNeasy columns (Qiagen), eluted in cytoporation medium T and quantified by measuring absorbance at 260 nm using a Nanodrop ND-1000 spectrophotometer. Quality of the RNA was verified on a denaturing formaldehyde/MOPS agarose gel.

Transfection

T lymphocytes were transfected by electrotransfer of messenger RNA using an AgilePulse MAX system (Harvard Apparatus) 3 to 6 days after activation. Following removal of activation beads, cells were pelleted, resuspended in cytoporation medium T at >28×106 cells/ml. 5×106 cells were mixed with 6.9 μg total RNA (2.5 μg α chain, 1.9 μg β chain and 2.5 μg γ chain) or with 8.4 μg total RNA (4 μg modified α chain, 1.9 μg β chain and 2.5 μg γ chain) into a 0.4 cm cuvette. The electroporation consisted of two 0.1 ms pulses at 1200 V followed by four 0.2 ms pulses at 130V. Following electroporation, cells were diluted into 2 mL culture medium and incubated at 37° C./5% $CO_2$. 2 hours after mRNA electrotransfer, vehicle (DMSO) or Rapamycin (100 nM) was added for 19 hours.

Flow Cytometry

First labelling for the detection of the α-chain was performed with anti-Fab'2-Biotin (goat anti-mouse IgG, Fab'2 fragment specific, 115-066-072, Jackson Immunoresearch) in PBS FBS2%, EDTA 2 mM, azide 0.1% for 20 min at 4° C. followed by a two washing steps with PBS FBS2% EDTA 2 mM azide 0.1%. Second labelling was performed with Streptavidin-APC in PBS FBS2% EDTA 2 mM azide 0.1% for 20 min at 4° C. followed by a washing step in PBS FBS2% EDTA 2 mM azide 0.1% and a washing step in PBS. Cell viability was monitored using the efluor450 (ebioscience 65-0863-14) in PBS for 20 min 4° C., followed by a washing step with PBS FBS2% EDTA 2 mM azide 0.1% and fixed in 2% PFA. Flow cytometry was performed using the MACSQUANT (Miltenyi Biotec) and data analysis was performed with the FlowJo software.

Figure 3:
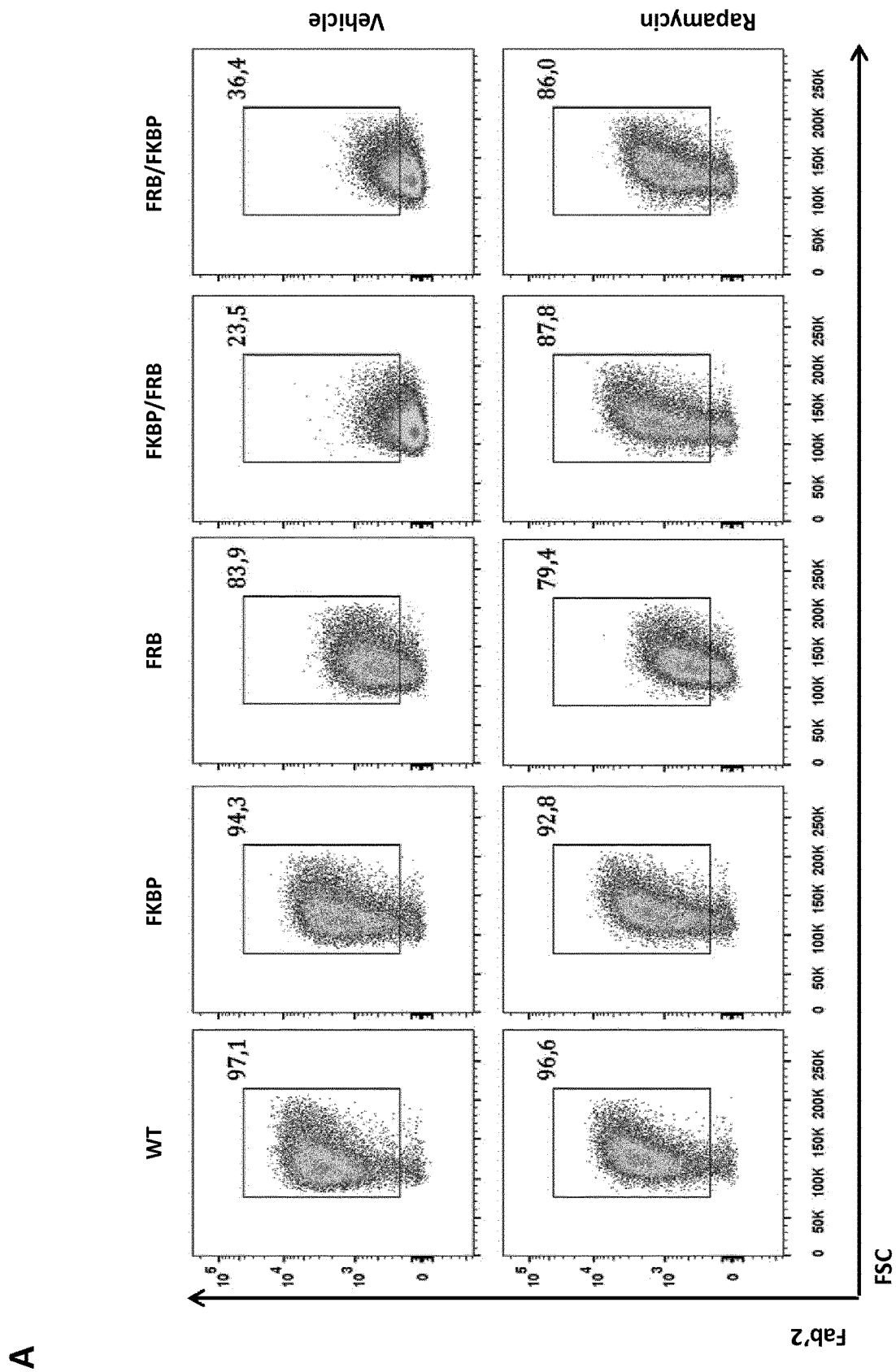
Figure 3:
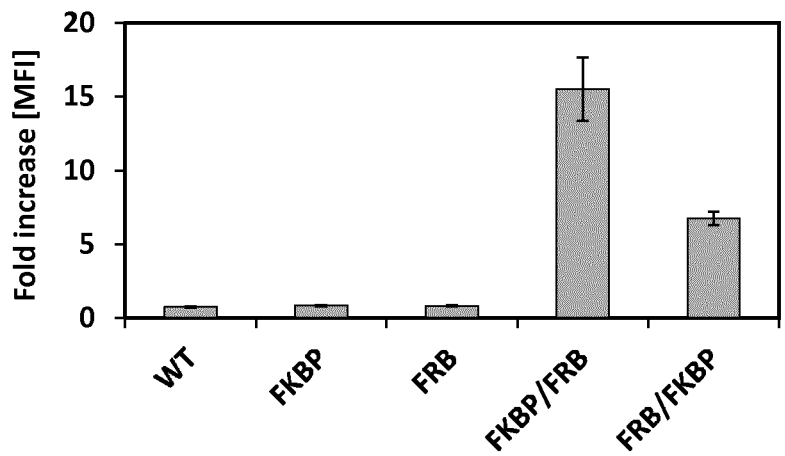

The data obtained clearly indicated an improved surface exposition in presence of rapamycin when the FRB-FKBP or the FKBP-FRB domains were incorporated in the α-chain (FIGS. 3A and B).

Example 2: Development of a Small Molecule (AP21967) Switch-on mcCARCD19—mRNA Delivery—Surface Detection Constructs, mRNA Preparation and Flow Cytometry To design an integrated system to switch the scFv/antigen interaction between on/off states, either the FRB, the FKBP12, or fusion of the FRB and FKBP12 were inserted between the CD8a hinge and the scFv domains (FIG. 1B). As a starting experiment, primary T cell with mRNAs encoding each chain of the multichain CAR (mcCAR) were transfected. Upon addition of rapamycin, changes in the detection of the extracellular hinge domain were monitored by tracking the Fab'2 domain of CD19-targeting scFv (100 nM, 20 h). In the absence of the small molecule (rapamycin), it was found that a high level of surface detection could only be achieved for the wild type mcCAR and the FKBP-mcCAR with above 90% of positive cells with an overall high MFI as shown in FIG. 3A. The presence of both FKBP and FRB in the stalk region virtually abolished surface detection of the CD19 ScFV, independently of their reciprocal position (below 40% of positive cells, with up to 40 fold decrease in MFI when compared to the mcCAR). Interestingly, while the addition of rapamycin barely effected the mcCAR, FRB-mcCAR and FKB-mcCAR constructs, when considering the percentage of positive cells or the MFI (FIG. 3B), it strongly improved (up to 15 fold when considering the MFI and 3 fold when considering the percentage of positive cell) the surface detection of the FKBP/FRB-mcCAR and FRB/FKBP-mcCAR constructs, turning the system from an off to an on state. This variation of detection upon addition of rapamycin may results from different factors, including stabilization of the CAR chain that is containing the switch on component. However it has to be noted that the small molecule was always required to efficiently turn-on the detection of the FKBP/FRB-CAR of the CAR at the surface of the T-cell.

Synthetic non-immunossupressing AP21967 rapamycin synthetic analog was also tested, which binds to the FKBP12 but does not promote the binding to the FRB domain of mTOR. Accordingly, T2098L mutation was introduced in the FRB domain (referred as FRB*) to allow the FKBP/AP21967/FRB* complex to be formed.

The T2098L mutation in the FRB domain was introduced in the FKBP-FRB domain using commercially available kits (Agilent) and standard molecular biology procedures leading to the FKBP-FRB* domain (SEQ ID NO: 62). Assembly of the alpha chain containing the scFv, the FKBP-FRB* domain, hinge-transmembrane-intracytoplasmic domain leaded to pCLS27039 (SEQ ID NO: 63). The amino acid sequence encoded by this construct is shown in SEQ ID NO: 64. FRB* refers to a variant of FRB having the T2098L mutation (SEQ ID NO: 4).

mRNA preparation, transfection and flow cytometry measurement of surface presentation was performed as described in example 1 using AP21967 instead of Rapamycin.

Figure 4:
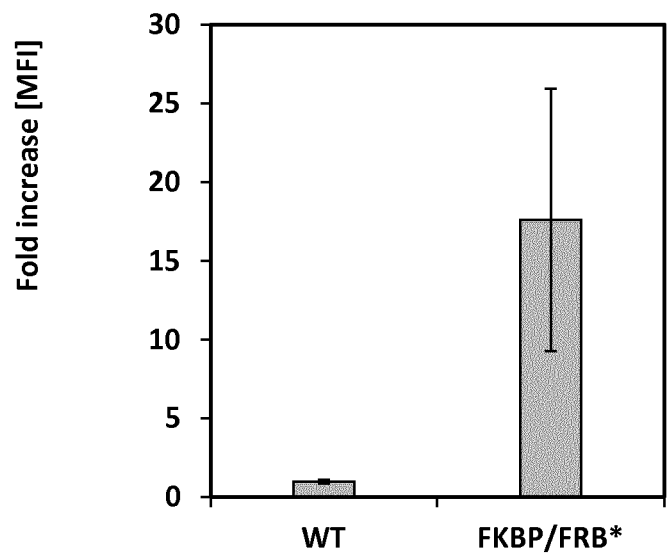
FIG. 4. Fold increase in the median fluorescence intensity (MFI) upon addition of the small molecule AP21967 used in association with the T2098L mutant FKBP/FRB* construct as depicted in the whole live cell population.

The data obtained clearly indicated an improved surface exposition in presence of AP21697 when the FKBP-FRB* domains was incorporated in the α-chain (FIG. 4).

Figure 8:
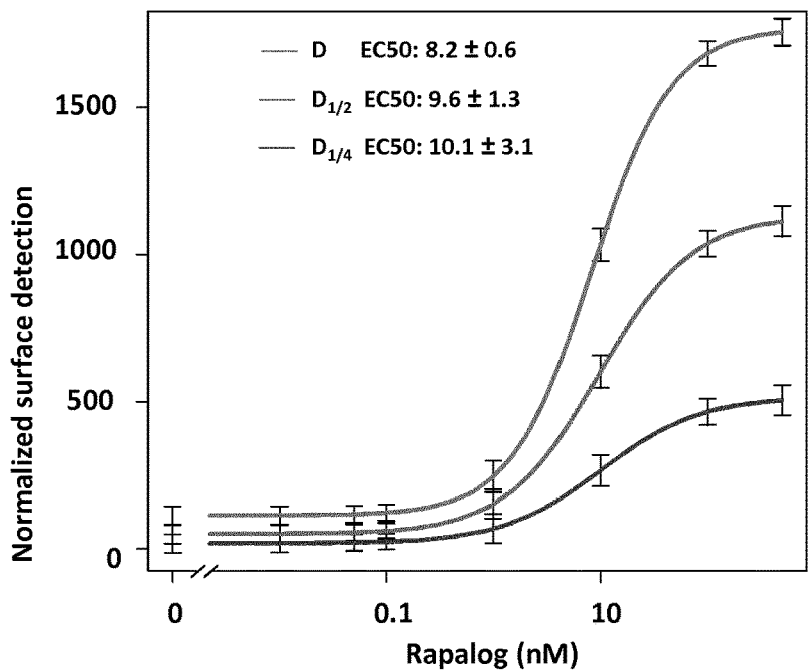
FIG. 8. (A) Determination of the AP21967 EC50 with CD19 targeting engineered CAR. T-cells transfected with three doses (D, $D_{1/2}$ and $D_{1/4}$) of mRNA coding for the engineered CAR were treated with increasing amount of AP21967 rapamycin synthetic analog. The Fab'2 region of the scFv is detected. (B) Determination of the AP21967 EC50 with CD123 targeting engineered mcCAR. T-cells transfected with three doses (D, $D_{1/2}$ and $D_{1/4}$) of mRNA coding for the engineered mcCAR were treated with increasing amount of AP21967 rapalog. The scFv is detected using a recombinant CD123 fused to an Fc fragment.
Figure 8:
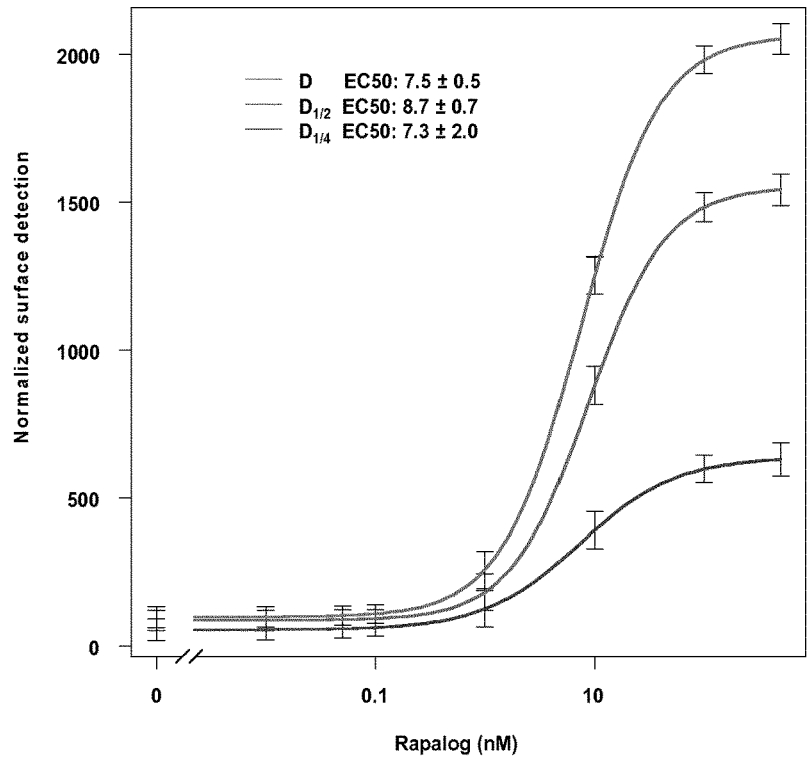

To evaluate the AP21967 usable dose range for the switch-on system a dose response assay was performed (FIG. 8A). The results obtained indicated a maximum signal induction at 100 nM and an EC50 value of approximately 10 nM (8.2-10.1 nM) that was independent from the amount of transfected engineered CAR. To validate the portability of the switch-on approach, a CAR targeting CD123 was also engineered. As demonstrated by a similar EC50 value of 10 nM (7.3-8.7 nM, FIG. 8B), it was found that the nature of the scFv did not influence the switch-on properties. Remarkably, the EC50s are in range with rapamycin concentrations reported in peripheral blood or tumor tissue of patients, suggesting that the switch-on system may be sensitive to clinically relevant concentration.

Example 3: Development of a Small Molecule (AP21967) Switch-on mcCAR—mRNA Delivery—Induced Cytotoxicity The cytolytic activity of engineered T-cells endowed with the FKBP-FRB* mcCAR CD19 from example 2, was assessed using a flow cytometry-based cytotoxicity assay. In this assay target cells presenting the CAR target antigen (Daudi CD19 positive) are labelled with CellTrace™ CFSE or and control cells with CellTrace™ violet. The mixed target cell populations (1:1 ratio) was co-incubate at 37° C. with various ratio of engineered effector CAR T cells (Effector/Target ratio of 20:1) in a final volume of X-Vivo-15 media 100 uL, for a fixed time periods (5 h) in presence of vehicle (Ethanol) or AP21967 (100 nM).

The whole cell population was recovered, washed in PBS and labeled with eFluor780 viability marker before being fixed by 2% PFA. Fixed cells were analyzed by flow cytometry to determine their viability. Flow cytometry and data analysis were performed as described in example 1.

Figure 5:
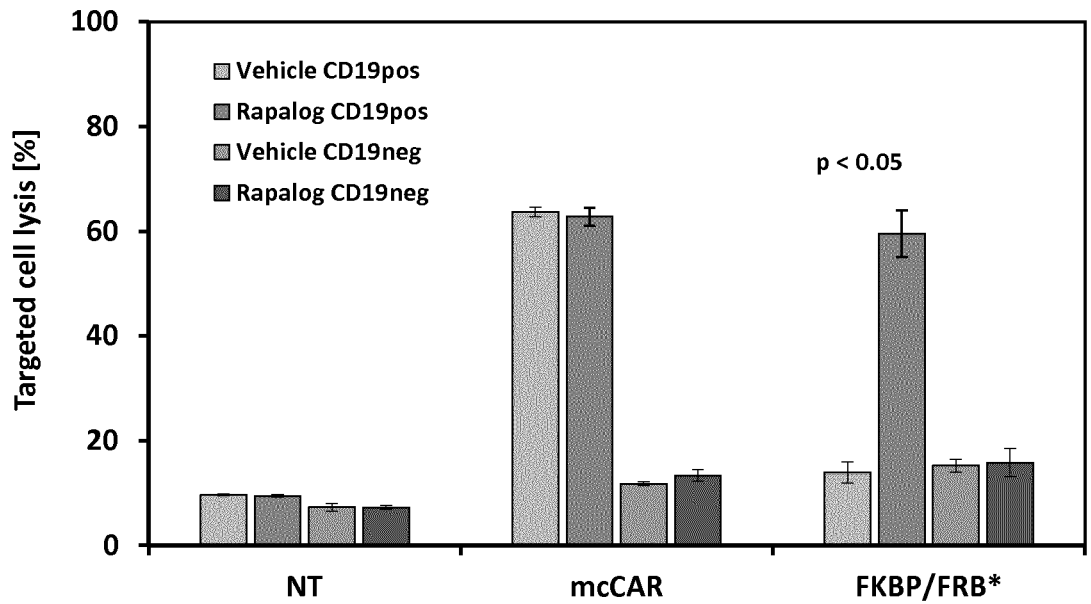
FIG. 5. (A) The effect of the AP21967 rapalog on the cytolytic capacities of the of the CAR T cells toward model antigen presenting cell was assessed in a flow-based cytotoxicity assay. The CD19pos and CD19neg target cell viability was measured after coculture with engineered CAR T-cells in presence or absence of AP21967. Effector/target ratios was set to 20:1. NT represents non-transfected T-cells. (B) Diagram showing the percentage of Daudi CD19 positive cell lysis when using increasing concentration of rapalog AP21967 as per the present invention to induce CAR activity.
Figure 5:
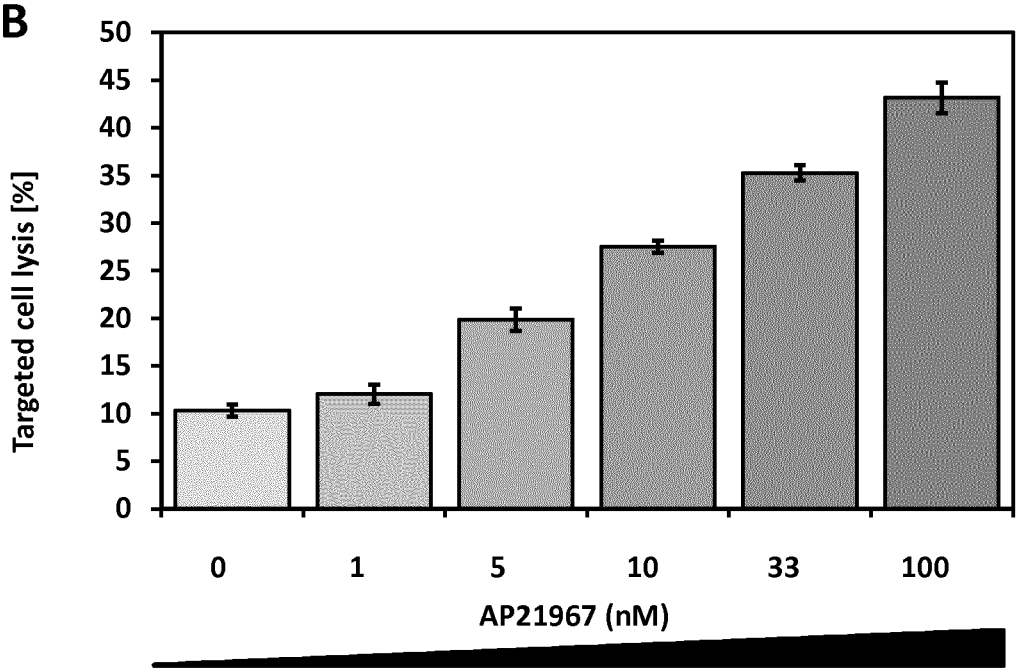

The data obtained clearly indicated an improved switched-on cytolytic activity in presence of AP21697 (FIG. 5A).

A dose response was also performed (0, 1, 5, 10, 33, 100 nM) of the AP21967 and measured the resulting cytolytic capacities of the engineered CAR T-cells. It resulted that the level of target cell killing correlated, as expected, with variation of the AP21967 (FIG. 5B). It was calculated an EC50 of approximately 10 nM (12.7 nM), in range of the one determined using the surface detection. The level of targeted cell killing also correlated with the level of CAR detection (FIG. 9).

All together, the results presented here provide the proof of principle of engineering the hinge domain of a CAR molecule to create an integrated switch-on system for logic gating strategies.

Example 4: Development of a Small Molecule (AP21967) Switch-on mcCAR—mRNA Delivery—Other Small Molecule Competition Tuning mRNA preparation, transfection and flow cytometry measurement of surface presentation was performed as described in example 2, incubating transfected T-cells simultaneously with 10 nM of AP21967 and increasing amounts Tacrolimus.

Conditions: AP21967: 10 nM, Tacrolimus: 0 nM, 10 nM, 30 nM, 100 nM or 500 nM. T-cells were incubated for 20 hours at 37° C./5% CO2.

Figure 6:
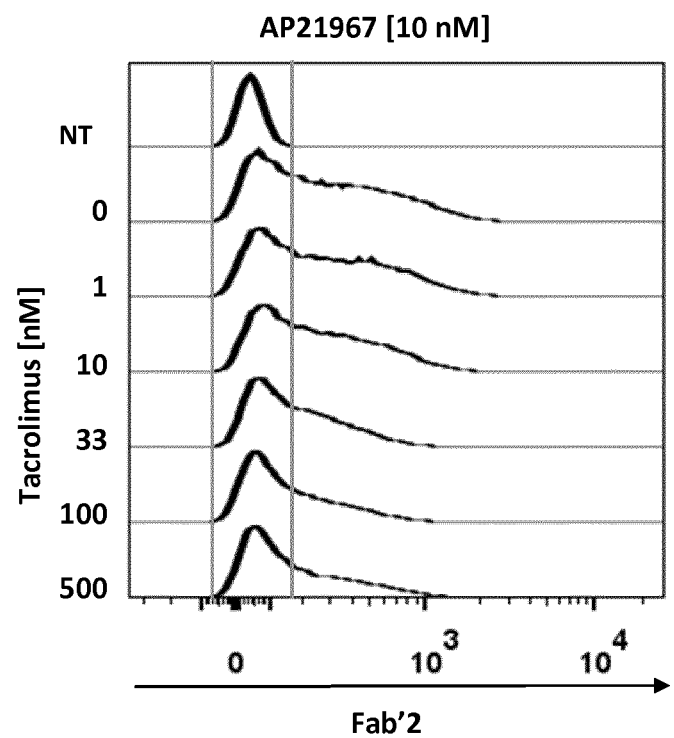
FIG. 6. Competition experiment between AP21967 (10 nM) and tacrolimus (0 to 500 nM) as described in Example 3.

The data obtained clearly indicated the possibility to tune the surface presentation of the engineered CAR, due to the small molecule AP21967, with a second small molecule (Tacrolimus) when the FKBP-FRB* domains was incorporated in the α-chain (FIG. 6).

Example 5: Development of a Small Molecule (AP21967) Switch-on scCAR—mRNA Delivery—Surface Detection The CAR extracellular domains (alpha chain) presented in example 2 were used as template to prepare plasmid DNA encoding single chain CARs (scCARs). The CD8 alpha transmembrane domain (SEQ ID NO: 32), the intracytoplasmic signalling region of the ζ-chain of the CD3-T cell receptor (SEQ ID NO: 28) and the signalling domains from co-stimulatory 4-1BB (CD137) (SEQ ID NO:31) were used to complete the CARs. scCARs were assemble by Golden Gate cloning using round of restriction and ligation, according to standard molecular biology procedures, leading to pCLS27572 (FKBP-FRB*) (SEQ ID NO:65), pCLS27603 (FKBP) (SEQ ID NO:66), pCLS27604 (FRB*) (SEQ ID NO:67). The respective amino acid sequences encoded by these constructs are shown in SEQ ID NOs: 68 to 70.

mRNA preparation (using oligo pair scCAR-F (SEQ ID NO: 71) and scCAR-R (SEQ ID NO: 72) that are located in the CAR and on the plasmid respectively) and transfection and flow cytometry measurement of surface presentation was performed as described in example 1 using AP21967 instead of Rapamycin. Primary labelling for the detection of the scCARs was performed with Fc-tagged recombinant CD123 (Lake Pharma) in PBS FBS2%, EDTA 2 mM, azide 0.1% for 20 min at 4° C. followed by a two washing steps with PBS FBS2% EDTA 2 mM azide 0.1%. Secondary labelling was performed with PE labeled Goat Anti-Mouse IgG (subclasses 1+2a+2b+3) Fcγ Fragment Specific (Jackson Immunoresearch) in PBS FBS2% EDTA 2 mM azide 0.1% for 20 min at 4° C. followed by a washing step in PBS FBS2% EDTA 2 mM azide 0.1% and a washing step in PBS. Following the extracellular labelling, the cell viability was monitored using the efluor450 or efluor780 (ebioscience) in PBS for 20 min 4° C., followed by a washing step with PBS FBS2% EDTA 2 mM azide 0.1% and fixed in PFA 2%.

Figure 7:
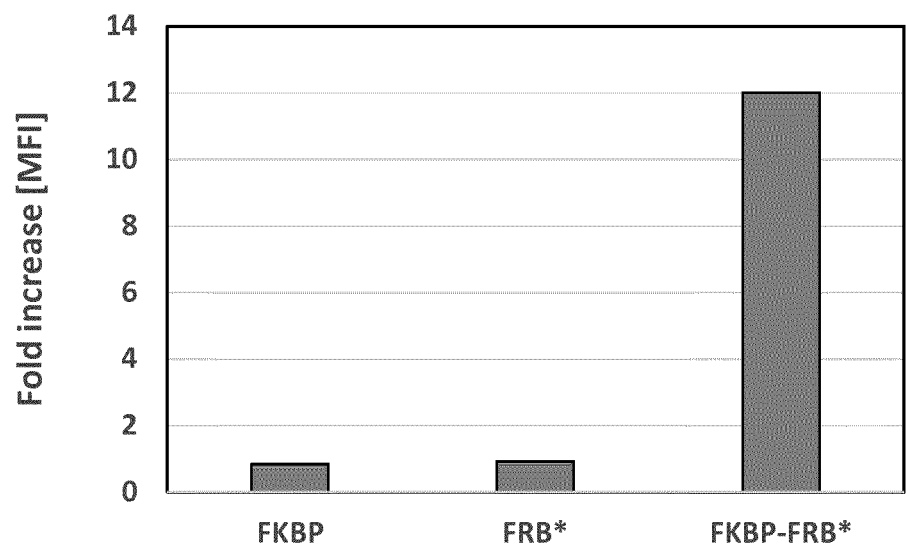
FIG. 7. Fold increase in the median fluorescence intensity (MFI) upon addition of the small molecule AP21967 used in association with the T2098L mutant FKBP/FRB* construct as depicted in the whole live cell population.

The data obtained clearly indicated an improved surface exposition in presence of AP21697 when the FKBP-FRB* domains was incorporated in the α-chain (FIG. 7).

Example 6: Development of a Small Molecule (Rapamycin) Switch-on mcCAR in Combination with mTOR Genome Editing Rapamycin directly inhibit T cells through interaction with the cytosolic protein FK-binding protein 12 (FKBP12) followed by inhibition of mTOR by the FKBP12/rapamycin complex.

Designer nucleases that create a single or a double strand break that target the sequence surrounding the triplet (or the triplet itself) coding for the amino acid (Serine) 2035 of Serine/threonine-protein kinase mTOR are designed and constructed/produced. To perform the gene correction/mutation of position 2035, a donor DNA containing the desired mutated base(s) surrounded by two homology arms of the endogenous sequence was designed. Additional silent mutations are added to prevent cleavage of the donor DNA, or the corrected/mutated genomic DNA by the designer nuclease.

T cells are transfected or transduced with genetic material coding for the designer nuclease and the donor DNA. T cells that contained the desired mutation at the endogenous locus are then selected or isolated. Improved expansion properties of the engineered T cell in presence of rapamycin are recorded and compared to the non-engineered T cell.

The switch on CARs presented in example 1 are then implemented in the newly engineered T cells and improved surface presentation of the CARs and cytolytic properties in presence of rapamycin is recorded.

Example 7: Development of a Small Molecule (Rapamycin) Switch-on mcCAR in Combination with FKBP12 Genome Editing (Knock-Out Rapamycin directly inhibit T cells through interaction with the cytosolic protein FK-binding protein 12 (FKBP12) followed by inhibition of mTOR by the FKBP12/rapamycin complex.

Designer nucleases that create a double strand break that target the sequence of the FKBP12 gene are designed and constructed/produced. T cells are transfected or transduced with genetic material coding for the designer nuclease. T cells that contained the desired knock-out at the endogenous locus are then selected or isolated. Improved expansion properties of the engineered T cell in presence of rapamycin are recorded and compared to the non-engineered T cell.

The switch on CARs presented in example 1 are then implemented in the newly engineered T cells and improved surface presentation of the CARs and cytolytic properties in presence of rapamycin is recorded.

Example 8: Antitumor Activity Study of Human Modified Inducible CD123 CAR+ T Cells in Nog Mice Intravenously Injected with Molm13-Luc Tumor Cells The aim of the study was to demonstrate the anti-tumor activity in vivo of human T-cells genetically modified by Cellectis to express an inducible Chimeric Antigen Receptors (CAR) directed against the human CD123 antigen. This inducible system works with a non-immunosupressing rapamycin synthetic analog (AP21967, developed by ARIAD, #635055).

Figure 10:
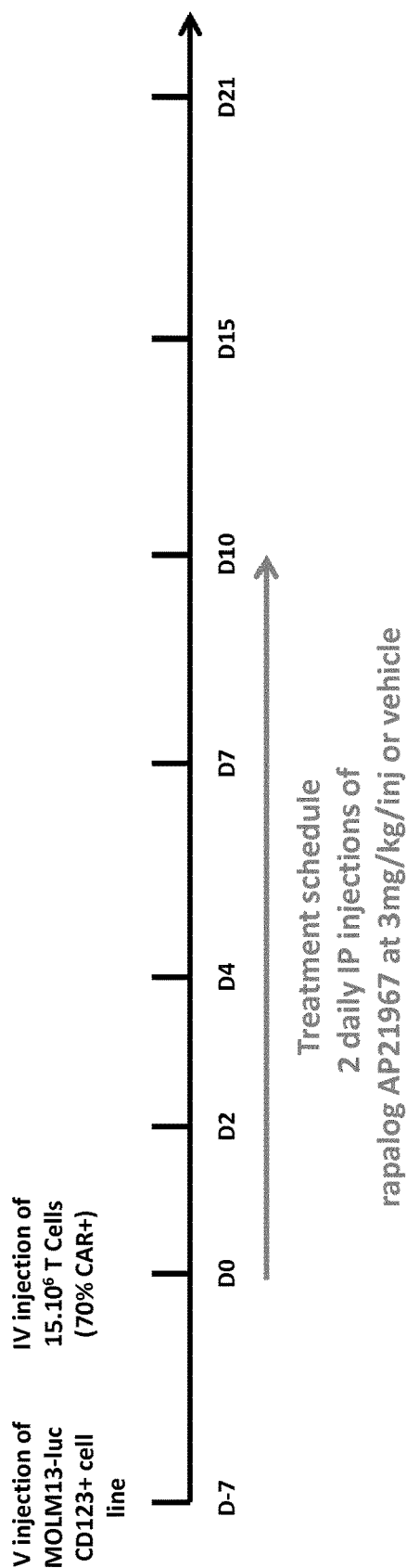
FIG. 10. Treatment schedule of MOLM-13-Luc treated with T cells CAR CD123+ in conjunction with repeated doses of rapalog AP21967 as described in Example 8.

The anti-tumor activity of human T-cells expressing a switch-on mcCAR-CD123 as described in Example 1, was assessed in NOG mice intravenously injected with MOLM13-Luc tumour cells. Repeated injections of rapamycin synthetic analog AP21967 was performed as shown in FIG. 10 (3 mg/kg/inj) into the peritoneal cavity of mice (Intraperitoneally, IP).

To establish the MOLM13-Luc cell line, MOLM13 cells (DSMZ ACC 554) have been transduced with a lentivirus encoding the GFP and the firefly luciferase (amsbio LVP438-PBS). The GFP-positive cells have been selected with Neomycin (ref 10131-027, Gibco, Life Technologies, Saint-Aubin, France). MOLM13-Luc cells are grown in suspension at 37° C. in a humidified atmosphere (5% CO2, 95% air) into culture medium RPMI 1640 containing 2.05 mM L-glutamine (ref: BE12-702F, Lonza) supplemented with 15% fetal bovine serum (ref: 3302, Lonza, Verviers, Belgium), 100 U/mL Penicillin and 100 µg/mL Streptomycin (ref: DE17-602E, Lonza). The cells are counted in a hemocytometer and their viability is assessed by 0.25% trypan blue exclusion assay and are passed twice weekly (0.8 millions/mL) in fresh culture medium.

The day of injection to mice, frozen human T-cells transformed with the switch-on mcCAR-CD123 CAR are assessed to be within a range of 1-2.106 live cells per mL.

Eighteen (18) healthy female NOG (NOD.Cg-PrkdcscidIl2rgtm1Sug/JicTac) mice, 7-8 weeks old, were obtained from Taconic (Ry, Danemark) and bred according to NRC Guide for the Care and Use of Laboratory Animals.

The intravenous injection of MOLM13-Luc cells (0.25× 106 cells/mouse) were performed on D-7.

The cell injection and treatment were scheduled as follows:
Group 1 (No transduced T cells/Vehicle) will receive a single IV injection of x No transduced T-cells (200 µL in RPMI 1640) on D0, followed by 2 daily IP injections of vehicle for 10 consecutive days (2Q1D×10),
Group 2 (No transduced T cells/AP21967) will receive a single IV injection of x No transduced T-cells (200 µL in RPMI 1640) on D0, followed by 2 daily IP injections of AP21967 at 3 mg/kg/inj for 10 consecutive days (2Q1D× 10),
Group 3 (CAR T cells/Vehicle) will receive a single IV injection of x modified CAR T-cells including X CAR-positive T-cells (200 µL in RPMI 1640) on D0, followed by 2 daily IP injections of vehicle for 10 consecutive days (2Q1D×10),
Group 4 (CAR T cells/AP21967) will receive a single IV injection of x modified CAR T-cells including X CAR-positive T-cells (200 µL in RPMI 1640) on D0, followed by 2 daily IP injections of AP21967 for 10 consecutive days (2Q1D×10).

T cell injection took place at D0, D2, D4, D7, D10, D15 and D21, while the mice were injected twice a day with rapalog.

Figure 11:
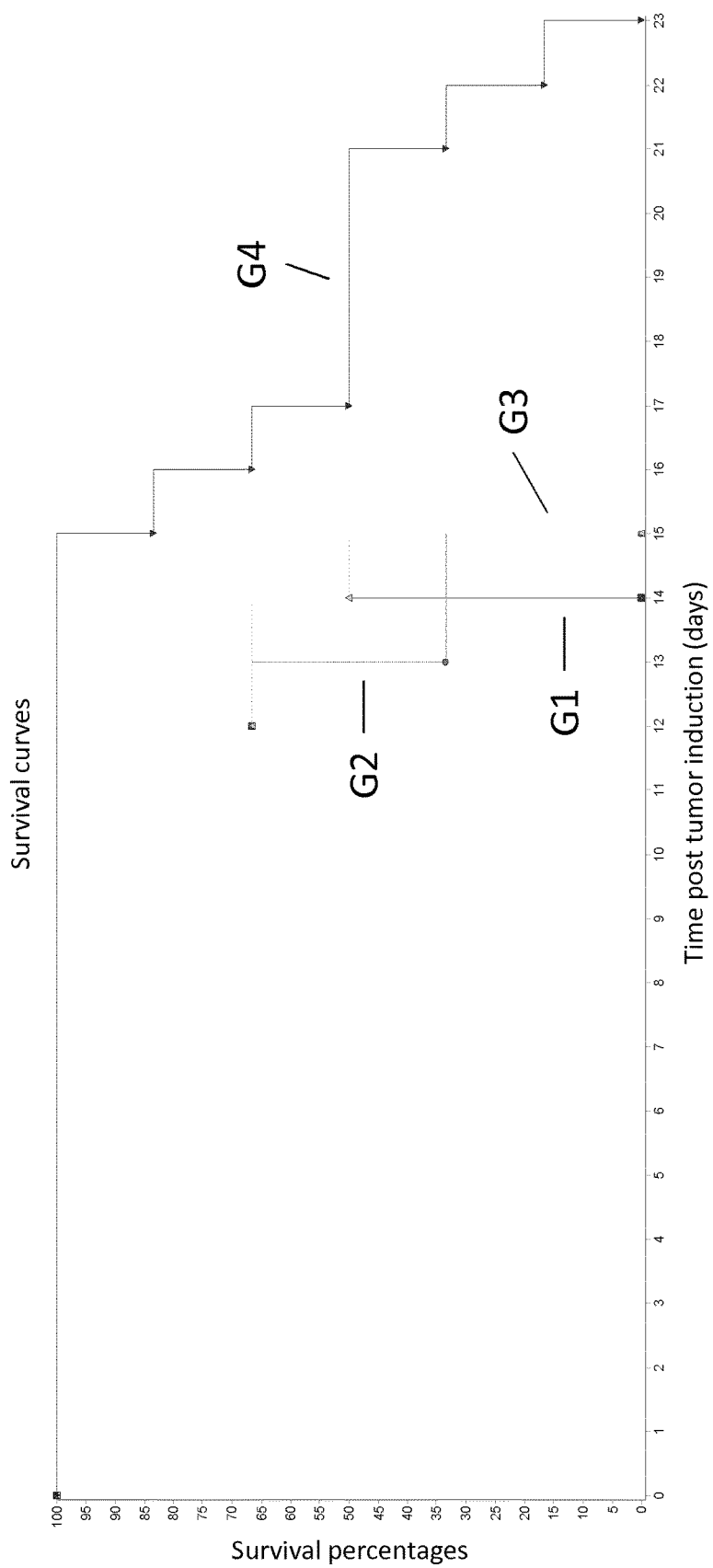
FIG. 11. Survival curve of MOLM-13-Luc mice following treatment as illustrated in FIG. 10 and Example 8.
Figure 12:
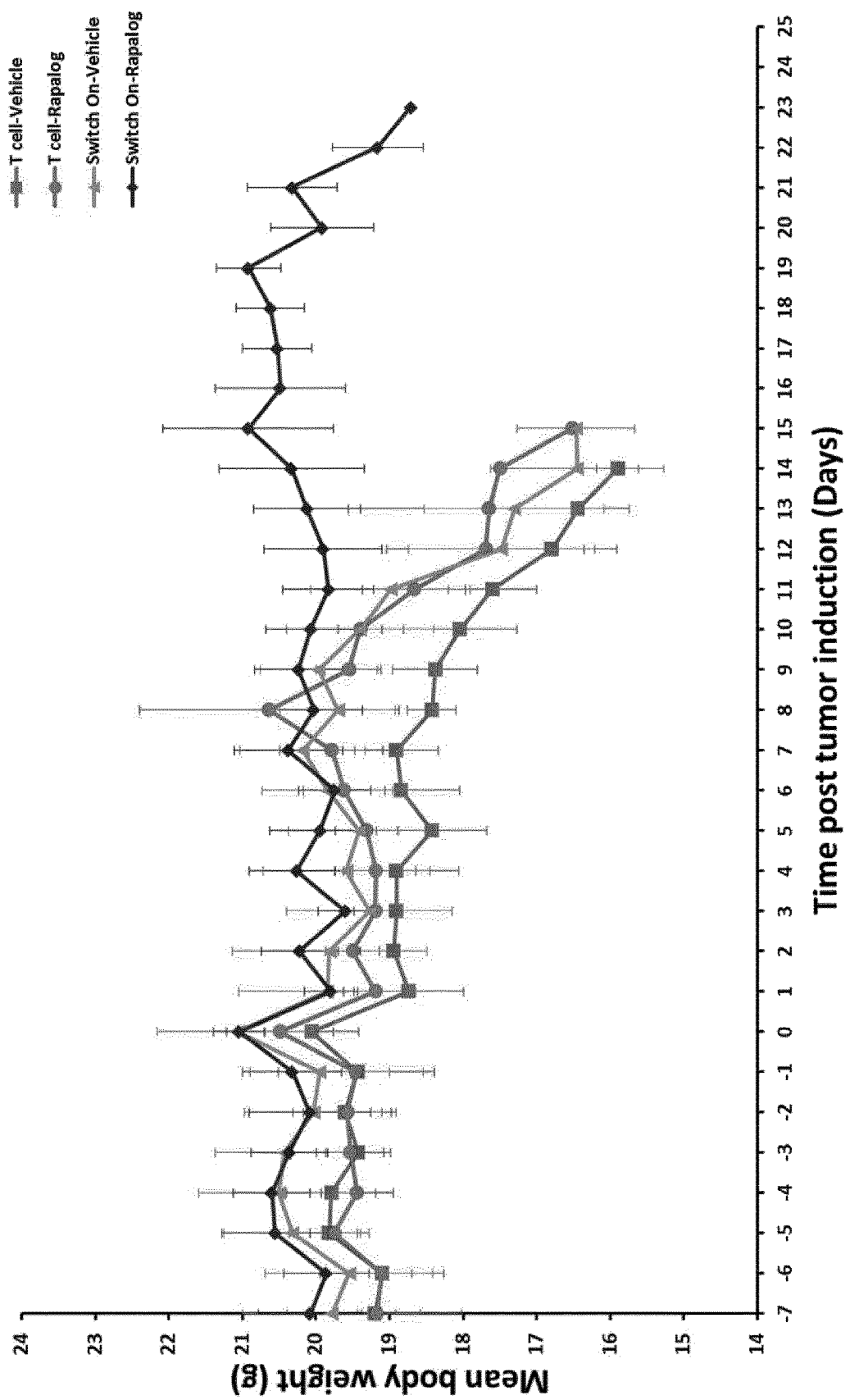
FIG. 12. Graph body weight of MOLM-13-Luc mice following treatment as illustrated in FIG. 10 and Example 8.

Mice were monitored daily with respect to their body weight measurements, clinical and mortality records, and treatment were recorded on Vivo Manager® database (Biosystemes, Dijon, France). Survival curves and Graph body weight are respectively reported in FIG. 11 and FIG. 12, from where it is apparent that the mcCAR-CD123 CAR induced by AP21967 increased the survival of the mice.

REFERENCES

Cruz, C. R. et al. (2013), "Infusion of donor-derived CD19-redirected virus-specific T cells for B-cell malignancies relapsed after allogeneic stem cell transplant: a phase 1 study", Blood, 122(17): 2965-73

Erhart, D. et al. (2013), "Chemical development of intracellular protein heterodimerizers", Chemistry & Biology, 20: 549-557.

Gaultier, A. et al. (2009), "Selective cross-linking of interacting proteins using self-labeling tags", J Am Chem Soc., 131(49):17954-62.

Gallagher, S. S. et al. (2007) "An orthogonal dexamethasone-trimethoprim yeast three-hybrid system", Anal Biochem. 363(1):160-2.

Jena, B., G. Dotti, et al. (2010). "Redirecting T-cell specificity by introducing a tumor-specific chimeric antigen receptor." Blood, 116(7): 1035-44.

Kopytek, S. J. (2000), "Chemically induced dimerization of dihydrofolate reductase by a homobifunctional dimer of methotrexate", Chemistry & Biology, 7:313-321.

Lin, H. N., et al. (2000), "Dexamethasone-methotrexate: An efficient chemical inducer of protein dimerization in vivo", Journal of the American Chemical Society, 122 (17):4247-4248.

Park, T. S., S. A. Rosenberg, et al. (2011). "Treating cancer with genetically engineered T cells." Trends Biotechnol, 29(11): 550-7.

Peipp, M., D. Saul, et al. (2004). "Efficient eukaryotic expression of fluorescent scFv fusion proteins directed against CD antigens for FACS applications." J Immunol Methods, 285(2): 265-80.

Poirot, L. et al. (2015), "Multiplex genome edited T-cell manufacturing platform for "off-the-shelf" adoptive T-cell immunotherapies", J. Cancer Res. 2015 Jul. 16. [Epub ahead of print]

Swarts, D. C. et al. (2014), "The evolutionary journey of Argonaute proteins". Nat Struct Mol Biol., 21(9):743-53

Valton, J. et al. (2015), "A Multidrug-resistant Engineered CAR T Cell for Allogeneic Combination Immunotherapy", Mol Ther. 2015 Jun. 10. [Epub ahead of print]

Wilson, K. P. et al. (1995), "Comparative X-ray structures of the major binding protein for the immunosuppressant FK506 (tacrolimus) in unliganded form and in complex with FK506 and rapamycin", Acta. Crystallogr. D Biol. Crystallogr. 51: 511-521

---

The invention claimed is:

1. A single chain chimeric antigen receptor (CAR) characterized in that it comprises:
   a) at least one ectodomain which comprises:
      i) an extracellular antigen binding domain; and
      ii) a switch domain comprising at least a first multimerizing ligand-binding domain and a second multimerizing ligand-binding domain which are capable of binding to a predetermined multivalent ligand to form a multimer comprising said two binding domains and the multivalent ligand to which they are capable of binding;
   b) at least one transmembrane domain; and
   c) at least one endodomain comprising a signal transducing domain and optionally a co-stimulatory domain;
   wherein the switch domain is located between the extracellular antigen binding domain and the transmembrane domain.

2. The chimeric antigen receptor according to claim 1, wherein the first multimerizing ligand-binding domain and second multimerizing ligand-binding domain comprise a chemical induced dimerization (CID) system.

3. The chimeric antigen receptor according to claim 1, wherein the first multimerizing ligand-binding domain and second multimerizing ligand-binding domain are different.

4. The chimeric antigen receptor according to claim 1, wherein the first multimerizing ligand-binding domain and second multimerizing ligand-binding domain are selected from the pairs of multimerizing ligand-binding domains consisting of:
   SEQ ID NO:1: SEQ ID NO:2;
   SEQ ID NO:1:SEQ ID NO:1;
   SEQ ID NO:3:SEQ ID NO:3;
   SEQ ID NO:1:SEQ ID NO:4;
   SEQ ID NO:1:SEQ ID NO:5;
   SEQ ID NO:1:SEQ ID NO:6;
   SEQ ID NO:7:SEQ ID NO:7;
   SEQ ID NO:8:SEQ ID NO:9;
   SEQ ID NO:8:SEQ ID NO:10;
   SEQ ID NO:8:SEQ ID NO:11;
   SEQ ID NO:12:SEQ ID NO:13;
   SEQ ID NO:12:SEQ ID NO:14;
   SEQ ID NO:15:SEQ ID NO:15;
   SEQ ID NO:16:SEQ ID NO:15; and
   SEQ ID NO:17:SEQ ID NO:18.

5. The chimeric antigen receptor according to claim 1, wherein the first multimerizing ligand-binding domain is SEQ ID NO: 1 or a variant thereof having at least 80% sequence identity with SEQ ID NO: 1.

6. The chimeric antigen receptor according to claim 1, wherein the second multimerizing ligand-binding domain is SEQ ID NO: 1 or a variant thereof having at least 80% sequence identity with SEQ ID NO: 1.

7. The chimeric antigen receptor according to claim 5, wherein the second multimerizing ligand-binding domain is SEQ ID NO: 2 or a variant thereof having at least 80% sequence identity with SEQ ID NO: 2.

8. The chimeric antigen receptor according to claim 5, wherein the second multimerizing ligand-binding domain is SEQ ID NO:4.

9. The chimeric antigen receptor according to claim 1, wherein the first multimerizing ligand-binding domain is SEQ ID NO: 3 and the second multimerizing ligand-binding domain is SEQ ID NO: 3.

10. The chimeric antigen receptor according to claim 1, wherein the first and second multimerizing ligand-binding domains are separated by a peptide linker.

11. The chimeric antigen receptor according to claim 1, wherein the first and second multimerizing ligand-binding domains are in direct fusion.

12. The chimeric antigen receptor according to claim 1, wherein the first multimerizing ligand-binding domain is located N-terminal to the second multimerizing ligand-binding domain.

13. The chimeric antigen receptor according to claim 1, wherein the first multimerizing ligand-binding domain is located C-terminal to the second multimerizing ligand-binding domain.

14. The chimeric antigen receptor according to claim 1, wherein said at least one ectodomain comprises (iii) a hinge which is located between the switch domain and the transmembrane domain.

15. The chimeric antigen receptor according to claim 14, wherein the hinge is selected from the group consisting of CD8α hinge, IgG1 hinge and FcγRIIIα hinge.

16. The chimeric antigen receptor according to claim 1, wherein the signal transducing domain is a TCRzeta, FcRgamma, FcRbeta, FcRepsilon, CD3gamma, CD3delta, CD3epsilon, CD3 zeta, CD5, CD22, CD79a, CD79b or CD66d signal transducing domain.

17. The chimeric antigen receptor according to claim 1, wherein the signaling domain comprises a CD3 zeta signaling domain.

* * * * *

SEQUENCE LISTING

<160> NUMBER OF SEQ ID NOS: 72

<210> SEQ ID NO 1
<211> LENGTH: 108
<212> TYPE: PRT
<213> ORGANISM: Homo sapiens

<400> SEQUENCE: 1

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
 50                  55                  60

Ala Gln Met Ser Val Gly Gln Arg Ala Lys Leu Thr Ile Ser Pro Asp
 65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 2
<211> LENGTH: 94
<212> TYPE: PRT
<213> ORGANISM: Homo sapiens

<400> SEQUENCE: 2

Arg Val Ala Ile Leu Trp His Glu Met Trp His Glu Gly Leu Glu Glu
 1               5                  10                  15

Ala Ser Arg Leu Tyr Phe Gly Glu Arg Asn Val Lys Gly Met Phe Glu
            20                  25                  30

Val Leu Glu Pro Leu His Ala Met Met Glu Arg Gly Pro Gln Thr Leu
        35                  40                  45

Lys Glu Thr Ser Phe Asn Gln Ala Tyr Gly Arg Asp Leu Met Glu Ala
 50                  55                  60

Gln Glu Trp Cys Arg Lys Tyr Met Lys Ser Gly Asn Val Lys Asp Leu
 65                  70                  75                  80

Thr Gln Ala Trp Asp Leu Tyr Tyr His Val Phe Arg Arg Ile
                85                  90

<210> SEQ ID NO 3
<211> LENGTH: 107
<212> TYPE: PRT
<213> ORGANISM: Artificial Sequence
<220> FEATURE:
<223> OTHER INFORMATION: FKBP12 (F36V)

<400> SEQUENCE: 3

Gly Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 4
<211> LENGTH: 94

```
<212> TYPE: PRT
<213> ORGANISM: Artificial Sequence
<220> FEATURE:
<223> OTHER INFORMATION: FRB T2098L

<400> SEQUENCE: 4

Arg Val Ala Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
            20                  25                  30

Val Leu Glu Pro Leu His Ala Met Met Glu Arg Gly Pro Gln Thr Leu
        35                  40                  45

Lys Glu Thr Ser Phe Asn Gln Ala Tyr Gly Arg Asp Leu Met Glu Ala
50                  55                  60

Gln Glu Trp Cys Arg Lys Tyr Met Lys Ser Gly Asn Val Lys Asp Leu
65                  70                  75                  80

Leu Gln Ala Trp Asp Leu Tyr Tyr His Val Phe Arg Arg Ile
            85                  90

<210> SEQ ID NO 5
<211> LENGTH: 344
<212> TYPE: PRT
<213> ORGANISM: Homo sapiens

<400> SEQUENCE: 5

Glu Val Phe Asp Asn Asp Gly Lys Pro Arg Val Asp Ile Leu Lys Ala
1               5                   10                  15

His Leu Met Lys Glu Gly Arg Leu Glu Glu Ser Val Ala Leu Arg Ile
            20                  25                  30

Ile Thr Glu Gly Ala Ser Ile Leu Arg Gln Glu Lys Asn Leu Leu Asp
        35                  40                  45

Ile Asp Ala Pro Val Thr Val Cys Gly Asp Ile His Gly Gln Phe Phe
50                  55                  60

Asp Leu Met Lys Leu Phe Glu Val Gly Gly Ser Pro Ala Asn Thr Arg
65                  70                  75                  80

Tyr Leu Phe Leu Gly Asp Tyr Val Asp Arg Gly Tyr Phe Ser Ile Glu
            85                  90                  95

Cys Val Leu Tyr Leu Trp Ala Leu Lys Ile Leu Tyr Pro Lys Thr Leu
            100                 105                 110

Phe Leu Leu Arg Gly Asn His Glu Cys Arg His Leu Thr Glu Tyr Phe
        115                 120                 125

Thr Phe Lys Gln Glu Cys Lys Ile Lys Tyr Ser Glu Arg Val Tyr Asp
    130                 135                 140

Ala Cys Met Asp Ala Phe Asp Cys Leu Pro Leu Ala Ala Leu Met Asn
145                 150                 155                 160

Gln Gln Phe Leu Cys Val His Gly Gly Leu Ser Pro Glu Ile Asn Thr
            165                 170                 175

Leu Asp Asp Ile Arg Lys Leu Asp Arg Phe Lys Glu Pro Pro Ala Tyr
        180                 185                 190

Gly Pro Met Cys Asp Ile Leu Trp Ser Asp Pro Leu Glu Asp Phe Gly
    195                 200                 205

Asn Glu Lys Thr Gln Glu His Phe Thr His Asn Thr Val Arg Gly Cys
210                 215                 220

Ser Tyr Phe Tyr Ser Tyr Pro Ala Val Cys Glu Phe Leu Gln His Asn
225                 230                 235                 240

Asn Leu Leu Ser Ile Leu Arg Ala His Glu Ala Gln Asp Ala Gly Tyr
```

-continued

```
                245                 250                 255
Arg Met Tyr Arg Lys Ser Gln Thr Thr Gly Phe Pro Ser Leu Ile Thr
            260                 265                 270

Ile Phe Ser Ala Pro Asn Tyr Leu Asp Val Tyr Asn Lys Ala Ala
        275                 280                 285

Val Leu Lys Tyr Glu Asn Asn Val Met Asn Ile Arg Gln Phe Asn Cys
    290                 295                 300

Ser Pro His Pro Tyr Trp Leu Pro Asn Phe Met Asp Val Phe Thr Trp
305                 310                 315                 320

Ser Leu Pro Phe Val Gly Glu Lys Val Thr Glu Met Leu Val Asn Val
                325                 330                 335

Leu Asn Ile Cys Ser Asp Asp Glu
            340
```

<210> SEQ ID NO 6
<211> LENGTH: 165
<212> TYPE: PRT
<213> ORGANISM: Homo sapiens

<400> SEQUENCE: 6

```
Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
            165
```

<210> SEQ ID NO 7
<211> LENGTH: 804
<212> TYPE: PRT
<213> ORGANISM: Escherichia coli

<400> SEQUENCE: 7

```
Met Ser Asn Ser Tyr Asp Ser Ser Ile Lys Val Leu Lys Gly Leu
1               5                   10                  15

Asp Ala Val Arg Lys Arg Pro Gly Met Tyr Ile Gly Asp Thr Asp Asp
            20                  25                  30

Gly Thr Gly Leu His His Met Val Phe Glu Val Val Asp Asn Ala Ile
        35                  40                  45

Asp Glu Ala Leu Ala Gly His Cys Lys Glu Ile Ile Val Thr Ile His
```

```
        50                  55                  60
Ala Asp Asn Ser Val Ser Val Gln Asp Asp Gly Arg Gly Ile Pro Thr
 65                  70                  75                  80

Gly Ile His Pro Glu Glu Gly Val Ser Ala Ala Glu Val Ile Met Thr
                 85                  90                  95

Val Leu His Ala Gly Gly Lys Phe Asp Asp Asn Ser Tyr Lys Val Ser
            100                 105                 110

Gly Gly Leu His Gly Val Gly Val Ser Val Val Asn Ala Leu Ser Gln
        115                 120                 125

Lys Leu Glu Leu Val Ile Gln Arg Glu Gly Lys Ile His Arg Gln Ile
130                 135                 140

Tyr Glu His Gly Val Pro Gln Ala Pro Leu Ala Val Thr Gly Glu Thr
145                 150                 155                 160

Glu Lys Thr Gly Thr Met Val Arg Phe Trp Pro Ser Leu Glu Thr Phe
                165                 170                 175

Thr Asn Val Thr Glu Phe Glu Tyr Glu Ile Leu Ala Lys Arg Leu Arg
            180                 185                 190

Glu Leu Ser Phe Leu Asn Ser Gly Val Ser Ile Arg Leu Arg Asp Lys
        195                 200                 205

Arg Asp Gly Lys Glu Asp His Phe His Tyr Glu Gly Gly Ile Lys Ala
210                 215                 220

Phe Val Glu Tyr Leu Asn Lys Asn Lys Thr Pro Ile His Pro Asn Ile
225                 230                 235                 240

Phe Tyr Phe Ser Thr Glu Lys Asp Gly Ile Gly Val Glu Val Ala Leu
                245                 250                 255

Gln Trp Asn Asp Gly Phe Gln Glu Asn Ile Tyr Cys Phe Thr Asn Asn
            260                 265                 270

Ile Pro Gln Arg Asp Gly Thr His Leu Ala Gly Phe Arg Ala Ala
        275                 280                 285

Met Thr Arg Thr Leu Asn Ala Tyr Met Asp Lys Glu Gly Tyr Ser Lys
290                 295                 300

Lys Ala Lys Val Ser Ala Thr Gly Asp Asp Ala Arg Glu Gly Leu Ile
305                 310                 315                 320

Ala Val Val Ser Val Lys Val Pro Asp Pro Lys Phe Ser Ser Gln Thr
                325                 330                 335

Lys Asp Lys Leu Val Ser Ser Glu Val Lys Ser Ala Val Glu Gln Gln
            340                 345                 350

Met Asn Glu Leu Leu Ala Glu Tyr Leu Leu Glu Asn Pro Thr Asp Ala
        355                 360                 365

Lys Ile Val Val Gly Lys Ile Ile Asp Ala Ala Arg Ala Arg Glu Ala
370                 375                 380

Ala Arg Arg Ala Arg Glu Met Thr Arg Arg Lys Gly Ala Leu Asp Leu
385                 390                 395                 400

Ala Gly Leu Pro Gly Lys Leu Ala Asp Cys Gln Glu Arg Asp Pro Ala
                405                 410                 415

Leu Ser Glu Leu Tyr Leu Val Glu Gly Asp Ser Ala Gly Gly Ser Ala
            420                 425                 430

Lys Gln Gly Arg Asn Arg Lys Asn Gln Ala Ile Leu Pro Leu Lys Gly
        435                 440                 445

Lys Ile Leu Asn Val Glu Lys Ala Arg Phe Asp Lys Met Leu Ser Ser
450                 455                 460

Gln Glu Val Ala Thr Leu Ile Thr Ala Leu Gly Cys Gly Ile Gly Arg
465                 470                 475                 480
```

```
Asp Glu Tyr Asn Pro Asp Lys Leu Arg Tyr His Ser Ile Ile Ile Met
                485                 490                 495

Thr Asp Ala Asp Val Asp Gly Ser His Ile Arg Thr Leu Leu Leu Thr
            500                 505                 510

Phe Phe Tyr Arg Gln Met Pro Glu Ile Val Glu Arg Gly His Val Tyr
        515                 520                 525

Ile Ala Gln Pro Pro Leu Tyr Lys Val Lys Gly Lys Gln Glu Gln
    530                 535                 540

Tyr Ile Lys Asp Asp Glu Ala Met Asp Gln Tyr Gln Ile Ser Ile Ala
545                 550                 555                 560

Leu Asp Gly Ala Thr Leu His Thr Asn Ala Ser Ala Pro Ala Leu Ala
                565                 570                 575

Gly Glu Ala Leu Glu Lys Leu Val Ser Glu Tyr Asn Ala Thr Gln Lys
            580                 585                 590

Met Ile Asn Arg Met Glu Arg Arg Tyr Pro Lys Ala Met Leu Lys Glu
        595                 600                 605

Leu Ile Tyr Gln Pro Thr Leu Thr Glu Ala Asp Leu Ser Asp Glu Gln
    610                 615                 620

Thr Val Thr Arg Trp Val Asn Ala Leu Val Ser Glu Leu Asn Asp Lys
625                 630                 635                 640

Glu Gln His Gly Ser Gln Trp Lys Phe Asp Val His Thr Asn Ala Glu
                645                 650                 655

Gln Asn Leu Phe Glu Pro Ile Val Arg Val Arg Thr His Gly Val Asp
            660                 665                 670

Thr Asp Tyr Pro Leu Asp His Glu Phe Ile Thr Gly Gly Glu Tyr Arg
        675                 680                 685

Arg Ile Cys Thr Leu Gly Glu Lys Leu Arg Gly Leu Leu Glu Glu Asp
    690                 695                 700

Ala Phe Ile Glu Arg Gly Glu Arg Arg Gln Pro Val Ala Ser Phe Glu
705                 710                 715                 720

Gln Ala Leu Asp Trp Leu Val Lys Glu Ser Arg Arg Gly Leu Ser Ile
                725                 730                 735

Gln Arg Tyr Lys Gly Leu Gly Glu Met Asn Pro Glu Gln Leu Trp Glu
            740                 745                 750

Thr Thr Met Asp Pro Glu Ser Arg Arg Met Leu Arg Val Thr Val Lys
        755                 760                 765

Asp Ala Ile Ala Ala Asp Gln Leu Phe Thr Thr Leu Met Gly Asp Ala
    770                 775                 780

Val Glu Pro Arg Arg Ala Phe Ile Glu Glu Asn Ala Leu Lys Ala Ala
785                 790                 795                 800

Asn Ile Asp Ile

<210> SEQ ID NO 8
<211> LENGTH: 92
<212> TYPE: PRT
<213> ORGANISM: Arabidopsis thaliana

<400> SEQUENCE: 8

Met Lys Arg Asp His His His His His Gln Asp Lys Lys Thr Met
1               5                   10                  15

Met Met Asn Glu Glu Asp Asp Gly Asn Gly Met Asp Glu Leu Leu Ala
                20                  25                  30

Val Leu Gly Tyr Lys Val Arg Ser Ser Glu Met Ala Asp Val Ala Gln
            35                  40                  45
```

Lys Leu Glu Gln Leu Glu Val Met Met Ser Asn Val Gln Glu Asp Asp
        50                  55                  60

Leu Ser Gln Leu Ala Thr Glu Thr Val His Tyr Asn Pro Ala Glu Leu
65                  70                  75                  80

Tyr Thr Trp Leu Asp Ser Met Leu Thr Asp Leu Asn
                85                  90

<210> SEQ ID NO 9
<211> LENGTH: 345
<212> TYPE: PRT
<213> ORGANISM: Arabidopsis thaliana

<400> SEQUENCE: 9

Met Ala Ala Ser Asp Glu Val Asn Leu Ile Glu Ser Arg Thr Val Val
1               5                   10                  15

Pro Leu Asn Thr Trp Val Leu Ile Ser Asn Phe Lys Val Ala Tyr Asn
                20                  25                  30

Ile Leu Arg Arg Pro Asp Gly Thr Phe Asn Arg His Leu Ala Glu Tyr
            35                  40                  45

Leu Asp Arg Lys Val Thr Ala Asn Ala Asn Pro Val Asp Gly Val Phe
50                  55                  60

Ser Phe Asp Val Leu Ile Asp Arg Arg Ile Asn Leu Leu Ser Arg Val
65                  70                  75                  80

Tyr Arg Pro Ala Tyr Ala Asp Gln Glu Gln Pro Pro Ser Ile Leu Asp
                85                  90                  95

Leu Glu Lys Pro Val Asp Gly Asp Ile Val Pro Val Ile Leu Phe Phe
            100                 105                 110

His Gly Gly Ser Phe Ala His Ser Ser Ala Asn Ser Ala Ile Tyr Asp
        115                 120                 125

Thr Leu Cys Arg Arg Leu Val Gly Leu Cys Lys Cys Val Val Val Ser
    130                 135                 140

Val Asn Tyr Arg Arg Ala Pro Glu Asn Pro Tyr Pro Cys Ala Tyr Asp
145                 150                 155                 160

Asp Gly Trp Ile Ala Leu Asn Trp Val Asn Ser Arg Ser Trp Leu Lys
                165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
        195                 200                 205

Ile Asp Val Leu Gly Asn Ile Leu Leu Asn Pro Met Phe Gly Gly Asn
    210                 215                 220

Glu Arg Thr Glu Ser Glu Lys Ser Leu Asp Gly Lys Tyr Phe Val Thr
225                 230                 235                 240

Val Arg Asp Arg Asp Trp Tyr Trp Lys Ala Phe Leu Pro Glu Gly Glu
                245                 250                 255

Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Val Ala Gly Leu
        275                 280                 285

Asp Leu Ile Arg Asp Trp Gln Leu Ala Tyr Ala Glu Gly Leu Lys Lys
    290                 295                 300

Ala Gly Gln Glu Val Lys Leu Met His Leu Glu Lys Ala Thr Val Gly
305                 310                 315                 320

Phe Tyr Leu Leu Pro Asn Asn Asn His Phe His Asn Val Met Asp Glu

Ile Ser Ala Phe Val Asn Ala Glu Cys
         340                 345

<210> SEQ ID NO 10
<211> LENGTH: 358
<212> TYPE: PRT
<213> ORGANISM: Arabidopsis thaliana

<400> SEQUENCE: 10

Met Ala Gly Gly Asn Glu Val Asn Leu Asn Glu Cys Lys Arg Ile Val
1               5                   10                  15

Pro Leu Asn Thr Trp Val Leu Ile Ser Asn Phe Lys Leu Ala Tyr Lys
            20                  25                  30

Val Leu Arg Arg Pro Asp Gly Ser Phe Asn Arg Asp Leu Ala Glu Phe
        35                  40                  45

Leu Asp Arg Lys Val Pro Ala Asn Ser Phe Pro Leu Asp Gly Val Phe
    50                  55                  60

Ser Phe Asp His Val Asp Ser Thr Thr Asn Leu Leu Thr Arg Ile Tyr
65                  70                  75                  80

Gln Pro Ala Ser Leu Leu His Gln Thr Arg His Gly Thr Leu Glu Leu
                85                  90                  95

Thr Lys Pro Leu Ser Thr Thr Glu Ile Val Pro Val Leu Ile Phe Phe
            100                 105                 110

His Gly Gly Ser Phe Thr His Ser Ser Ala Asn Ser Ala Ile Tyr Asp
        115                 120                 125

Thr Phe Cys Arg Arg Leu Val Thr Ile Cys Gly Val Val Val Val Ser
    130                 135                 140

Val Asp Tyr Arg Arg Ser Pro Glu His Arg Tyr Pro Cys Ala Tyr Asp
145                 150                 155                 160

Asp Gly Trp Asn Ala Leu Asn Trp Val Lys Ser Arg Val Trp Leu Gln
                165                 170                 175

Ser Gly Lys Asp Ser Asn Val Tyr Val Tyr Leu Ala Gly Asp Ser Ser
            180                 185                 190

Gly Gly Asn Ile Ala His Asn Val Ala Val Arg Ala Thr Asn Glu Gly
        195                 200                 205

Val Lys Val Leu Gly Asn Ile Leu His Pro Met Phe Gly Gly Gln
145                 215                 220

Glu Arg Thr Gln Ser Glu Lys Thr Leu Asp Gly Lys Tyr Phe Val Thr
225                 230                 235                 240

Ile Gln Asp Arg Asp Trp Tyr Trp Arg Ala Tyr Leu Pro Glu Gly Glu
                245                 250                 255

Asp Arg Asp His Pro Ala Cys Asn Pro Phe Gly Pro Arg Gly Gln Ser
            260                 265                 270

Leu Lys Gly Val Asn Phe Pro Lys Ser Leu Val Val Val Ala Gly Leu
        275                 280                 285

Asp Leu Val Gln Asp Trp Gln Leu Ala Tyr Val Asp Gly Leu Lys Lys
    290                 295                 300

Thr Gly Leu Glu Val Asn Leu Leu Tyr Leu Lys Gln Ala Thr Ile Gly
305                 310                 315                 320

Phe Tyr Phe Leu Pro Asn Asn Asp His Phe His Cys Leu Met Glu Glu
                325                 330                 335

Leu Asn Lys Phe Val His Ser Ile Glu Asp Ser Gln Leu Lys Ser Ser
            340                 345                 350

```
Pro Val Leu Leu Thr Pro
        355
```

<210> SEQ ID NO 11
<211> LENGTH: 344
<212> TYPE: PRT
<213> ORGANISM: Arabidopsis thaliana

<400> SEQUENCE: 11

```
Met Ala Gly Ser Glu Glu Val Asn Leu Ile Glu Ser Lys Thr Val Val
1               5                   10                  15

Pro Leu Asn Thr Trp Val Leu Ile Ser Asn Phe Lys Leu Ala Tyr Asn
            20                  25                  30

Leu Leu Arg Arg Pro Asp Gly Thr Phe Asn Arg His Leu Ala Glu Phe
        35                  40                  45

Leu Asp Arg Lys Val Pro Ala Asn Ala Asn Pro Val Asn Gly Val Phe
    50                  55                  60

Ser Phe Asp Val Ile Ile Asp Arg Gln Thr Asn Leu Leu Ser Arg Val
65                  70                  75                  80

Tyr Arg Pro Ala Asp Ala Gly Thr Ser Pro Ser Ile Thr Asp Leu Gln
                85                  90                  95

Asn Pro Val Asp Gly Glu Ile Val Pro Val Ile Val Phe Phe His Gly
            100                 105                 110

Gly Ser Phe Ala His Ser Ser Ala Asn Ser Ala Ile Tyr Asp Thr Leu
        115                 120                 125

Cys Arg Arg Leu Val Gly Leu Cys Gly Ala Val Val Val Ser Val Asn
    130                 135                 140

Tyr Arg Arg Ala Pro Glu Asn Arg Tyr Pro Cys Ala Tyr Asp Asp Gly
145                 150                 155                 160

Trp Ala Val Leu Lys Trp Val Asn Ser Ser Trp Leu Arg Ser Lys
                165                 170                 175

Lys Asp Ser Lys Val Arg Ile Phe Leu Ala Gly Asp Ser Ser Gly Gly
            180                 185                 190

Asn Ile Val His Asn Val Ala Val Arg Ala Val Glu Ser Arg Ile Asp
        195                 200                 205

Val Leu Gly Asn Ile Leu Leu Asn Pro Met Phe Gly Gly Thr Glu Arg
    210                 215                 220

Thr Glu Ser Glu Lys Arg Leu Asp Gly Lys Tyr Phe Val Thr Val Arg
225                 230                 235                 240

Asp Arg Asp Trp Tyr Trp Arg Ala Phe Leu Pro Glu Gly Glu Asp Arg
                245                 250                 255

Glu His Pro Ala Cys Ser Pro Phe Gly Pro Arg Ser Lys Ser Leu Glu
            260                 265                 270

Gly Leu Ser Phe Pro Lys Ser Leu Val Val Val Ala Gly Leu Asp Leu
        275                 280                 285

Ile Gln Asp Trp Gln Leu Lys Tyr Ala Glu Gly Leu Lys Lys Ala Gly
    290                 295                 300

Gln Glu Val Lys Leu Leu Tyr Leu Glu Gln Ala Thr Ile Gly Phe Tyr
305                 310                 315                 320

Leu Leu Pro Asn Asn Asn His Phe His Thr Val Met Asp Glu Ile Ala
                325                 330                 335

Ala Phe Val Asn Ala Glu Cys Gln
            340
```

<210> SEQ ID NO 12

<211> LENGTH: 182
<212> TYPE: PRT
<213> ORGANISM: Artificial Sequence
<220> FEATURE:
<223> OTHER INFORMATION: Snap-tag

<400> SEQUENCE: 12

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Ser His Leu Ala Ala Leu Ala Gly Asn Pro Ala Ala Thr Ala
        115                 120                 125

Ala Val Lys Thr Ala Leu Ser Gly Asn Pro Val Pro Ile Leu Ile Pro
    130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180
```

<210> SEQ ID NO 13
<211> LENGTH: 297
<212> TYPE: PRT
<213> ORGANISM: Artificial Sequence
<220> FEATURE:
<223> OTHER INFORMATION: Halo-tag

<400> SEQUENCE: 13

```
Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
```

```
            130                 135                 140
Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
                260                 265                 270

Leu Leu Gln Glu Asp Asn Pro Asp Leu Ile Gly Ser Glu Ile Ala Arg
            275                 280                 285

Trp Leu Ser Thr Leu Glu Ile Ser Gly
    290                 295

<210> SEQ ID NO 14
<211> LENGTH: 182
<212> TYPE: PRT
<213> ORGANISM: Artificial Sequence
<220> FEATURE:
<223> OTHER INFORMATION: CLIP-tag

<400> SEQUENCE: 14

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Ile Gln Ala Thr Ala
    50                  55                  60

Trp Leu Asn Ala Tyr Phe His Gln Pro Glu Ala Ile Glu Glu Phe Pro
65              70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Glu Ser His Leu Ala Ala Leu Val Gly Asn Pro Ala Ala Thr Ala
        115                 120                 125

Ala Val Asn Thr Ala Leu Asp Gly Asn Pro Val Pro Ile Leu Ile Pro
    130                 135                 140

Cys His Arg Val Val Gln Gly Asp Ser Asp Val Gly Pro Tyr Leu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180
```

<210> SEQ ID NO 15
<211> LENGTH: 159
<212> TYPE: PRT
<213> ORGANISM: Escherichia coli

<400> SEQUENCE: 15

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 16
<211> LENGTH: 278
<212> TYPE: PRT
<213> ORGANISM: Homo sapiens

<400> SEQUENCE: 16

Ile Gln Gln Ala Thr Thr Gly Val Ser Gln Glu Thr Ser Glu Asn Pro
1               5                   10                  15

Gly Asn Lys Thr Ile Val Pro Ala Thr Leu Pro Gln Leu Thr Pro Thr
            20                  25                  30

Leu Val Ser Leu Leu Glu Val Ile Glu Pro Glu Val Leu Tyr Ala Gly
        35                  40                  45

Tyr Asp Ser Ser Val Pro Asp Ser Thr Trp Arg Ile Met Thr Thr Leu
    50                  55                  60

Asn Met Leu Gly Gly Arg Gln Val Ile Ala Ala Val Lys Trp Ala Lys
65                  70                  75                  80

Ala Ile Pro Gly Phe Arg Asn Leu His Leu Asp Asp Gln Met Thr Leu
                85                  90                  95

Leu Gln Tyr Ser Trp Met Phe Leu Met Ala Phe Ala Leu Gly Trp Arg
            100                 105                 110

Ser Tyr Arg Gln Ser Ser Ala Asn Leu Leu Cys Phe Ala Pro Asp Leu
        115                 120                 125

Ile Ile Asn Glu Gln Arg Met Thr Leu Pro Cys Met Tyr Asp Gln Cys
    130                 135                 140

Lys His Met Leu Tyr Val Ser Ser Glu Leu His Arg Leu Gln Val Ser
145                 150                 155                 160

Tyr Glu Glu Tyr Leu Cys Met Lys Thr Leu Leu Leu Leu Ser Ser Val
                165                 170                 175

Pro Lys Asp Gly Leu Lys Ser Gln Glu Leu Phe Asp Glu Ile Arg Met

```
                180             185             190
Thr Tyr Ile Lys Glu Leu Gly Lys Ala Ile Val Lys Arg Glu Gly Asn
            195             200             205
Ser Ser Gln Asn Trp Gln Arg Phe Tyr Gln Leu Thr Lys Leu Leu Asp
        210             215             220
Ser Met His Glu Val Val Glu Asn Leu Leu Asn Tyr Cys Phe Gln Thr
225             230             235             240
Phe Leu Asp Lys Thr Met Ser Ile Glu Phe Pro Glu Met Leu Ala Glu
            245             250             255
Ile Ile Thr Asn Gln Ile Pro Lys Tyr Ser Asn Gly Asn Ile Lys Lys
        260             265             270
Leu Leu Phe His Gln Lys
        275

<210> SEQ ID NO 17
<211> LENGTH: 176
<212> TYPE: PRT
<213> ORGANISM: Arabidopsis thaliana

<400> SEQUENCE: 17

Gln Asp Glu Phe Thr Gln Leu Ser Gln Ser Ile Ala Glu Phe His Thr
1               5                  10                  15
Tyr Gln Leu Gly Asn Gly Arg Cys Ser Ser Leu Leu Ala Gln Arg Ile
            20                  25                  30
His Ala Pro Glu Thr Val Trp Ser Val Arg Arg Phe Asp Arg
        35                  40                  45
Pro Gln Ile Tyr Lys His Phe Ile Lys Ser Cys Asn Val Ser Glu Asp
    50                  55                  60
Phe Glu Met Arg Val Gly Cys Thr Arg Asp Val Asn Val Ile Ser Gly
65                  70                  75                  80
Leu Pro Ala Asn Thr Ser Arg Glu Arg Leu Asp Leu Leu Asp Asp Asp
                85                  90                  95
Arg Arg Val Thr Gly Phe Ser Ile Thr Gly Gly Glu His Arg Leu Arg
            100                 105                 110
Asn Tyr Lys Ser Val Thr Thr Val His Arg Phe Glu Lys Glu Glu
            115                 120                 125
Glu Glu Arg Ile Trp Thr Val Val Leu Glu Ser Tyr Val Val Asp Val
        130                 135                 140
Pro Glu Gly Asn Ser Glu Glu Asp Thr Arg Leu Phe Ala Asp Thr Val
145                 150                 155                 160
Ile Arg Leu Asn Leu Gln Lys Leu Ala Ser Ile Thr Glu Ala Met Asn
                165                 170                 175

<210> SEQ ID NO 18
<211> LENGTH: 298
<212> TYPE: PRT
<213> ORGANISM: Arabidopsis thaliana

<400> SEQUENCE: 18

Val Pro Leu Tyr Gly Phe Thr Ser Ile Cys Gly Arg Arg Pro Glu Met
1               5                  10                  15
Glu Asp Ala Val Ser Thr Ile Pro Arg Phe Leu Gln Ser Ser Ser Gly
            20                  25                  30
Ser Met Leu Asp Gly Arg Phe Asp Pro Gln Ser Ala Ala His Phe Phe
        35                  40                  45
Gly Val Tyr Asp Gly His Gly Gly Ser Gln Val Ala Asn Tyr Cys Arg
```

```
            50                  55                  60
Glu Arg Met His Leu Ala Leu Ala Glu Glu Ile Ala Lys Glu Lys Pro
 65                  70                  75                  80

Met Leu Cys Asp Gly Asp Thr Trp Leu Glu Lys Trp Lys Lys Ala Leu
                 85                  90                  95

Phe Asn Ser Phe Leu Arg Val Asp Ser Glu Ile Glu Ser Val Ala Pro
            100                 105                 110

Glu Thr Val Gly Ser Thr Ser Val Val Ala Val Phe Pro Ser His
        115                 120                 125

Ile Phe Val Ala Asn Cys Gly Asp Ser Arg Ala Val Leu Cys Arg Gly
    130                 135                 140

Lys Thr Ala Leu Pro Leu Ser Val Asp His Lys Pro Asp Arg Glu Asp
145                 150                 155                 160

Glu Ala Ala Arg Ile Glu Ala Ala Gly Gly Lys Val Ile Gln Trp Asn
                165                 170                 175

Gly Ala Arg Val Phe Gly Val Leu Ala Met Ser Arg Ser Ile Gly Asp
            180                 185                 190

Arg Tyr Leu Lys Pro Ser Ile Ile Pro Asp Pro Glu Val Thr Ala Val
        195                 200                 205

Lys Arg Val Lys Glu Asp Asp Cys Leu Ile Leu Ala Ser Asp Gly Val
210                 215                 220

Trp Asp Val Met Thr Asp Glu Glu Ala Cys Glu Met Ala Arg Lys Arg
225                 230                 235                 240

Ile Leu Leu Trp His Lys Lys Asn Ala Val Ala Gly Asp Ala Ser Leu
                245                 250                 255

Leu Ala Asp Glu Arg Arg Lys Glu Gly Lys Asp Pro Ala Ala Met Ser
            260                 265                 270

Ala Ala Glu Tyr Leu Ser Lys Leu Ala Ile Gln Arg Gly Ser Lys Asp
        275                 280                 285

Asn Ile Ser Val Val Val Val Asp Leu Lys
    290                 295

<210> SEQ ID NO 19
<211> LENGTH: 20
<212> TYPE: PRT
<213> ORGANISM: Artificial Sequence
<220> FEATURE:
<223> OTHER INFORMATION: 4-EAAAR-linker

<400> SEQUENCE: 19

Glu Ala Ala Ala Arg Glu Ala Ala Arg Glu Ala Ala Ala Arg Glu
  1               5                  10                  15

Ala Ala Ala Arg
            20

<210> SEQ ID NO 20
<211> LENGTH: 22
<212> TYPE: PRT
<213> ORGANISM: Artificial Sequence
<220> FEATURE:
<223> OTHER INFORMATION: GS-4x-EAAAR-linker

<400> SEQUENCE: 20

Gly Ser Glu Ala Ala Ala Arg Glu Ala Ala Arg Glu Ala Ala Ala
  1               5                  10                  15

Arg Glu Ala Ala Ala Arg
            20
```

<210> SEQ ID NO 21
<211> LENGTH: 45
<212> TYPE: PRT
<213> ORGANISM: Homo sapiens

<400> SEQUENCE: 21

```
Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp
        35                  40                  45
```

<210> SEQ ID NO 22
<211> LENGTH: 231
<212> TYPE: PRT
<213> ORGANISM: Homo sapiens

<400> SEQUENCE: 22

```
Glu Pro Lys Ser Pro Asp Lys Thr His Thr Cys Pro Pro Cys Pro Ala
1               5                   10                  15
Pro Pro Val Ala Gly Pro Ser Val Phe Leu Phe Pro Pro Lys Pro Lys
            20                  25                  30
Asp Thr Leu Met Ile Ala Arg Thr Pro Glu Val Thr Cys Val Val Val
        35                  40                  45
Asp Val Ser His Glu Asp Pro Glu Val Lys Phe Asn Trp Tyr Val Asp
    50                  55                  60
Gly Val Glu Val His Asn Ala Lys Thr Lys Pro Arg Glu Glu Gln Tyr
65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Asp Glu Leu Thr Lys
    130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys
225                 230
```

<210> SEQ ID NO 23
<211> LENGTH: 16
<212> TYPE: PRT
<213> ORGANISM: Homo sapiens

<400> SEQUENCE: 23

```
Gly Leu Ala Val Ser Thr Ile Ser Ser Phe Phe Pro Pro Gly Tyr Gln
```

-continued

<210> SEQ ID NO 24
<211> LENGTH: 15
<212> TYPE: PRT
<213> ORGANISM: Artificial Sequence
<220> FEATURE:
<223> OTHER INFORMATION: peptide linker

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 121
<212> TYPE: PRT
<213> ORGANISM: mus musculus
<220> FEATURE:
<223> OTHER INFORMATION: fragment of anti-human CD19 monoclonal antibody
    4G7 immunoglobulin gamma1 heavy chain-(residues 20-140)

<400> SEQUENCE: 25

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser
        115                 120

<210> SEQ ID NO 26
<211> LENGTH: 115
<212> TYPE: PRT
<213> ORGANISM: mus musculus
<220> FEATURE:
<223> OTHER INFORMATION: fragment of anti-human CD19 monoclonal antibody
    4G7 immunoglobulin kappa light chain (residues 21-130)

<400> SEQUENCE: 26

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

```
Leu Glu Tyr Pro Phe Thr Phe Gly Ala Gly Thr Lys Leu Glu Leu Lys
                100                 105                 110

Arg Ala Asp
        115

<210> SEQ ID NO 27
<211> LENGTH: 116
<212> TYPE: PRT
<213> ORGANISM: artificial sequence
<220> FEATURE:
<223> OTHER INFORMATION: fragment of anti-human CD19 monoclonal antibody
      4G7 immunoglobulin kappa light chain

<400> SEQUENCE: 27

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
                100                 105                 110

Arg Ser Asp Pro
        115

<210> SEQ ID NO 28
<211> LENGTH: 112
<212> TYPE: PRT
<213> ORGANISM: Homo sapiens

<400> SEQUENCE: 28

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 29
<211> LENGTH: 215
<212> TYPE: PRT
<213> ORGANISM: Homo sapiens

<400> SEQUENCE: 29

Met Asp Thr Glu Ser Asn Arg Arg Ala Asn Leu Ala Leu Pro Gln Glu
```

```
            1               5                  10                 15
        Pro Ser Ser Val Pro Ala Phe Glu Val Leu Glu Ile Ser Pro Gln Glu
                        20                 25                 30

Val Ser Ser Gly Arg Leu Leu Lys Ser Ala Ser Pro Pro Leu His
                        35                 40                 45

Thr Trp Leu Thr Val Leu Lys Lys Glu Gln Glu Phe Leu Gly Val Thr
                        50                 55                 60

Gln Ile Leu Thr Ala Met Ile Cys Leu Cys Phe Gly Thr Val Val Cys
         65                 70                 75                  80

Ser Val Leu Asp Ile Ser His Ile Glu Gly Asp Ile Phe Ser Ser Phe
                        85                 90                 95

Lys Ala Gly Tyr Pro Phe Trp Gly Ala Ile Phe Phe Ser Ile Ser Gly
                       100                105                110

Met Leu Ser Ile Ile Ser Glu Arg Arg Asn Ala Thr Tyr Leu Val Arg
                       115                120                125

Gly Ser Leu Gly Ala Asn Thr Ala Ser Ser Ile Ala Gly Gly Thr Gly
                       130                135                140

Ile Thr Ile Leu Ile Ile Asn Leu Lys Lys Ser Leu Ala Tyr Ile His
        145                150                155                160

Ile His Ser Cys Gln Lys Phe Phe Glu Thr Lys Cys Phe Met Ala Ser
                       165                170                175

Phe Ser Thr Glu Ile Val Val Met Met Leu Phe Leu Thr Ile Leu Gly
                       180                185                190

Leu Gly Ser Ala Val Ser Leu Thr Ile Cys Gly Ala Gly Glu Glu Leu
                       195                200                205

Lys Gly Asn Lys Val Pro Glu
                       210                215

<210> SEQ ID NO 30
<211> LENGTH: 43
<212> TYPE: PRT
<213> ORGANISM: Homo sapiens

<400> SEQUENCE: 30

Leu Gly Glu Pro Gln Leu Cys Tyr Ile Leu Asp Ala Ile Leu Phe Leu
 1               5                  10                 15

Tyr Gly Ile Val Leu Thr Leu Leu Tyr Cys Arg Leu Lys Ile Gln Val
                20                 25                 30

Arg Lys Ala Ala Ile Thr Ser Tyr Glu Lys Ser
                35                 40

<210> SEQ ID NO 31
<211> LENGTH: 42
<212> TYPE: PRT
<213> ORGANISM: Homo sapiens

<400> SEQUENCE: 31

Lys Arg Gly Arg Lys Lys Leu Leu Tyr Ile Phe Lys Gln Pro Phe Met
 1               5                  10                 15

Arg Pro Val Gln Thr Thr Gln Glu Glu Asp Gly Cys Ser Cys Arg Phe
                20                 25                 30

Pro Glu Glu Glu Glu Gly Gly Cys Glu Leu
                35                 40

<210> SEQ ID NO 32
<211> LENGTH: 24
<212> TYPE: PRT
```

<213> ORGANISM: Homo sapiens

<400> SEQUENCE: 32

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 33
<211> LENGTH: 27
<212> TYPE: PRT
<213> ORGANISM: Homo sapiens

<400> SEQUENCE: 33

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 34
<211> LENGTH: 52
<212> TYPE: PRT
<213> ORGANISM: Homo sapiens

<400> SEQUENCE: 34

Phe Phe Ile Pro Leu Leu Val Val Ile Leu Phe Ala Val Asp Thr Gly
1               5                   10                  15

Leu Phe Ile Ser Thr Gln Gln Gln Val Thr Phe Leu Leu Lys Ile Lys
            20                  25                  30

Arg Thr Arg Lys Gly Phe Arg Leu Leu Asn Pro His Pro Lys Pro Asn
        35                  40                  45

Pro Lys Asn Asn
    50

<210> SEQ ID NO 35
<211> LENGTH: 43
<212> TYPE: PRT
<213> ORGANISM: Homo sapiens

<400> SEQUENCE: 35

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Ala Ile Thr Ser Tyr Glu Lys Ser
        35                  40

<210> SEQ ID NO 36
<211> LENGTH: 215
<212> TYPE: PRT
<213> ORGANISM: Homo sapiens

<400> SEQUENCE: 36

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr

```
            50                  55                  60
Gln Ile Leu Thr Ala Met Ile Cys Leu Cys Phe Gly Thr Val Val Cys
 65                  70                  75                  80

Ser Val Leu Asp Ile Ser His Ile Glu Gly Asp Ile Phe Ser Ser Phe
                 85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu
    210                 215

<210> SEQ ID NO 37
<211> LENGTH: 2549
<212> TYPE: PRT
<213> ORGANISM: Homo sapiens

<400> SEQUENCE: 37

Met Leu Gly Thr Gly Pro Ala Ala Ala Thr Thr Ala Thr Thr Ser
  1               5                  10                  15

Ser Asn Val Ser Val Leu Gln Gln Phe Ala Ser Gly Leu Lys Ser Arg
                 20                  25                  30

Asn Glu Glu Thr Arg Ala Lys Ala Ala Lys Glu Leu Gln His Tyr Val
             35                  40                  45

Thr Met Glu Leu Arg Glu Met Ser Gln Glu Glu Ser Thr Arg Phe Tyr
         50                  55                  60

Asp Gln Leu Asn His His Ile Phe Glu Leu Val Ser Ser Ser Asp Ala
 65                  70                  75                  80

Asn Glu Arg Lys Gly Gly Ile Leu Ala Ile Ala Ser Leu Ile Gly Val
                 85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205
```

```
Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
                340                 345                 350

Lys Ser Thr Leu Val Glu Ser Arg Cys Cys Arg Asp Leu Met Glu Glu
                355                 360                 365

Lys Phe Asp Gln Val Cys Gln Trp Val Leu Lys Cys Arg Asn Ser Lys
370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
                420                 425                 430

Ala Phe Gln Ala Leu Gly Leu Leu Ser Val Ala Val Arg Ser Glu Phe
                435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
                500                 505                 510

Leu Ser Pro Ala Leu Thr Ala Val Leu Tyr Asp Leu Ser Arg Gln Ile
                515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
                580                 585                 590

Glu Phe Glu Gly His Ser Leu Thr Gln Phe Val Arg His Cys Ala Asp
                595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
```

-continued

```
            625                 630                 635                 640
        Ala His Val Val Ser Gln Thr Ala Val Gln Val Val Ala Asp Val Leu
                            645                 650                 655

Ser Lys Leu Leu Val Val Gly Ile Thr Asp Pro Asp Pro Asp Ile Arg
                            660                 665                 670

Tyr Cys Val Leu Ala Ser Leu Asp Glu Arg Phe Asp Ala His Leu Ala
                            675                 680                 685

Gln Ala Glu Asn Leu Gln Ala Leu Phe Val Ala Leu Asn Asp Gln Val
                            690                 695                 700

Phe Glu Ile Arg Glu Leu Ala Ile Cys Thr Val Gly Arg Leu Ser Ser
        705                 710                 715                 720

Met Asn Pro Ala Phe Val Met Pro Phe Leu Arg Lys Met Leu Ile Gln
                            725                 730                 735

Ile Leu Thr Glu Leu Glu His Ser Gly Ile Gly Arg Ile Lys Glu Gln
                            740                 745                 750

Ser Ala Arg Met Leu Gly His Leu Val Ser Asn Ala Pro Arg Leu Ile
                            755                 760                 765

Arg Pro Tyr Met Glu Pro Ile Leu Lys Ala Leu Ile Leu Lys Leu Lys
                            770                 775                 780

Asp Pro Asp Pro Asp Pro Asn Pro Gly Val Ile Asn Asn Val Leu Ala
        785                 790                 795                 800

Thr Ile Gly Glu Leu Ala Gln Val Ser Gly Leu Glu Met Arg Lys Trp
                            805                 810                 815

Val Asp Glu Leu Phe Ile Ile Met Asp Met Leu Gln Asp Ser Ser
                            820                 825                 830

Leu Leu Ala Lys Arg Gln Val Ala Leu Trp Thr Leu Gly Gln Leu Val
                            835                 840                 845

Ala Ser Thr Gly Tyr Val Val Glu Pro Tyr Arg Lys Tyr Pro Thr Leu
                            850                 855                 860

Leu Glu Val Leu Leu Asn Phe Leu Lys Thr Glu Gln Asn Gln Gly Thr
        865                 870                 875                 880

Arg Arg Glu Ala Ile Arg Val Leu Gly Leu Leu Gly Ala Leu Asp Pro
                            885                 890                 895

Tyr Lys His Lys Val Asn Ile Gly Met Ile Asp Gln Ser Arg Asp Ala
                            900                 905                 910

Ser Ala Val Ser Leu Ser Glu Ser Lys Ser Ser Gln Asp Ser Ser Asp
                            915                 920                 925

Tyr Ser Thr Ser Glu Met Leu Val Asn Met Gly Asn Leu Pro Leu Asp
                            930                 935                 940

Glu Phe Tyr Pro Ala Val Ser Met Val Ala Leu Met Arg Ile Phe Arg
        945                 950                 955                 960

Asp Gln Ser Leu Ser His His Thr Met Val Val Gln Ala Ile Thr
                            965                 970                 975

Phe Ile Phe Lys Ser Leu Gly Leu Lys Cys Val Gln Phe Leu Pro Gln
                            980                 985                 990

Val Met Pro Thr Phe Leu Asn Val  Ile Arg Val Cys Asp  Gly Ala Ile
                  995                 1000                1005

Arg Glu  Phe Leu Phe Gln Gln  Leu Gly Met Leu Val  Ser Phe Val
                 1010                1015                1020

Lys Ser  His Ile Arg Pro Tyr  Met Asp Glu Ile Val  Thr Leu Met
                 1025                1030                1035

Arg Glu  Phe Trp Val Met Asn  Thr Ser Ile Gln Ser  Thr Ile Ile
                 1040                1045                1050
```

Leu Leu Ile Glu Gln Ile Val Val Ala Leu Gly Gly Glu Phe Lys
1055               1060               1065

Leu Tyr Leu Pro Gln Leu Ile Pro His Met Leu Arg Val Phe Met
1070               1075               1080

His Asp Asn Ser Pro Gly Arg Ile Val Ser Ile Lys Leu Leu Ala
1085               1090               1095

Ala Ile Gln Leu Phe Gly Ala Asn Leu Asp Asp Tyr Leu His Leu
1100               1105               1110

Leu Leu Pro Pro Ile Val Lys Leu Phe Asp Ala Pro Glu Ala Pro
1115               1120               1125

Leu Pro Ser Arg Lys Ala Ala Leu Glu Thr Val Asp Arg Leu Thr
1130               1135               1140

Glu Ser Leu Asp Phe Thr Asp Tyr Ala Ser Arg Ile Ile His Pro
1145               1150               1155

Ile Val Arg Thr Leu Asp Gln Ser Pro Glu Leu Arg Ser Thr Ala
1160               1165               1170

Met Asp Thr Leu Ser Ser Leu Val Phe Gln Leu Gly Lys Lys Tyr
1175               1180               1185

Gln Ile Phe Ile Pro Met Val Asn Lys Val Leu Val Arg His Arg
1190               1195               1200

Ile Asn His Gln Arg Tyr Asp Val Leu Ile Cys Arg Ile Val Lys
1205               1210               1215

Gly Tyr Thr Leu Ala Asp Glu Glu Asp Pro Leu Ile Tyr Gln
1220               1225               1230

His Arg Met Leu Arg Ser Gly Gln Gly Asp Ala Leu Ala Ser Gly
1235               1240               1245

Pro Val Glu Thr Gly Pro Met Lys Lys Leu His Val Ser Thr Ile
1250               1255               1260

Asn Leu Gln Lys Ala Trp Gly Ala Ala Arg Arg Val Ser Lys Asp
1265               1270               1275

Asp Trp Leu Glu Trp Leu Arg Arg Leu Ser Leu Glu Leu Leu Lys
1280               1285               1290

Asp Ser Ser Pro Ser Leu Arg Ser Cys Trp Ala Leu Ala Gln
1295               1300               1305

Ala Tyr Asn Pro Met Ala Arg Asp Leu Phe Asn Ala Ala Phe Val
1310               1315               1320

Ser Cys Trp Ser Glu Leu Asn Glu Asp Gln Gln Asp Glu Leu Ile
1325               1330               1335

Arg Ser Ile Glu Leu Ala Leu Thr Ser Gln Asp Ile Ala Glu Val
1340               1345               1350

Thr Gln Thr Leu Leu Asn Leu Ala Glu Phe Met Glu His Ser Asp
1355               1360               1365

Lys Gly Pro Leu Pro Leu Arg Asp Asp Asn Gly Ile Val Leu Leu
1370               1375               1380

Gly Glu Arg Ala Ala Lys Cys Arg Ala Tyr Ala Lys Ala Leu His
1385               1390               1395

Tyr Lys Glu Leu Glu Phe Gln Lys Gly Pro Thr Pro Ala Ile Leu
1400               1405               1410

Glu Ser Leu Ile Ser Ile Asn Asn Lys Leu Gln Gln Pro Glu Ala
1415               1420               1425

Ala Ala Gly Val Leu Glu Tyr Ala Met Lys His Phe Gly Glu Leu
1430               1435               1440

```
Glu Ile Gln Ala Thr Trp Tyr Glu Lys Leu His Glu Trp Glu Asp
1445                1450                1455

Ala Leu Val Ala Tyr Asp Lys Lys Met Asp Thr Asn Lys Asp Asp
1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Thr Ala Thr Thr Thr Ala Ser Thr Glu Gly Ser Asn
```

```
             1835                1840                1845

Ser  Glu  Ser  Glu  Ala  Glu  Ser  Thr  Glu  Asn  Ser  Pro  Thr  Pro  Ser
     1850                1855                1860

Pro  Leu  Gln  Lys  Lys  Val  Thr  Glu  Asp  Leu  Ser  Lys  Thr  Leu  Leu
     1865                1870                1875

Met  Tyr  Thr  Val  Pro  Ala  Val  Gln  Gly  Phe  Phe  Arg  Ser  Ile  Ser
     1880                1885                1890

Leu  Ser  Arg  Gly  Asn  Asn  Leu  Gln  Asp  Thr  Leu  Arg  Val  Leu  Thr
     1895                1900                1905

Leu  Trp  Phe  Asp  Tyr  Gly  His  Trp  Pro  Asp  Val  Asn  Glu  Ala  Leu
     1910                1915                1920

Val  Glu  Gly  Val  Lys  Ala  Ile  Gln  Ile  Asp  Thr  Trp  Leu  Gln  Val
     1925                1930                1935

Ile  Pro  Gln  Leu  Ile  Ala  Arg  Ile  Asp  Thr  Pro  Arg  Pro  Leu  Val
     1940                1945                1950

Gly  Arg  Leu  Ile  His  Gln  Leu  Leu  Thr  Asp  Ile  Gly  Arg  Tyr  His
     1955                1960                1965

Pro  Gln  Ala  Leu  Ile  Tyr  Pro  Leu  Thr  Val  Ala  Ser  Lys  Ser  Thr
     1970                1975                1980

Thr  Thr  Ala  Arg  His  Asn  Ala  Ala  Asn  Lys  Ile  Leu  Lys  Asn  Met
     1985                1990                1995

Cys  Glu  His  Ser  Asn  Thr  Leu  Val  Gln  Gln  Ala  Met  Met  Val  Ser
     2000                2005                2010

Glu  Glu  Leu  Ile  Arg  Val  Ala  Ile  Leu  Trp  His  Glu  Met  Trp  His
     2015                2020                2025

Glu  Gly  Leu  Glu  Glu  Ala  Ser  Arg  Leu  Tyr  Phe  Gly  Glu  Arg  Asn
     2030                2035                2040

Val  Lys  Gly  Met  Phe  Glu  Val  Leu  Glu  Pro  Leu  His  Ala  Met  Met
     2045                2050                2055

Glu  Arg  Gly  Pro  Gln  Thr  Leu  Lys  Glu  Thr  Ser  Phe  Asn  Gln  Ala
     2060                2065                2070

Tyr  Gly  Arg  Asp  Leu  Met  Glu  Ala  Gln  Glu  Trp  Cys  Arg  Lys  Tyr
     2075                2080                2085

Met  Lys  Ser  Gly  Asn  Val  Lys  Asp  Leu  Thr  Gln  Ala  Trp  Asp  Leu
     2090                2095                2100

Tyr  Tyr  His  Val  Phe  Arg  Arg  Ile  Ser  Lys  Gln  Leu  Pro  Gln  Leu
     2105                2110                2115

Thr  Ser  Leu  Glu  Leu  Gln  Tyr  Val  Ser  Pro  Lys  Leu  Leu  Met  Cys
     2120                2125                2130

Arg  Asp  Leu  Glu  Leu  Ala  Val  Pro  Gly  Thr  Tyr  Asp  Pro  Asn  Gln
     2135                2140                2145

Pro  Ile  Ile  Arg  Ile  Gln  Ser  Ile  Ala  Pro  Ser  Leu  Gln  Val  Ile
     2150                2155                2160

Thr  Ser  Lys  Gln  Arg  Pro  Arg  Lys  Leu  Thr  Leu  Met  Gly  Ser  Asn
     2165                2170                2175

Gly  His  Glu  Phe  Val  Phe  Leu  Leu  Lys  Gly  His  Glu  Asp  Leu  Arg
     2180                2185                2190

Gln  Asp  Glu  Arg  Val  Met  Gln  Leu  Phe  Gly  Leu  Val  Asn  Thr  Leu
     2195                2200                2205

Leu  Ala  Asn  Asp  Pro  Thr  Ser  Leu  Arg  Lys  Asn  Leu  Ser  Ile  Gln
     2210                2215                2220

Arg  Tyr  Ala  Val  Ile  Pro  Leu  Ser  Thr  Asn  Ser  Gly  Leu  Ile  Gly
     2225                2230                2235
```

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
2255                2260                2265

Leu Arg Met Ala Pro Asp Tyr Asp His Leu Thr Leu Met Gln Lys
2270                2275                2280

Val Glu Val Phe Glu His Ala Val Asn Asn Thr Ala Gly Asp Asp
2285                2290                2295

Leu Ala Lys Leu Leu Trp Leu Lys Ser Pro Ser Ser Glu Val Trp
2300                2305                2310

Phe Asp Arg Arg Thr Asn Tyr Thr Arg Ser Leu Ala Val Met Ser
2315                2320                2325

Met Val Gly Tyr Ile Leu Gly Leu Gly Asp Arg His Pro Ser Asn
2330                2335                2340

Leu Met Leu Asp Arg Leu Ser Gly Lys Ile Leu His Ile Asp Phe
2345                2350                2355

Gly Asp Cys Phe Glu Val Ala Met Thr Arg Glu Lys Phe Pro Glu
2360                2365                2370

Lys Ile Pro Phe Arg Leu Thr Arg Met Leu Thr Asn Ala Met Glu
2375                2380                2385

Val Thr Gly Leu Asp Gly Asn Tyr Arg Ile Thr Cys His Thr Val
2390                2395                2400

Met Glu Val Leu Arg Glu His Lys Asp Ser Val Met Ala Val Leu
2405                2410                2415

Glu Ala Phe Val Tyr Asp Pro Leu Leu Asn Trp Arg Leu Met Asp
2420                2425                2430

Thr Asn Thr Lys Gly Asn Lys Arg Ser Arg Thr Arg Thr Asp Ser
2435                2440                2445

Tyr Ser Ala Gly Gln Ser Val Glu Ile Leu Asp Gly Val Glu Leu
2450                2455                2460

Gly Glu Pro Ala His Lys Lys Thr Gly Thr Thr Val Pro Glu Ser
2465                2470                2475

Ile His Ser Phe Ile Gly Asp Gly Leu Val Lys Pro Glu Ala Leu
2480                2485                2490

Asn Lys Lys Ala Ile Gln Ile Ile Asn Arg Val Arg Asp Lys Leu
2495                2500                2505

Thr Gly Arg Asp Phe Ser His Asp Asp Thr Leu Asp Val Pro Thr
2510                2515                2520

Gln Val Glu Leu Leu Ile Lys Gln Ala Thr Ser His Glu Asn Leu
2525                2530                2535

Cys Gln Cys Tyr Ile Gly Trp Cys Pro Phe Trp
2540                2545

<210> SEQ ID NO 38
<211> LENGTH: 2541
<212> TYPE: DNA
<213> ORGANISM: Artificial Sequence
<220> FEATURE:
<223> OTHER INFORMATION: Construct pCLS24707

<400> SEQUENCE: 38
atgatcccag ccgtggtcct gctgctgctg ctgctggtgg agcaggcagc tgcactggga      60 gaacccagc tgtgctacat cctggacgcc attctgttcc tgtacggcat tgtgctgaca     120
ctgctgtatt gtaggctgaa gatccaggtc cgcaaagccg ctattacttc atatgagaag    180

```
agccgcgtga agttcagccg atccgctgac gcaccagcat accagcaggg acagaaccag    240
ctgtataacg agctgaatct gggacggaga gaggaatacg acgtcctgga taagaggcgc    300
ggcagggatc ctgaaatggg cgggaagcct cgacggaaaa acccacagga ggggctgtac    360
aatgaactgc agaaggacaa aatggctgag gcatatagtg aaatcggaat gaagggcgag    420
agaaggcgcg ggaaaggaca cgatggcctg taccaggggc tgtccaccgc cacaaaagac    480
acttatgatg cactgcatat gcaggccctg cccctcgcg gcagcggggc caccaacttc    540
tccctgctga gcaggctgg agacgtggag gaaaatcccg gccctatggc tcccgcaatg    600 gagtcccta cactgctgtg cgtggcactg ctgttctttg caccagatgg cgtgctggca    660
gaggtccagc tgcagcagtc aggaccagaa ctgatcaaac ccggagcatc tgtgaaaatg    720
agttgtaagg cctcaggcta tactttcacc tcttacgtga tgcactgggt caagcagaaa    780
cctggacagg gcctggagtg gatcggctat attaatccat acaacgacgg gaccaagtac    840
aacgaaaagt ttaaaggcaa ggcaacactg actagtgata gagctcctc tactgcttac    900 atggagctga gttcactgac cagcgaagac tccgctgtgt actattgcgc aagaggaacc    960
tactattacg gctctagggt gttcgattac tgggggcagg gaaccacact gacagtcagc    1020
tccggaggag gaggatccgg aggaggaggg tctggaggcg ggggaagtga catcgtgatg    1080
acacaggccg ctcctagcat tccagtgact cccggcgagt cagtcagcat ctcctgtcgg    1140
tctagtaaga gcctgctgaa ctccaatgga aacacatatc tgtactggtt ctgcagagg    1200 cctggccagt ccccacagct gctgatctat cgcatgtcta acctggccag tggcgtgccc    1260
gatcggttct ctggcagtgg gtcaggaacc gcctttacac tgaggattag ccgcgtcgag    1320
gctgaagacg tggggtcta ttactgcatg cagcatctgg agtaccctt cacatttggc    1380 gccgggacta aactggaact gaagcgcgcc gatactacca caccagctcc acgaccacct    1440
actcctgcac caaccattgc ttcacagcct ctgagcctgc gaccagaagc ttgccggcca    1500
gcagcaggag gagcagtgca caccagaggc ctggacttcg cctgtgattt ctttatcccc    1560
ctgctggtgg tcattctgtt cgccgtggac actgggctgt ttatctccac ccagcagcag    1620
gtcacattcc tgctgaaaat taagcggacc agaaagggc tccggctgct gaatccccat    1680
cctaaaccaa accccaagaa caatggaagc ggagagggac gaggatccct gctgacctgc    1740
ggggacgtgg aggaaaaccc aggacctatg gacactgagt ctaaccggag agccaatctg    1800
gctctgccac aggaacccag ctccgtgccc gcattcgagg tcctggaaat ctctcctcag    1860
gaggtgtcta gtgggcgcct gctgaagagt gcctcaagcc ccctctgca cacttggctg    1920 accgtgctga agaaagagca ggaattcctg ggagtcaccc agatcctgac agctatgatt    1980
tgcctgtgtt ttggcacagt ggtctgcagt gtgctgaca tctcacatat tgaggggat    2040 atcttctcct cttttaaggc tgggtaccct ttttggggag caatcttctt tagcatttcc    2100
ggaatgctgt caatcattag cgaaaggcgc aacgcaacat atctggtgcg aggaagcctg    2160
ggcgcaaata ctgccagttc aatcgccggc gggacaggca tcactattct gatcattaac    2220
ctgaagaaaa gcctggctta catccacatt cattcctgcc agaagttctt tgagactaaa    2280
tgtttcatgg cctctttttag taccgaaatc gtggtcatga tgctgttcct gaccattctg    2340
gggctgggat ccgccgtgtc tctgacaatc tgcggcgctg ggaggaact gaagggcaac    2400 aaggtcccag agaagcgagg gcggaagaaa ctgctgtata ttttcaaaca gccttttatg    2460
agaccagtgc agaccacaca ggaggaagat ggctgctcct gtaggtttcc cgaggaagag    2520
```
gaaggaggct gtgagctgtg a                                          2541

<210> SEQ ID NO 39
<211> LENGTH: 373
<212> TYPE: PRT
<213> ORGANISM: Artificial Sequence
<220> FEATURE:
<223> OTHER INFORMATION: alpha chain of mutlti-chain chimeric antigen
      receptor

<400> SEQUENCE: 39

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
                20                  25                  30

Gly Pro Glu Leu Ile Lys Pro Gly Ala Ser Val Lys Met Ser Cys Lys
            35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

```
Lys Arg Thr Arg Lys Gly Phe Arg Leu Leu Asn Pro His Pro Lys Pro
            355                 360                 365

Asn Pro Lys Asn Asn
        370

<210> SEQ ID NO 40
<211> LENGTH: 257
<212> TYPE: PRT
<213> ORGANISM: Artificial Sequence
<220> FEATURE:
<223> OTHER INFORMATION: Beta chain of multi-chain chimeric antigen
      receptor

<400> SEQUENCE: 40

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu

<210> SEQ ID NO 41
<211> LENGTH: 173
<212> TYPE: PRT
<213> ORGANISM: Artificial Sequence
<220> FEATURE:
<223> OTHER INFORMATION: Gamma chain of multi-chain chimeric antigen
      receptor

<400> SEQUENCE: 41

Met Ile Pro Ala Val Val Leu Leu Leu Leu Leu Leu Val Glu Gln Ala
```

```
1               5                   10                  15
Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Arg Val Lys
            50                  55                  60

Phe Ser Arg Ser Ala Asp Ala Pro Ala Tyr Gln Gln Gly Gln Asn Gln
65                      70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
                100                 105                 110

Lys Asn Pro Gln Glu Gly Leu Tyr Asn Glu Leu Gln Lys Asp Lys Met
            115                 120                 125

Ala Glu Ala Tyr Ser Glu Ile Gly Met Lys Gly Glu Arg Arg Arg Gly
130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg
                165                 170
```

<210> SEQ ID NO 42
<211> LENGTH: 852
<212> TYPE: DNA
<213> ORGANISM: Artificial Sequence
<220> FEATURE:
<223> OTHER INFORMATION: scFV-GG

<400> SEQUENCE: 42

```
gaagacacat ggctcccgca atggagtccc ctacactgct gtgcgtggca ctgctgttct      60
ttgcaccaga tggcgtgctg gcagaggtcc agctgcagca gtcaggacca gaactgatca     120
aacccggagc atctgtgaaa atgagttgta aggcctcagg ctatactttc acctcttacg     180
tgatgcactg ggtcaagcag aaacctggac agggcctgga gtggatcggc tatattaatc     240
catacaacga cggaccaagt acaacgaaag tttaaaggca aggcaacact gactagtgat     300
aagagctcct ctactgctac atggagctga gttcactgac cagcgaggac tccgctgtgt     360
actattgtgc aagaggaacc tactatacgg ctctaggtgt tcgatactgg gggcagggaa     420
ccacactgac agtcagctcc ggaggaggag ggtccggagg agggggtctg gaggcggggg     480
aagtgacatc gtgatgacac aggccgctcc tagcattcca gtgactcccg gcgagtcagt     540
cagcatctcc tgtcggtctc gtagagagcc tgctgaactc caatggaaac acatatctgt     600
actggtttct gcagaggcct ggccagtccc cacagctgct gatctatcgc atgtctaacc     660
tggccagtgg cgtgcccgat cggttctctg gcagtgggtc aggaaccgcc tttacactga     720
ggatatagcc gcgtcgaggc tgaggacgtg ggggtctatt actgcatgca gcatctggagt     780
accctttcac atttggcgcc gggactaaac tggaactgaa gcgctcggat cccggaagac     840
gtcttc                                                                 852
```

<210> SEQ ID NO 43
<211> LENGTH: 315
<212> TYPE: DNA
<213> ORGANISM: Artificial Sequence
<220> FEATURE:
<223> OTHER INFORMATION: hinge-trans-intra-GG

<400> SEQUENCE: 43

```
gaagacactc ccactaccac accagctcca cgaccaccta ctcctgcacc aaccattgct    60
tcacagcctc tgagcctgcg accagaagcc tgccggccag cagcaggagg agcagtgcac   120
accagaggcc tggacttcgc ctgtgatttc tttatccccc tgctggtggt cattctgttc   180
gccgtggaca ctgggctgtt tatctccacc cagcagcagg tcacattcct gctgaaaatt   240
aagcggacca gaaagggctt ccggctgctg aatccccatc ctaaaccaaa ccccaagaac   300
aatgaatacg tcttc                                                    315
```

<210> SEQ ID NO 44
<211> LENGTH: 324
<212> TYPE: DNA
<213> ORGANISM: Artificial Sequence
<220> FEATURE:
<223> OTHER INFORMATION: FRB-GG

<400> SEQUENCE: 44

```
gaagacacga agcggaggca gggttgctat cctttggcat gaaatgtggc atgaggggct    60
cgaggaggcc agtcggctgt acttcggaga aagaaatgtg aagggtatgt tcgaggtctt   120
ggaacccctg cacgccatga tggagcgagg cctcaaaccc tcaaggaga catctttaa   180
ccaggcatat ggtagggatc tcatggaagc ccaggaatgg tgcagaaaat acatgaaatc   240
cggcaacgtg aaggacctga ctcaggcttg ggacctgtat taccacgtat ttcggcgcat   300
tggcagcggg gctcccacgt cttc                                          324
```

<210> SEQ ID NO 45
<211> LENGTH: 360
<212> TYPE: DNA
<213> ORGANISM: Artificial Sequence
<220> FEATURE:
<223> OTHER INFORMATION: FKBP-GG

<400> SEQUENCE: 45

```
gaagacacga agcggaggcg tgcaagtcga gactatttca ccaggcgacg gtagaacttt    60
tccaaaacgg ggtcagacct gcgtcgttca ttacacaggc atgctcgagg atggcaagaa   120
gtttgactct agtagggatc gtaacaaacc cttcaagttc atgctgggta agcaggaggt   180
gatccgcggc tgggaggaag gggtggcaca gatgtctgtg ggacagcgag ccaagctgac   240
catcagccct gattatgctt acggagccac cgggcacccc ggtatcatac ctccccacgc   300
tacactggtt ttcgacgtag aactccttaa attggaaggc agcggggctc ccacgtcttc   360
```

<210> SEQ ID NO 46
<211> LENGTH: 223
<212> TYPE: PRT
<213> ORGANISM: Artificial Sequence
<220> FEATURE:
<223> OTHER INFORMATION: FRB-FKBP fragment including a GS-4x-EAAAR-
      linker

<400> SEQUENCE: 46

Arg Val Ala Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
            20                  25                  30

Val Leu Glu Pro Leu His Ala Met Met Glu Arg Gly Pro Gln Thr Leu
        35                  40                  45

```
Lys Glu Thr Ser Phe Asn Gln Ala Tyr Gly Arg Asp Leu Met Glu Ala
     50                  55                  60

Gln Glu Trp Cys Arg Lys Tyr Met Lys Ser Gly Asn Val Lys Asp Leu
 65                  70                  75                  80

Thr Gln Ala Trp Asp Leu Tyr Tyr His Val Phe Arg Arg Ile Gly Ser
                 85                  90                  95

Glu Ala Ala Ala Arg Glu Ala Ala Ala Arg Glu Ala Ala Ala Arg Glu
            100                 105                 110

Ala Ala Ala Arg Gly Val Gln Val Glu Thr Ile Ser Pro Gly Asp Gly
            115                 120                 125

Arg Thr Phe Pro Lys Arg Gly Gln Thr Cys Val Val His Tyr Thr Gly
    130                 135                 140

Met Leu Glu Asp Gly Lys Lys Phe Asp Ser Ser Arg Asp Arg Asn Lys
145                 150                 155                 160

Pro Phe Lys Phe Met Leu Gly Lys Gln Glu Val Ile Arg Gly Trp Glu
                165                 170                 175

Glu Gly Val Ala Gln Met Ser Val Gly Gln Arg Ala Lys Leu Thr Ile
            180                 185                 190

Ser Pro Asp Tyr Ala Tyr Gly Ala Thr Gly His Pro Gly Ile Ile Pro
            195                 200                 205

Pro His Ala Thr Leu Val Phe Asp Val Glu Leu Leu Lys Leu Glu
    210                 215                 220

<210> SEQ ID NO 47
<211> LENGTH: 222
<212> TYPE: PRT
<213> ORGANISM: Artificial Sequence
<220> FEATURE:
<223> OTHER INFORMATION: FKBP-FRB fragment including a four-EAAAR-linker

<400> SEQUENCE: 47

Gly Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Glu Glu Ala Ala Ala Arg
            100                 105                 110

Glu Ala Ala Ala Arg Glu Ala Ala Ala Arg Glu Ala Ala Ala Arg Gly
            115                 120                 125

Arg Val Ala Ile Leu Trp His Glu Met Trp His Glu Gly Leu Glu Glu
    130                 135                 140

Ala Ser Arg Leu Tyr Phe Gly Glu Arg Asn Val Lys Gly Met Phe Glu
145                 150                 155                 160

Val Leu Glu Pro Leu His Ala Met Met Glu Arg Gly Pro Gln Thr Leu
                165                 170                 175

Lys Glu Thr Ser Phe Asn Gln Ala Tyr Gly Arg Asp Leu Met Glu Ala
            180                 185                 190
```

Gln Glu Trp Cys Arg Lys Tyr Met Lys Ser Gly Asn Val Lys Asp Leu
          195                 200                 205

Thr Gln Ala Trp Asp Leu Tyr Tyr His Val Phe Arg Arg Ile
    210                 215                 220

<210> SEQ ID NO 48
<211> LENGTH: 1470
<212> TYPE: DNA
<213> ORGANISM: Artificial Sequence
<220> FEATURE:
<223> OTHER INFORMATION: Construct pCLS26563

<400> SEQUENCE: 48

| | | | | | |
|---|---|---|---|---|---|
| atggctcccg | caatggagtc | ccctacactg | ctgtgcgtgg | cactgctgtt | ctttgcacca | 60 |
| gatggcgtgc | tggcagaggt | ccagctgcag | cagtcaggac | cagaactgat | caaacccgga | 120 |
| gcatctgtga | aaatgagttg | taaggcctca | ggctatactt | tcacctctta | cgtgatgcac | 180 |
| tgggtcaagc | agaaacctgg | acagggcctg | gagtggatcg | gctatattaa | tccatacaac | 240 |
| gacgggacca | agtacaacga | aaagtttaaa | ggcaaggcaa | cactgactag | tgataagagc | 300 |
| tcctctactg | cttacatgga | gctgagttca | ctgaccagcg | aggactccgc | tgtgtactat | 360 |
| tgcgcaagag | gaacctacta | ttacggctct | agggtgttcg | attactgggg | cagggaacc | 420 |
| acactgacag | tcagctccgg | aggaggaggg | tccggaggag | agggtctgg | aggcggggga | 480 |
| agtgacatcg | tgatgacaca | ggccgctcct | agcattccag | tgactcccgg | cgagtcagtc | 540 |
| agcatctcct | gtcggtctag | taagagcctg | ctgaactcca | atggaaacac | atatctgtac | 600 |
| tggtttctgc | agaggcctgg | ccagtcccca | cagctgctga | tctatcgcat | gtctaacctg | 660 |
| gccagtggcg | tgcccgatcg | gttctctggc | agtgggtcag | gaaccgcctt | tacactgagg | 720 |
| attagccgcg | tcgaggctga | ggacgtgggg | gtctattact | gcatgcagca | tctggagtac | 780 |
| ccttcacat | ttggcgccgg | gactaaactg | gaactgaagc | gctcggatcc | cggaagcgga | 840 |
| ggcgtgcaag | tcgagactat | ttcaccaggc | gacggtagaa | cttttccaaa | acggggtcag | 900 |
| acctgcgtcg | ttcattacac | aggcatgctc | gaggatggca | agaagtttga | ctctagtagg | 960 |
| gatcgtaaca | acccttcaa | gttcatgctg | ggtaagcagg | aggtgatccg | cggctgggag | 1020 |
| gaaggggtgg | cacagatgtc | tgtgggacag | cgagccaagc | tgaccatcag | ccctgattat | 1080 |
| gcttacggag | ccaccgggca | ccccggtatc | atacctcccc | acgctacact | ggttttcgac | 1140 |
| gtagaactcc | ttaaattgga | aggcagcggg | gctcccacta | ccacaccagc | tccacgacca | 1200 |
| cctactcctg | caccaaccat | tgcttcacag | cctctgagcc | tgcgaccaga | agcctgccgg | 1260 |
| ccagcagcag | gaggagcagt | gcacaccaga | ggcctggact | tcgcctgtga | tttctttatc | 1320 |
| cccctgctgg | tggtcattct | gttcgccgtg | acactgggc | tgtttatctc | cacccagcag | 1380 |
| caggtcacat | tcctgctgaa | aattaagcgg | accagaaagg | gcttccggct | gctgaatccc | 1440 |
| catcctaaac | caaaccccaa | gaacaatgaa | | | | 1470 |

<210> SEQ ID NO 49
<211> LENGTH: 1434
<212> TYPE: DNA
<213> ORGANISM: Artificial Sequence
<220> FEATURE:
<223> OTHER INFORMATION: Construct pCLS26564

<400> SEQUENCE: 49

| | | | | | |
|---|---|---|---|---|---|
| atggctcccg | caatggagtc | ccctacactg | ctgtgcgtgg | cactgctgtt | ctttgcacca | 60 |
| gatggcgtgc | tggcagaggt | ccagctgcag | cagtcaggac | cagaactgat | caaacccgga | 120 |

```
gcatctgtga aaatgagttg taaggcctca ggctatactt tcacctctta cgtgatgcac        180
tgggtcaagc agaaacctgg acagggcctg gagtggatcg gctatattaa tccatacaac        240
gacgggacca agtacaacga aaagtttaaa ggcaaggcaa cactgactag tgataagagc        300
tcctctactg cttacatgga gctgagttca ctgaccagcg aggactccgc tgtgtactat        360
tgcgcaagag gaacctacta ttacggctct agggtgttcg attactgggg gcagggaacc        420
acactgacag tcagctccgg aggaggaggg tccggaggag gagggtctgg aggcggggga        480
agtgacatcg tgatgacaca ggccgctcct agcattccag tgactcccgg cgagtcagtc        540
agcatctcct gtcggtctag taagagcctg ctgaactcca atggaaacac atatctgtac        600
tggtttctgc agaggcctgg ccagtcccca cagctgctga tctatcgcat gtctaacctg        660
gccagtggcg tgcccgatcg gttctctggc agtgggtcag gaaccgcctt tacactgagg        720
attagccgcg tcgaggctga ggacgtgggg gtctattact gcatgcagca tctggagtac        780
cctttcacat ttggcgccgg gactaaactg gaactgaagc gctcggatcc cggaagcgga        840
ggcagggttg ctatccttg gcatgaaatg tggcatgagg ggctcgagga ggccagtcgg        900
ctgtacttcg gagaaagaaa tgtgaagggt atgttcgagg tcttggaacc cctgcacgcc        960
atgatggagc gagggcctca aaccctcaag gagacatctt ttaaccaggc atatggtagg       1020
gatctcatgg aagcccagga atggtgcaga aaatacatga atccggcaa cgtgaaggac        1080 ctgactcagg cttgggacct gtattaccac gtatttcggc gcattggcag cggggctccc       1140
actaccacac cagctccacg accacctact cctgcaccaa ccattgcttc acagcctctg       1200
agcctgcgac cagaagcctg ccggccagca gcaggaggag cagtgcacac cagaggcctg       1260
gacttcgcct gtgatttctt tatccccctg ctggtggtca ttctgttcgc cgtggacact       1320
gggctgttta tctccaccca gcagcaggtc acattcctgc tgaaaattaa gcggaccaga       1380
aagggcttcc ggctgctgaa tcccatcct aaaccaaacc ccaagaacaa tgaa              1434
```

<210> SEQ ID NO 50
<211> LENGTH: 1815
<212> TYPE: DNA
<213> ORGANISM: Artificial Sequence
<220> FEATURE:
<223> OTHER INFORMATION: Construct pCLS26881

<400> SEQUENCE: 50

```
atggctcccg caatggagtc ccctacactg ctgtgcgtgg cactgctgtt ctttgcacca         60
gatggcgtgc tggcagaggt ccagctgcag cagtcaggac cagaactgat caaacccgga        120
gcatctgtga aaatgagttg taaggcctca ggctatactt tcacctctta cgtgatgcac        180
tgggtcaagc agaaacctgg acagggcctg gagtggatcg gctatattaa tccatacaac        240
gacgggacca agtacaacga aaagtttaaa ggcaaggcaa cactgactag tgataagagc        300
tcctctactg cttacatgga gctgagttca ctgaccagcg aggactccgc tgtgtactat        360
tgcgcaagag gaacctacta ttacggctct agggtgttcg attactgggg gcagggaacc        420
acactgacag tcagctccgg aggaggaggg tccggaggag gagggtctgg aggcggggga        480
agtgacatcg tgatgacaca ggccgctcct agcattccag tgactcccgg cgagtcagtc        540
agcatctcct gtcggtctag taagagcctg ctgaactcca atggaaacac atatctgtac        600
tggtttctgc agaggcctgg ccagtcccca cagctgctga tctatcgcat gtctaacctg        660
gccagtggcg tgcccgatcg gttctctggc agtgggtcag gaaccgcctt tacactgagg        720
```

```
attagccgcg tcgaggctga ggacgtgggg gtctattact gcatgcagca tctggagtac      780
cctttcacat ttggcgccgg gactaaactg gaactgaagc gctcggatcc cggaagcgga      840
ggcgtgcaag tcgagactat ttcaccaggc gacggtagaa cttttccaaa acgggtcag      900
acctgcgtcg ttcattacac aggcatgctc gaggatggca agaagtttga ctctagtagg      960
gatcgtaaca aacccttcaa gttcatgctg ggtaagcagg aggtgatccg cggctgggag     1020
gaaggggtgg cacagatgtc tgtgggacag cgagccaagc tgaccatcag ccctgattat     1080
gcttacggag ccaccgggca ccccggtatc atacctcccc acgctacact ggttttcgac     1140
gtagaactcc ttaaattgga agaagcgcgc gctcgcgaag ctgcagcgcg agaggctgct     1200
gcccgggagg cggctgcacg gggcagggtt gctatccttt ggcatgaaat gtggcatgag     1260
gggctcgagg aggccagtcg gctgtacttc ggagaaagaa atgtgaaggg tatgttcgag     1320
gtcttggaac ccctgcacgc catgatggag cgagggcctc aaaccctcaa ggagacatct     1380
tttaaccagg catatggtag ggatctcatg gaagcccagg aatggtgcag aaaatacatg     1440
aaatccggca acgtgaagga cctgactcag gcttgggacc tgtattacca cgtatttcgg     1500
cgcattggca gcggggctcc cactaccaca ccagctccac gaccacctac tcctgcacca     1560
accattgctt cacagcctct gagcctgcga ccagaagcct gccggccagc agcaggagga     1620
gcagtgcaca ccagaggcct ggacttcgcc tgtgatttct ttatccccct gctggtggtc     1680
attctgttcg ccgtggacac tgggctgttt atctccaccc agcagcaggt cacattcctg     1740
ctgaaaatta gcggaccag aaagggcttc cggctgctga atccccatcc taaaccaaac     1800
cccaagaaca atgaa                                                      1815
```

<210> SEQ ID NO 51
<211> LENGTH: 1821
<212> TYPE: DNA
<213> ORGANISM: Artificial Sequence
<220> FEATURE:
<223> OTHER INFORMATION: Construct pCLS27123

<400> SEQUENCE: 51

```
atggctcccg caatggagtc ccctacactg ctgtgcgtgg cactgctgtt ctttgcacca       60
gatggcgtgc tggcagaggt ccagctgcag cagtcaggac agaactgat caaacccgga      120
gcatctgtga aaatgagttg taaggcctca ggctatactt tcacctctta cgtgatgcac      180
tgggtcaagc agaaacctgg acagggcctg gagtggatcg gctatattaa tccatacaac      240
gacgggacca gtacaacga aaagtttaaa ggcaaggcaa cactgactag tgataagagc      300
tcctctactg cttacatgga gctgagttca ctgaccagcg aggactccgc tgtgtactat      360
tgcgcaagag gaacctacta ttacggctct agggtgttcg attactgggg gcagggaacc      420
acactgacag tcagctccgg aggaggaggg tccggaggag gagggtctgg aggcggggga      480
agtgacatcg tgatgacaca ggccgctcct agcattccag tgactcccgg cgagtcagtc      540
agcatctcct gtcggtctag taagagcctg ctgaactcca atggaaacac atatctgtac      600
tggtttctgc agaggcctgg ccagtcccca cagctgctga tctatcgcat gtctaacctg      660
gccagtggcg tgcccgatcg gttctctggc agtgggtcag gaaccgcctt tacactgagg      720
attagccgcg tcgaggctga ggacgtgggg gtctattact gcatgcagca tctggagtac      780
cctttcacat ttggcgccgg gactaaactg gaactgaagc gctcggatcc cggaagcgga      840
ggcagggttt ctatccttg gcatgaaatg tggcatgagg gctcgaggag gccagtcgg      900
ctgtacttcg gagaaagaaa tgtgaagggt atgttcgagg tcttggaacc cctgcacgcc      960
```

```
atgatggagc gagggcctca aaccctcaag gagacatctt ttaaccaggc atatggtagg    1020
gatctcatgg aagcccagga atggtgcaga aaatacatga atccggcaa cgtgaaggac    1080 ctgactcagg cttgggacct gtattaccac gtatttcggc gcattggcag cgaagcagcg    1140
gctcgcgaag ctgcagcgcg agaggctgct gcccgggagg cggctgcacg gggcgtgcaa    1200
gtcgagacta tttcaccagg cgacggtaga acttttccaa acgggtca gacctgcgtc     1260 gttcattaca caggcatgct cgaggatggc aagaagtttg actctagtag ggatcgtaac    1320
aaacccttca agttcatgct gggtaagcag gaggtgatcc gcggctggga ggaaggggtg    1380
gcacagatgt ctgtgggaca gcgagccaag ctgaccatca gccctgatta tgcttacgga    1440
gccaccgggc accccggtat catacctccc cacgctacac tggttttcga cgtagaactc    1500
cttaaattgg aaggcagcgg ggctcccact accacaccag ctccacgacc acctactcct    1560
gcaccaacca ttgcttcaca gcctctgagc ctgcgaccag aagcctgccg ccagcagca    1620 ggaggagcag tgcacaccag aggcctggac ttcgcctgtg atttctttat ccccctgctg    1680
gtggtcattc tgttcgccgt ggacactggg ctgtttatct ccacccagca gcaggtcaca    1740
ttcctgctga aaattaagcg gaccagaaag ggcttccggc tgctgaatcc ccatcctaaa    1800
ccaaacccca agaacaatga a                                              1821

<210> SEQ ID NO 52
<211> LENGTH: 490
<212> TYPE: PRT
<213> ORGANISM: Artificial Sequence
<220> FEATURE:
<223> OTHER INFORMATION: Construct pCLS26563 (encoded amino acid
      sequence)

<400> SEQUENCE: 52

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
```

```
            195                 200                 205
Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro Gly Ser Gly Val Gln Val Glu Thr Ile Ser
        275                 280                 285

Pro Gly Asp Gly Arg Thr Phe Pro Lys Arg Gly Gln Thr Cys Val Val
    290                 295                 300

His Tyr Thr Gly Met Leu Glu Asp Gly Lys Lys Phe Asp Ser Ser Arg
305                 310                 315                 320

Asp Arg Asn Lys Pro Phe Lys Phe Met Leu Gly Lys Gln Glu Val Ile
                325                 330                 335

Arg Gly Trp Glu Glu Gly Val Ala Gln Met Ser Val Gly Gln Arg Ala
            340                 345                 350

Lys Leu Thr Ile Ser Pro Asp Tyr Ala Tyr Gly Ala Thr Gly His Pro
        355                 360                 365

Gly Ile Ile Pro Pro His Ala Thr Leu Val Phe Asp Val Glu Leu Leu
    370                 375                 380

Lys Leu Glu Gly Ser Gly Ala Pro Thr Thr Thr Pro Ala Pro Arg Pro
385                 390                 395                 400

Pro Thr Pro Ala Pro Thr Ile Ala Ser Gln Pro Leu Ser Leu Arg Pro
                405                 410                 415

Glu Ala Cys Arg Pro Ala Ala Gly Gly Ala Val His Thr Arg Gly Leu
            420                 425                 430

Asp Phe Ala Cys Asp Phe Phe Ile Pro Leu Leu Val Val Ile Leu Phe
        435                 440                 445

Ala Val Asp Thr Gly Leu Phe Ile Ser Thr Gln Gln Gln Val Thr Phe
    450                 455                 460

Leu Leu Lys Ile Lys Arg Thr Arg Lys Gly Phe Arg Leu Leu Asn Pro
465                 470                 475                 480

His Pro Lys Pro Asn Pro Lys Asn Asn Glu
                485                 490

<210> SEQ ID NO 53
<211> LENGTH: 478
<212> TYPE: PRT
<213> ORGANISM: Artificial Sequence
<220> FEATURE:
<223> OTHER INFORMATION: Construct pCLS26564 (encoded amino acid
      sequence)

<400> SEQUENCE: 53

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60
```

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro Gly Ser Gly Gly Arg Val Ala Ile Leu Trp His
        275                 280                 285

Glu Met Trp His Glu Gly Leu Glu Glu Ala Ser Arg Leu Tyr Phe Gly
    290                 295                 300

Glu Arg Asn Val Lys Gly Met Phe Glu Val Leu Glu Pro Leu His Ala
305                 310                 315                 320

Met Met Glu Arg Gly Pro Gln Thr Leu Lys Glu Thr Ser Phe Asn Gln
                325                 330                 335

Ala Tyr Gly Arg Asp Leu Met Glu Ala Gln Glu Trp Cys Arg Lys Tyr
            340                 345                 350

Met Lys Ser Gly Asn Val Lys Asp Leu Thr Gln Ala Trp Asp Leu Tyr
        355                 360                 365

Tyr His Val Phe Arg Arg Ile Gly Ser Gly Ala Pro Thr Thr Thr Pro
    370                 375                 380

Ala Pro Arg Pro Pro Thr Pro Ala Pro Thr Ile Ala Ser Gln Pro Leu
385                 390                 395                 400

Ser Leu Arg Pro Glu Ala Cys Arg Pro Ala Ala Gly Gly Ala Val His
                405                 410                 415

Thr Arg Gly Leu Asp Phe Ala Cys Asp Phe Phe Ile Pro Leu Leu Val
            420                 425                 430

Val Ile Leu Phe Ala Val Asp Thr Gly Leu Phe Ile Ser Thr Gln Gln
        435                 440                 445

Gln Val Thr Phe Leu Leu Lys Ile Lys Arg Thr Arg Lys Gly Phe Arg
    450                 455                 460

Leu Leu Asn Pro His Pro Lys Pro Asn Pro Lys Asn Asn Glu
465                 470                 475

-continued

```
<210> SEQ ID NO 54
<211> LENGTH: 605
<212> TYPE: PRT
<213> ORGANISM: Artificial Sequence
<220> FEATURE:
<223> OTHER INFORMATION: Construct pCLS26881 (encoded amino acid
      sequence)

<400> SEQUENCE: 54

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Ser Gly Gly Gly Ser Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro Gly Ser Gly Gly Val Gln Val Glu Thr Ile Ser
        275                 280                 285

Pro Gly Asp Gly Arg Thr Phe Pro Lys Arg Gly Gln Thr Cys Val Val
    290                 295                 300

His Tyr Thr Gly Met Leu Glu Asp Gly Lys Lys Phe Asp Ser Ser Arg
305                 310                 315                 320

Asp Arg Asn Lys Pro Phe Lys Phe Met Leu Gly Lys Gln Glu Val Ile
                325                 330                 335

Arg Gly Trp Glu Glu Gly Val Ala Gln Met Ser Val Gly Gln Arg Ala
            340                 345                 350

Lys Leu Thr Ile Ser Pro Asp Tyr Ala Tyr Gly Ala Thr Gly His Pro
        355                 360                 365
```

```
Gly Ile Ile Pro Pro His Ala Thr Leu Val Phe Asp Val Glu Leu Leu
    370                 375                 380

Lys Leu Glu Glu Ala Ala Ala Arg Glu Ala Ala Ala Arg Glu Ala Ala
385                 390                 395                 400

Ala Arg Glu Ala Ala Ala Arg Gly Arg Val Ala Ile Leu Trp His Glu
                405                 410                 415

Met Trp His Glu Gly Leu Glu Glu Ala Ser Arg Leu Tyr Phe Gly Glu
            420                 425                 430

Arg Asn Val Lys Gly Met Phe Glu Val Leu Glu Pro Leu His Ala Met
                435                 440                 445

Met Glu Arg Gly Pro Gln Thr Leu Lys Glu Thr Ser Phe Asn Gln Ala
450                 455                 460

Tyr Gly Arg Asp Leu Met Glu Ala Gln Glu Trp Cys Arg Lys Tyr Met
465                 470                 475                 480

Lys Ser Gly Asn Val Lys Asp Leu Thr Gln Ala Trp Asp Leu Tyr Tyr
                485                 490                 495

His Val Phe Arg Arg Ile Gly Ser Gly Ala Pro Thr Thr Thr Pro Ala
                500                 505                 510

Pro Arg Pro Pro Thr Pro Ala Pro Thr Ile Ala Ser Gln Pro Leu Ser
            515                 520                 525

Leu Arg Pro Glu Ala Cys Arg Pro Ala Ala Gly Gly Ala Val His Thr
530                 535                 540

Arg Gly Leu Asp Phe Ala Cys Asp Phe Phe Ile Pro Leu Leu Val Val
545                 550                 555                 560

Ile Leu Phe Ala Val Asp Thr Gly Leu Phe Ile Ser Thr Gln Gln Gln
                565                 570                 575

Val Thr Phe Leu Leu Lys Ile Lys Arg Thr Arg Lys Gly Phe Arg Leu
                580                 585                 590

Leu Asn Pro His Pro Lys Pro Asn Pro Lys Asn Asn Glu
                595                 600                 605

<210> SEQ ID NO 55
<211> LENGTH: 607
<212> TYPE: PRT
<213> ORGANISM: Artificial Sequence
<220> FEATURE:
<223> OTHER INFORMATION: Construct pCLS27123 (encoded amino acid
      sequence)

<400> SEQUENCE: 55

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
                20                  25                  30

Gly Pro Glu Leu Ile Lys Pro Gly Ala Ser Val Lys Met Ser Cys Lys
            35                  40                  45

Ala Ser Gly Tyr Thr Phe Thr Ser Tyr Val Met His Trp Val Lys Gln
        50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125
```

-continued

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
            165                 170                 175

Gly Glu Ser Val Ser Ile Ser Cys Arg Ser Ser Lys Ser Leu Leu Asn
                180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
            245                 250                 255

His Leu Glu Tyr Pro Phe Thr Phe Gly Ala Gly Thr Lys Leu Glu Leu
                260                 265                 270

Lys Arg Ser Asp Pro Gly Ser Gly Gly Arg Val Ala Ile Leu Trp His
        275                 280                 285

Glu Met Trp His Glu Gly Leu Glu Glu Ala Ser Arg Leu Tyr Phe Gly
    290                 295                 300

Glu Arg Asn Val Lys Gly Met Phe Glu Val Leu Glu Pro Leu His Ala
305                 310                 315                 320

Met Met Glu Arg Gly Pro Gln Thr Leu Lys Glu Thr Ser Phe Asn Gln
            325                 330                 335

Ala Tyr Gly Arg Asp Leu Met Glu Ala Gln Glu Trp Cys Arg Lys Tyr
                340                 345                 350

Met Lys Ser Gly Asn Val Lys Asp Leu Thr Gln Ala Trp Asp Leu Tyr
        355                 360                 365

Tyr His Val Phe Arg Arg Ile Gly Ser Glu Ala Ala Ala Arg Glu Ala
    370                 375                 380

Ala Ala Arg Glu Ala Ala Ala Arg Glu Ala Ala Ala Arg Gly Val Gln
385                 390                 395                 400

Val Glu Thr Ile Ser Pro Gly Asp Gly Arg Thr Phe Pro Lys Arg Gly
            405                 410                 415

Gln Thr Cys Val Val His Tyr Thr Gly Met Leu Glu Asp Gly Lys Lys
                420                 425                 430

Phe Asp Ser Ser Arg Asp Arg Asn Lys Pro Phe Lys Phe Met Leu Gly
        435                 440                 445

Lys Gln Glu Val Ile Arg Gly Trp Glu Glu Gly Val Ala Gln Met Ser
    450                 455                 460

Val Gly Gln Arg Ala Lys Leu Thr Ile Ser Pro Asp Tyr Ala Tyr Gly
465                 470                 475                 480

Ala Thr Gly His Pro Gly Ile Ile Pro Pro His Ala Thr Leu Val Phe
            485                 490                 495

Asp Val Glu Leu Leu Lys Leu Glu Gly Ser Gly Ala Pro Thr Thr Thr
                500                 505                 510

Pro Ala Pro Arg Pro Pro Thr Pro Ala Pro Thr Ile Ala Ser Gln Pro
        515                 520                 525

Leu Ser Leu Arg Pro Glu Ala Cys Arg Pro Ala Ala Gly Gly Ala Val
    530                 535                 540

His Thr Arg Gly Leu Asp Phe Ala Cys Asp Phe Ile Pro Leu Leu
545                 550                 555                 560

Val Val Ile Leu Phe Ala Val Asp Thr Gly Leu Phe Ile Ser Thr Gln
            565                 570                 575

Gln Gln Val Thr Phe Leu Leu Lys Ile Lys Arg Thr Arg Lys Gly Phe
            580                 585                 590

Arg Leu Leu Asn Pro His Pro Lys Pro Asn Pro Lys Asn Asn Glu
            595                 600                 605

<210> SEQ ID NO 56
<211> LENGTH: 55
<212> TYPE: DNA
<213> ORGANISM: Artificial Sequence
<220> FEATURE:
<223> OTHER INFORMATION: Oligonucleotide primer (alpha-chain forward)

<400> SEQUENCE: 56
gcatcgtaat acgactcact atagggcagg ccaccatggc tcccgcaatg gagtc       55

<210> SEQ ID NO 57
<211> LENGTH: 22
<212> TYPE: DNA
<213> ORGANISM: Artificial Sequence
<220> FEATURE:
<223> OTHER INFORMATION: Oligonucleotide primer (alpha-chain reverse)

<400> SEQUENCE: 57
tcaattgttc ttggggtttg gt                                           22

<210> SEQ ID NO 58
<211> LENGTH: 54
<212> TYPE: DNA
<213> ORGANISM: Artificial Sequence
<220> FEATURE:
<223> OTHER INFORMATION: Oligonucleotide primer (beta-chain forward)

<400> SEQUENCE: 58
gcatcgtaat acgactcact atagggcagg ccaccatgga cactgagtct aacc        54

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide primer (beta-chain reverse)

<400> SEQUENCE: 59
tcacagctca cagcctcctt                                              20

<210> SEQ ID NO 60
<211> LENGTH: 55
<212> TYPE: DNA
<213> ORGANISM: Artificial Sequence
<220> FEATURE:
<223> OTHER INFORMATION: Oligonucleotide primer (gamma-chain forward)

<400> SEQUENCE: 60
gcatcgtaat acgactcact atagggcagg ccaccatgat cccagccgtg gtcct       55

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide primer (gamma-chain reverse)

<400> SEQUENCE: 61
tcagcgaggg ggcagggcct                                            20

<210> SEQ ID NO 62
<211> LENGTH: 222
<212> TYPE: PRT
<213> ORGANISM: Artificial Sequence
<220> FEATURE:
<223> OTHER INFORMATION: FKBP-FRB* domain including a four-EAAAR-
      linker; FRB* refers to a variant of FRB having the T2098L mutation
      (SEQ ID NO: 4)

<400> SEQUENCE: 62

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Glu Ala Ala Ala Arg
            100                 105                 110

Glu Ala Ala Ala Arg Glu Ala Ala Ala Arg Glu Ala Ala Ala Arg Gly
        115                 120                 125

Arg Val Ala Ile Leu Trp His Glu Met Trp His Glu Gly Leu Glu Glu
    130                 135                 140

Ala Ser Arg Leu Tyr Phe Gly Glu Arg Asn Val Lys Gly Met Phe Glu
145                 150                 155                 160

Val Leu Glu Pro Leu His Ala Met Met Glu Arg Gly Pro Gln Thr Leu
                165                 170                 175

Lys Glu Thr Ser Phe Asn Gln Ala Tyr Gly Arg Asp Leu Met Glu Ala
            180                 185                 190

Gln Glu Trp Cys Arg Lys Tyr Met Lys Ser Gly Asn Val Lys Asp Leu
        195                 200                 205

Leu Gln Ala Trp Asp Leu Tyr Tyr His Val Phe Arg Arg Ile
    210                 215                 220

<210> SEQ ID NO 63
<211> LENGTH: 1815
<212> TYPE: DNA
<213> ORGANISM: Artificial Sequence
<220> FEATURE:
<223> OTHER INFORMATION: Construct pCLS27039

<400> SEQUENCE: 63
atggctcccg caatggagtc ccctacactg ctgtgcgtgg cactgctgtt ctttgcacca    60
gatggcgtgc tggcagaggt ccagctgcag cagtcaggac agaactgat caaacccgga   120 gcatctgtga aaatgagttg taaggcctca ggctatactt tcacctctta cgtgatgcac   180
tgggtcaagc agaaacctgg acagggcctg agtggatcg gctatattaa tccatacaac   240
gacgggacca agtacaacga aaagtttaaa ggcaaggcaa cactgactag tgataagagc   300

```
tcctctactg cttacatgga gctgagttca ctgaccagcg aggactccgc tgtgtactat      360
tgcgcaagag gaacctacta ttacggctct agggtgttcg attactgggg cagggaacc       420 acactgacag tcagctccgg aggaggaggg tccggaggag agggtctgga aggcggggga      480
agtgacatcg tgatgacaca ggccgctcct agcattccag tgactcccgg cgagtcagtc      540
agcatctcct gtcggtctag taagagcctg ctgaactcca atggaaacac atatctgtac      600
tggtttctgc agaggcctgg ccagtcccca cagctgctga tctatcgcat gtctaacctg      660
gccagtggcg tgcccgatcg gttctctggc agtgggtcag gaaccgcctt tacactgagg      720
attagccgcg tcgaggctga ggacgtgggg gtctattact gcatgcagca tctggagtac      780
cctttcacat ttggcgccgg gactaaactg gaactgaagc gctcggatcc cggaagcgga      840
ggcgtgcaag tcgagactat ttcaccaggc gacggtagaa cttttccaaa acggggtcag      900
acctgcgtcg ttcattacac aggcatgctc gaggatggca agaagtttga ctctagtagg      960
gatcgtaaca aacccttcaa gttcatgctg ggtaagcagg aggtgatccg cggctgggag     1020
gaaggggtgg cacagatgtc tgtgggacag cgagccaagc tgaccatcag ccctgattat     1080
gcttacggag ccaccgggca ccccggtatc ataccctccc cacgctacac tggttttcgac    1140 gtagaactcc ttaaattgga agaagcagcg gctcgcgaag ctgcagcgcg agaggctgct     1200
gcccgggagg cggctgcacg gggcagggtt gctatccttt ggcatgaaat gtggcatgag     1260
gggctcgagg aggccagtcg gctgtacttc ggagaaagaa atgtgaaggg tatgttcgag     1320
gtcttggaac ccctgcacgc catgatggag cgagggcctc aaaccctcaa ggagacatct     1380
tttaaccagg catatggtag ggatctcatg aagcccagg aatggtgcag aaaatacatg      1440
aaatccggca acgtgaagga cctgctccag gcttgggacc tgtattacca cgtatttcgg     1500
cgcattggca gcggggctcc cactaccaca ccagctccac gaccacctac tcctgcacca     1560
accattgctt cacagcctct gagcctgcga ccagaagcct gccggccagc agcaggagga    1620
gcagtgcaca ccagaggcct ggacttcgcc tgtgatttct ttatcccct gctggtggtc     1680 attctgttcg ccgtggacac tgggctgttt atctccaccc agcagcaggt cacattcctg    1740
ctgaaaatta gcggaccag aaagggcttc cggctgctga atccccatcc taaaccaaac    1800
cccaagaaca atgaa                                                     1815
```

<210> SEQ ID NO 64
<211> LENGTH: 605
<212> TYPE: PRT
<213> ORGANISM: Artificial Sequence
<220> FEATURE:
<223> OTHER INFORMATION: Construct pCLS27039 (encoded amino acid
      sequence)

<400> SEQUENCE: 64

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr

```
                  85                  90                  95
Ser Asp Lys Ser Ser Ser Thr Ala Tyr Met Glu Leu Ser Ser Leu Thr
                100                 105                 110

Ser Glu Asp Ser Ala Val Tyr Tyr Cys Ala Arg Gly Thr Tyr Tyr Tyr
                115                 120                 125

Gly Ser Arg Val Phe Asp Tyr Trp Gly Gln Gly Thr Thr Leu Thr Val
            130                 135                 140

Ser Ser Gly Gly Gly Gly Ser Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
                180                 185                 190

Ser Asn Gly Asn Thr Tyr Leu Tyr Trp Phe Leu Gln Arg Pro Gly Gln
            195                 200                 205

Ser Pro Gln Leu Leu Ile Tyr Arg Met Ser Asn Leu Ala Ser Gly Val
            210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
                260                 265                 270

Lys Arg Ser Asp Pro Gly Ser Gly Gly Val Gln Val Glu Thr Ile Ser
            275                 280                 285

Pro Gly Asp Gly Arg Thr Phe Pro Lys Arg Gly Gln Thr Cys Val Val
290                 295                 300

His Tyr Thr Gly Met Leu Glu Asp Gly Lys Lys Phe Asp Ser Ser Arg
305                 310                 315                 320

Asp Arg Asn Lys Pro Phe Lys Phe Met Leu Gly Lys Gln Glu Val Ile
                325                 330                 335

Arg Gly Trp Glu Glu Gly Val Ala Gln Met Ser Val Gly Gln Arg Ala
            340                 345                 350

Lys Leu Thr Ile Ser Pro Asp Tyr Ala Tyr Gly Ala Thr Gly His Pro
            355                 360                 365

Gly Ile Ile Pro Pro His Ala Thr Leu Val Phe Asp Val Glu Leu Leu
            370                 375                 380

Lys Leu Glu Glu Ala Ala Ala Arg Glu Ala Ala Ala Arg Glu Ala Ala
385                 390                 395                 400

Ala Arg Glu Ala Ala Ala Arg Gly Arg Val Ala Ile Leu Trp His Glu
                405                 410                 415

Met Trp His Glu Gly Leu Glu Glu Ala Ser Arg Leu Tyr Phe Gly Glu
            420                 425                 430

Arg Asn Val Lys Gly Met Phe Glu Val Leu Glu Pro Leu His Ala Met
            435                 440                 445

Met Glu Arg Gly Pro Gln Thr Leu Lys Glu Thr Ser Phe Asn Gln Ala
450                 455                 460

Tyr Gly Arg Asp Leu Met Glu Ala Gln Glu Trp Cys Arg Lys Tyr Met
465                 470                 475                 480

Lys Ser Gly Asn Val Lys Asp Leu Leu Gln Ala Trp Asp Leu Tyr Tyr
                485                 490                 495

His Val Phe Arg Arg Ile Gly Ser Gly Ala Pro Thr Thr Thr Pro Ala
            500                 505                 510
```

```
Pro Arg Pro Pro Thr Pro Ala Pro Thr Ile Ala Ser Gln Pro Leu Ser
        515                 520                 525

Leu Arg Pro Glu Ala Cys Arg Pro Ala Ala Gly Gly Ala Val His Thr
        530                 535                 540

Arg Gly Leu Asp Phe Ala Cys Asp Phe Phe Ile Pro Leu Leu Val Val
545                 550                 555                 560

Ile Leu Phe Ala Val Asp Thr Gly Leu Phe Ile Ser Thr Gln Gln Gln
                565                 570                 575

Val Thr Phe Leu Leu Lys Ile Lys Arg Thr Arg Lys Gly Phe Arg Leu
            580                 585                 590

Leu Asn Pro His Pro Lys Pro Asn Pro Lys Asn Asn Glu
            595                 600                 605

<210> SEQ ID NO 65
<211> LENGTH: 2169
<212> TYPE: DNA
<213> ORGANISM: Artificial Sequence
<220> FEATURE:
<223> OTHER INFORMATION: Construct pCLS27572

<400> SEQUENCE: 65
atggctctgc tgtcaccgc cctgctgctg cctctggccc tgctgctgca cgccgcacgc        60
cctcagattc agctggtcca gtccgggcct gagctgaaga aaccaggcga aaccgtgaag       120
atctcttgca agctagtgg atacattttc acaaactatg gcatgaattg ggtcaagcag       180
gccccaggga gagctttaa atggatggga tggatcaaca cttacaccgg cgagagtacc       240
tattcagctg acttcaaggg ccgcttcgca ttttccctgg aaacctcagc aagcacagcc       300
tacctgcaca ttaacgacct gaagaacgag atacagcta cttacttctg cgcacgatcc       360
ggaggatacg acccaatgga ttattgggc caggggacat ctgtgactgt cagctccgga       420
ggaggaggat ccggcggagg aggctctggg ggaggcggga gtgacatcgt gctgactcag       480
agcccagctt ccctggcagt ctcactggga cagcgcgcaa ccattagctg tcgagcctcc       540
gagtctgtgg ataactacgg caatacattc atgcattggt atcagcagaa gcctgggcag       600
ccccctaaac tgctgatcta ccgcgcctca aatctggaaa gcggcattcc agctcgcttc       660
agtggatcag gcagccggac tgactttacc ctgacaatca ccccgtggga ggcagacgat       720
gtcgccacct actattgcca gcagagtaat gaggatccac cactttttgg ggcaggaacc       780
aagctggaac tgaaacgatc ggatcccgga agcggaggcg tgcaagtcga gactatttca       840
ccaggcgacg gtagaactttt tccaaaacgg ggtcagacct gcgtcgttca ttacacaggc       900
atgctcgagg atggcaagaa gtttgactct agtagggatc gtaacaaacc cttcaagttc       960
atgctgggta gcaggaggt gatccgcggc tgggaggaag gggtggcaca gatgtctgtg      1020
ggacagcgag ccaagctgac catcagcct gattatgctt acggagccac cgggcacccc      1080
ggtatcatac ctcccacgc tacactggtt ttcgacgtag aactccttaa attggaagaa      1140
gcagcggctc gcgaagctgc agcgcgagag gctgctgccc gggaggcggc tgcacggggc      1200
agggttgcta tcctttggca tgaaatgtgg catgaggggc tcgaggaggc cagtcggctg      1260
tacttcggag aaagaaatgt gaagggtatg ttcgaggtct ggaaccccct gcacgccatg      1320
atggagcgag ggcctcaaac cctcaaggag acatcttttta accaggcata tggtagggat      1380
ctcatggaag cccaggaatg gtgcagaaaa tacatgaaat ccggcaacgt gaaggacctg      1440
ctccaggctt gggacctgta ttaccacgta tttcggcgca ttggcagcgg ggctcccacc      1500
```

| | |
|---|---:|
| acaaccccg ctccaaggcc ccctaccccc gcaccaacta ttgcctccca gccactctca | 1560 |
| ctgcggcctg aggcctgtcg gcccgctgct ggaggcgcag tgcatacaag gggcctcgat | 1620 |
| ttcgcctgcg atatttacat ctgggcaccc ctcgccggca cctgcggggt gcttctcctc | 1680 |
| tccctggtga ttaccctgta ttgcagacgg ggccggaaga agctcctcta cattttaag | 1740 |
| cagcctttca tgcggccagt gcagacaacc caagaggagg atgggtgttc ctgcagattc | 1800 |
| cctgaggaag aggaaggcgg gtgcgagctg agagtgaagt tctccaggag cgcagatgcc | 1860 |
| cccgcctatc aacagggcca gaaccagctc tacaacgagc ttaacctcgg gaggcgcgaa | 1920 |
| gaatacgacg tgttggataa agaagggggg cgggaccccg agatgggagg aaagcccccgg | 1980 |
| aggaagaacc ctcaggaggg cctgtacaac gagctgcaga aggataagat ggccgaggcc | 2040 |
| tactcagaga tcgggatgaa gggggagcgg cgccgcggga aggggcacga tgggctctac | 2100 |
| caggggctga gcacagccac aaaggacaca tacgacgcct gcacatgca ggcccttcca | 2160 |
| ccccgggaa | 2169 |

<210> SEQ ID NO 66
<211> LENGTH: 1824
<212> TYPE: DNA
<213> ORGANISM: Artificial Sequence
<220> FEATURE:
<223> OTHER INFORMATION: Construct pCLS27603

<400> SEQUENCE: 66

| | |
|---|---:|
| atggctctgc ctgtcaccgc cctgctgctg cctctggccc tgctgctgca cgccgcacgc | 60 |
| cctcagattc agctggtcca gtccgggcct gagctgaaga aaccaggcga aaccgtgaag | 120 |
| atctcttgca aagctagtgg atacattttc acaaactatg gcatgaattg ggtcaagcag | 180 |
| gccccaggga gagcttttaa atggatggga tggatcaaca cttacaccgg cgagagtacc | 240 |
| tattcagctg acttcaaggg ccgcttcgca ttttccctgg aaacctcagc aagcacagcc | 300 |
| tacctgcaca ttaacgacct gaagaacgag atacagcta cttacttctg cgcacgatcc | 360 |
| ggaggatacg acccaatgga ttattgggc caggggacat ctgtgactgt cagctccgga | 420 |
| ggaggaggat ccggcggagg aggctctggg ggaggcggga gtgacatcgt gctgactcag | 480 |
| agcccagctt ccctggcagt ctcactggga cagcgcgcaa ccattagctg tcgagcctcc | 540 |
| gagtctgtgg ataactacgg caatacattc atgcattggt atcagcagaa gcctgggcag | 600 |
| cccctaaac tgctgatcta ccgcgcctca aatctgaaa gcggcattcc agctcgcttc | 660 |
| agtggatcag gcagccggac tgactttacc ctgacaatca cccgtggaa ggcagacgat | 720 |
| gtcgccacct actattgcca gcagagtaat gaggatccac ccactttgg ggcaggaacc | 780 |
| aagctggaac tgaaacgatc ggatcccgga agcggaggcg tgcaagtcga gactatttca | 840 |
| ccaggcgacg gtagaacttt tccaaaacgg ggtcagacct gcgtcgttca ttacacaggc | 900 |
| atgctcgagg atggcaagaa gtttgactct agtagggatc gtaacaaacc cttcaagttc | 960 |
| atgctgggta gcaggaggt gatccgcggc tgggaggaag gggtggcaca gatgtctgtg | 1020 |
| ggacagcgag ccaagctgac catcagccct gattatgctt acggagccac cgggcacccc | 1080 |
| ggtatcatac ctccccacgc tacactggtt ttcgacgtag aactccttaa attggaaggc | 1140 |
| agcggggctc ccaccacaac cccgctccca aggccccta ccccgcacc aactattgcc | 1200 |
| tcccagccac tctcactgcg gcctgaggcc tgtcggcccg ctgctggagg cgcagtgcat | 1260 |
| acaaggggcc tcgatttcgc ctgcgatatt tacatctggg cacccctcgc cggcacctgc | 1320 |
| ggggtgcttc tcctctcct ggtgattacc ctgtattgca gacggggccg gaagaagctc | 1380 |

```
ctctacattt ttaagcagcc tttcatgcgg ccagtgcaga caacccaaga ggaggatggg    1440
tgttcctgca gattccctga ggaagaggaa ggcgggtgcg agctgagagt gaagttctcc    1500
aggagcgcag atgccccgc ctatcaacag ggccagaacc agctctacaa cgagcttaac    1560
ctcgggaggc gcgaagaata cgacgtgttg ataagagaa gggggcggga ccccgagatg    1620
ggaggaaagc cccggaggaa gaaccctcag gagggcctgt acaacgagct gcagaaggat    1680
aagatggccg aggcctactc agagatcggg atgaagggg agcggcgccg cgggaagggg    1740
cacgatgggc tctaccaggg gctgagcaca gccacaaagg acacatacga cgccttgcac    1800
atgcaggccc ttccaccccg ggaa                                          1824
```

<210> SEQ ID NO 67
<211> LENGTH: 1788
<212> TYPE: DNA
<213> ORGANISM: Artificial Sequence
<220> FEATURE:
<223> OTHER INFORMATION: Construct pCLS27604

<400> SEQUENCE: 67

```
atggctctgc ctgtcaccgc cctgctgctg cctctggccc tgctgctgca cgccgcacgc      60
cctcagattc agctggtcca gtccgggcct gagctgaaga accaggcga aaccgtgaag     120 atctcttgca agctagtgg atacattttc acaaactatg gcatgaattg ggtcaagcag     180
gccccaggga gagctttaa atggatggga tggatcaaca cttacaccgg cgagagtacc     240
tattcagctg acttcaaggg ccgcttcgca ttttcccctgg aaacctcagc aagcacagcc     300
tacctgcaca ttaacgacct gaagaacgag gatacagcta cttacttctg cgcacgatcc     360
ggaggatacg acccaatgga ttattggggc cagggggacat ctgtgactgt cagctccgga     420
ggaggaggat ccggcggagg aggctctggg ggaggcggga gtgacatcgt gctgactcag     480
agcccagctt ccctggcagt ctcactggga cagcgcgcaa ccattagctg tcgagcctcc     540
gagtctgtgg ataactacgg caatacattc atgcattggt atcagcagaa gcctgggcag     600
ccccctaaac tgctgatcta ccgcgcctca aatctggaaa gcggcattcc agctcgcttc     660
agtggatcag gcagccggac tgactttacc ctgacaatca accccgtgga ggcagacgat     720
gtcgccacct actattgcca gcagagtaat gaggatccac ccactttggg ggcaggaacc     780
aagctggaac tgaaacgatc ggatcccgga agcggaggcg gggttgctat cctttggcat     840
gaaatgtggc atgaggggct cgaggaggcc agtcggctgt acttcggaga agaaatgtg     900 aagggtatgt tcgaggtctt ggaacccctg cacgccatga tggagcgagg gcctcaaacc     960
ctcaaggaga catcttttaa ccaggcatat ggtagggatc tcatgaagc ccaggaatgg    1020 tgcagaaaat acatgaaatc cggcaacgtg aaggacctgc tccaggcttg ggacctgtat    1080
taccacgtat ttcggcgcat tggcagcggg gctcccacca aaccccgc tccaaggccc    1140 cctaccccg caccaactat gcctcccag ccactctcac tgcggcctga ggcctgtcgg    1200
cccgctgctg gaggcgcagt gcatacaagg ggcctcgatt tcgcctgcga tatttacatc    1260
tgggcacccc tcgccggcac ctgcgggtg cttctcctct ccctggtgat taccctgtat    1320
tgcagacggg gccggaagaa gctcctctac attttaagc agccttttcat gcggccagtg    1380 cagacaaccc aagaggagga tgggtgttcc tgcagattcc ctgaggaaga ggaaggcggg    1440
tgcgagctga gagtgaagtt ctccaggagc gcagatgccc ccgcctatca acagggccag    1500
aaccagctct acaacgagct taacctcggg aggcgcgaag aatacgacgt gttggataag    1560
```

```
agaagggggc gggaccccga gatgggagga aagccccgga ggaagaaccc tcaggagggc    1620
ctgtacaacg agctgcagaa ggataagatg gccgaggcct actcagagat cgggatgaag    1680
ggggagcggc gccgcgggaa ggggcacgat gggctctacc aggggctgag cacagccaca    1740
aaggacacat acgacgcctt gcacatgcag gcccttccac cccgggaa                 1788
```

<210> SEQ ID NO 68
<211> LENGTH: 723
<212> TYPE: PRT
<213> ORGANISM: Artificial Sequence
<220> FEATURE:
<223> OTHER INFORMATION: Construct pCLS27572 (encoded amino acid
      sequence)

<400> SEQUENCE: 68

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Ile Phe Thr Asn Tyr Gly Met Asn Trp Val Lys Gln Ala Pro Gly Lys
    50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
        195                 200                 205

Ala Ser Asn Leu Glu Ser Gly Ile Pro Ala Arg Phe Ser Gly Ser Gly
    210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
                245                 250                 255

Gly Ala Gly Thr Lys Leu Glu Leu Lys Arg Ser Asp Pro Gly Ser Gly
            260                 265                 270

Gly Val Gln Val Glu Thr Ile Ser Pro Gly Asp Gly Arg Thr Phe Pro
        275                 280                 285

Lys Arg Gly Gln Thr Cys Val Val His Tyr Thr Gly Met Leu Glu Asp
    290                 295                 300

Gly Lys Lys Phe Asp Ser Ser Arg Asp Arg Asn Lys Pro Phe Lys Phe
305                 310                 315                 320
```

Met Leu Gly Lys Gln Glu Val Ile Arg Gly Trp Glu Gly Val Ala
            325                 330                 335

Gln Met Ser Val Gly Gln Arg Ala Lys Leu Thr Ile Ser Pro Asp Tyr
        340                 345                 350

Ala Tyr Gly Ala Thr Gly His Pro Gly Ile Ile Pro Pro His Ala Thr
            355                 360                 365

Leu Val Phe Asp Val Glu Leu Lys Leu Glu Ala Ala Ala Arg
        370                 375                 380

Glu Ala Ala Arg Glu Ala Ala Arg Glu Ala Ala Arg Gly
385                 390                 395                 400

Arg Val Ala Ile Leu Trp His Glu Met Trp His Glu Gly Leu Glu Glu
            405                 410                 415

Ala Ser Arg Leu Tyr Phe Gly Glu Arg Asn Val Lys Gly Met Phe Glu
        420                 425                 430

Val Leu Glu Pro Leu His Ala Met Met Glu Arg Gly Pro Gln Thr Leu
            435                 440                 445

Lys Glu Thr Ser Phe Asn Gln Ala Tyr Gly Arg Asp Leu Met Glu Ala
    450                 455                 460

Gln Glu Trp Cys Arg Lys Tyr Met Lys Ser Gly Asn Val Lys Asp Leu
465                 470                 475                 480

Leu Gln Ala Trp Asp Leu Tyr Tyr His Val Phe Arg Arg Ile Gly Ser
            485                 490                 495

Gly Ala Pro Thr Thr Thr Pro Ala Pro Arg Pro Pro Thr Pro Ala Pro
        500                 505                 510

Thr Ile Ala Ser Gln Pro Leu Ser Leu Arg Pro Glu Ala Cys Arg Pro
            515                 520                 525

Ala Ala Gly Gly Ala Val His Thr Arg Gly Leu Asp Phe Ala Cys Asp
    530                 535                 540

Ile Tyr Ile Trp Ala Pro Leu Ala Gly Thr Cys Gly Val Leu Leu Leu
545                 550                 555                 560

Ser Leu Val Ile Thr Leu Tyr Cys Arg Arg Gly Arg Lys Lys Leu Leu
            565                 570                 575

Tyr Ile Phe Lys Gln Pro Phe Met Arg Pro Val Gln Thr Thr Gln Glu
        580                 585                 590

Glu Asp Gly Cys Ser Cys Arg Phe Pro Glu Glu Glu Gly Gly Cys
            595                 600                 605

Glu Leu Arg Val Lys Phe Ser Arg Ser Ala Asp Ala Pro Ala Tyr Gln
        610                 615                 620

Gln Gly Gln Asn Gln Leu Tyr Asn Glu Leu Asn Leu Gly Arg Arg Glu
625                 630                 635                 640

Glu Tyr Asp Val Leu Asp Lys Arg Arg Gly Arg Asp Pro Glu Met Gly
            645                 650                 655

Gly Lys Pro Arg Arg Lys Asn Pro Gln Glu Gly Leu Tyr Asn Glu Leu
        660                 665                 670

Gln Lys Asp Lys Met Ala Glu Ala Tyr Ser Glu Ile Gly Met Lys Gly
            675                 680                 685

Glu Arg Arg Arg Gly Lys Gly His Asp Gly Leu Tyr Gln Gly Leu Ser
        690                 695                 700

Thr Ala Thr Lys Asp Thr Tyr Asp Ala Leu His Met Gln Ala Leu Pro
705                 710                 715                 720

Pro Arg Glu

<210> SEQ ID NO 69

<211> LENGTH: 608
<212> TYPE: PRT
<213> ORGANISM: Artificial Sequence
<220> FEATURE:
<223> OTHER INFORMATION: Construct pCLS27603 (encoded amino acid sequence)

<400> SEQUENCE: 69

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Ile Phe Thr Asn Tyr Gly Met Asn Trp Val Lys Gln Ala Pro Gly Lys
    50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
        195                 200                 205

Ala Ser Asn Leu Glu Ser Gly Ile Pro Ala Arg Phe Ser Gly Ser Gly
    210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
                245                 250                 255

Gly Ala Gly Thr Lys Leu Glu Leu Lys Arg Ser Asp Pro Gly Ser Gly
            260                 265                 270

Gly Val Gln Val Glu Thr Ile Ser Pro Gly Asp Gly Arg Thr Phe Pro
        275                 280                 285

Lys Arg Gly Gln Thr Cys Val Val His Tyr Thr Gly Met Leu Glu Asp
    290                 295                 300

Gly Lys Lys Phe Asp Ser Ser Arg Asp Arg Asn Lys Pro Phe Lys Phe
305                 310                 315                 320

Met Leu Gly Lys Gln Glu Val Ile Arg Gly Trp Glu Glu Gly Val Ala
                325                 330                 335

Gln Met Ser Val Gly Gln Arg Ala Lys Leu Thr Ile Ser Pro Asp Tyr
            340                 345                 350

Ala Tyr Gly Ala Thr Gly His Pro Gly Ile Ile Pro Pro His Ala Thr
        355                 360                 365

Leu Val Phe Asp Val Glu Leu Leu Lys Leu Glu Gly Ser Gly Ala Pro
```

```
                370                 375                 380
Thr Thr Thr Pro Ala Pro Arg Pro Pro Thr Pro Ala Pro Thr Ile Ala
385                 390                 395                 400

Ser Gln Pro Leu Ser Leu Arg Pro Glu Ala Cys Arg Pro Ala Ala Gly
                405                 410                 415

Gly Ala Val His Thr Arg Gly Leu Asp Phe Ala Cys Asp Ile Tyr Ile
                420                 425                 430

Trp Ala Pro Leu Ala Gly Thr Cys Gly Val Leu Leu Leu Ser Leu Val
                435                 440                 445

Ile Thr Leu Tyr Cys Arg Arg Gly Arg Lys Leu Leu Tyr Ile Phe
                450                 455                 460

Lys Gln Pro Phe Met Arg Pro Val Gln Thr Thr Gln Glu Glu Asp Gly
465                 470                 475                 480

Cys Ser Cys Arg Phe Pro Glu Glu Glu Gly Gly Cys Glu Leu Arg
                485                 490                 495

Val Lys Phe Ser Arg Ser Ala Asp Ala Pro Ala Tyr Gln Gln Gly Gln
                500                 505                 510

Asn Gln Leu Tyr Asn Glu Leu Asn Leu Gly Arg Arg Glu Glu Tyr Asp
                515                 520                 525

Val Leu Asp Lys Arg Arg Gly Arg Asp Pro Glu Met Gly Gly Lys Pro
                530                 535                 540

Arg Arg Lys Asn Pro Gln Glu Gly Leu Tyr Asn Glu Leu Gln Lys Asp
545                 550                 555                 560

Lys Met Ala Glu Ala Tyr Ser Glu Ile Gly Met Lys Gly Glu Arg Arg
                565                 570                 575

Arg Gly Lys Gly His Asp Gly Leu Tyr Gln Gly Leu Ser Thr Ala Thr
                580                 585                 590

Lys Asp Thr Tyr Asp Ala Leu His Met Gln Ala Leu Pro Pro Arg Glu
                595                 600                 605

<210> SEQ ID NO 70
<211> LENGTH: 596
<212> TYPE: PRT
<213> ORGANISM: Artificial Sequence
<220> FEATURE:
<223> OTHER INFORMATION: Construct pCLS27604 (encoded amino acid
      sequence)

<400> SEQUENCE: 70

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
                20                  25                  30

Lys Lys Pro Gly Glu Thr Val Lys Ile Ser Cys Lys Ala Ser Gly Tyr
                35                  40                  45

Ile Phe Thr Asn Tyr Gly Met Asn Trp Val Lys Gln Ala Pro Gly Lys
                50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
                100                 105                 110

Ala Thr Tyr Phe Cys Ala Arg Ser Gly Gly Tyr Asp Pro Met Asp Tyr
                115                 120                 125
```

```
Trp Gly Gln Gly Thr Ser Val Thr Val Ser Ser Gly Gly Gly Ser
    130                 135                 140
Gly Gly Gly Gly Ser Gly Gly Gly Ser Asp Ile Val Leu Thr Gln
145                 150                 155                 160
Ser Pro Ala Ser Leu Ala Val Ser Leu Gly Gln Arg Ala Thr Ile Ser
                165                 170                 175
Cys Arg Ala Ser Glu Ser Val Asp Asn Tyr Gly Asn Thr Phe Met His
            180                 185                 190
Trp Tyr Gln Gln Lys Pro Gly Gln Pro Pro Lys Leu Leu Ile Tyr Arg
        195                 200                 205
Ala Ser Asn Leu Glu Ser Gly Ile Pro Ala Arg Phe Ser Gly Ser Gly
    210                 215                 220
Ser Arg Thr Asp Phe Thr Leu Thr Ile Asn Pro Val Glu Ala Asp Asp
225                 230                 235                 240
Val Ala Thr Tyr Tyr Cys Gln Gln Ser Asn Glu Asp Pro Pro Thr Phe
                245                 250                 255
Gly Ala Gly Thr Lys Leu Glu Leu Lys Arg Ser Asp Pro Gly Ser Gly
            260                 265                 270
Gly Arg Val Ala Ile Leu Trp His Glu Met Trp His Glu Gly Leu Glu
        275                 280                 285
Glu Ala Ser Arg Leu Tyr Phe Gly Glu Arg Asn Val Lys Gly Met Phe
    290                 295                 300
Glu Val Leu Glu Pro Leu His Ala Met Met Glu Arg Gly Pro Gln Thr
305                 310                 315                 320
Leu Lys Glu Thr Ser Phe Asn Gln Ala Tyr Gly Arg Asp Leu Met Glu
                325                 330                 335
Ala Gln Glu Trp Cys Arg Lys Tyr Met Lys Ser Gly Asn Val Lys Asp
            340                 345                 350
Leu Leu Gln Ala Trp Asp Leu Tyr Tyr His Val Phe Arg Arg Ile Gly
        355                 360                 365
Ser Gly Ala Pro Thr Thr Thr Pro Ala Pro Arg Pro Pro Thr Pro Ala
    370                 375                 380
Pro Thr Ile Ala Ser Gln Pro Leu Ser Leu Arg Pro Glu Ala Cys Arg
385                 390                 395                 400
Pro Ala Ala Gly Gly Ala Val His Thr Arg Gly Leu Asp Phe Ala Cys
                405                 410                 415
Asp Ile Tyr Ile Trp Ala Pro Leu Ala Gly Thr Cys Gly Val Leu Leu
            420                 425                 430
Leu Ser Leu Val Ile Thr Leu Tyr Cys Arg Arg Gly Arg Lys Lys Leu
        435                 440                 445
Leu Tyr Ile Phe Lys Gln Pro Phe Met Arg Pro Val Gln Thr Thr Gln
    450                 455                 460
Glu Glu Asp Gly Cys Ser Cys Arg Phe Pro Glu Glu Glu Glu Gly Gly
465                 470                 475                 480
Cys Glu Leu Arg Val Lys Phe Ser Arg Ser Ala Asp Ala Pro Ala Tyr
                485                 490                 495
Gln Gln Gly Gln Asn Gln Leu Tyr Asn Glu Leu Asn Leu Gly Arg Arg
            500                 505                 510
Glu Glu Tyr Asp Val Leu Asp Lys Arg Arg Gly Arg Asp Pro Glu Met
        515                 520                 525
Gly Gly Lys Pro Arg Arg Lys Asn Pro Gln Glu Gly Leu Tyr Asn Glu
    530                 535                 540
Leu Gln Lys Asp Lys Met Ala Glu Ala Tyr Ser Glu Ile Gly Met Lys
```

-continued

```
545                 550                 555                 560
Gly Glu Arg Arg Arg Gly Lys Gly His Asp Gly Leu Tyr Gln Gly Leu
                565                 570                 575

Ser Thr Ala Thr Lys Asp Thr Tyr Asp Ala Leu His Met Gln Ala Leu
                580                 585                 590

Pro Pro Arg Glu
        595

<210> SEQ ID NO 71
<211> LENGTH: 56
<212> TYPE: DNA
<213> ORGANISM: Artificial Sequence
<220> FEATURE:
<223> OTHER INFORMATION: Oligonucleotide scCAR-F

<400> SEQUENCE: 71
gcatcgtaat acgactcact atagggcagg ccaccatggc tttgcctgtc actgcc        56

<210> SEQ ID NO 72
<211> LENGTH: 26
<212> TYPE: DNA
<213> ORGANISM: Artificial Sequence
<220> FEATURE:
<223> OTHER INFORMATION: Oligonucleotide scCAR-R

<400> SEQUENCE: 72
ctagaggatc gctcgagtta ggtctc                                          26
```